US010991461B2

(12) United States Patent
Divine et al.

(10) Patent No.: US 10,991,461 B2
(45) Date of Patent: Apr. 27, 2021

(54) ASSESSING THE CURRENT STATE OF A PHYSICAL AREA OF A HEALTHCARE FACILITY USING IMAGE ANALYSIS

(71) Applicant: General Electric Company, Schenectady, NY (US)

(72) Inventors: Lucas Jason Divine, West Allis, WI (US); Curtis Gibeaut, Jr., Saukville, WI (US); Bryan Dickerson, Neosho, WI (US); Megan Wimmer, Milwaukee, WI (US)

(73) Assignee: General Electric Company, Schenectady, NY (US)

(*) Notice: Subject to any disclaimer, the term of this patent is extended or adjusted under 35 U.S.C. 154(b) by 876 days.

(21) Appl. No.: 15/616,915

(22) Filed: Jun. 7, 2017

(65) Prior Publication Data

US 2018/0247024 A1     Aug. 30, 2018

Related U.S. Application Data

(63) Continuation of application No. 15/442,386, filed on Feb. 24, 2017.

(51) Int. Cl.
*G16H 40/20* (2018.01)
*G06T 11/60* (2006.01)
(Continued)

(52) U.S. Cl.
CPC ......... *G16H 40/20* (2018.01); *G06K 9/00671* (2013.01); *G06T 11/60* (2013.01);
(Continued)

(58) Field of Classification Search
CPC ........ G16H 40/20; G16H 20/40; G16H 40/67; G16H 40/63; G06K 9/00671; G06T 11/60; G06T 19/006; G06T 2210/41
See application file for complete search history.

(56) References Cited

U.S. PATENT DOCUMENTS

| 5,745,387 A | 4/1998 | Corby, Jr. et al. |
| 6,230,142 B1 | 5/2001 | Benigno et al. |

(Continued)

FOREIGN PATENT DOCUMENTS

| JP | 2014-523041 A | 9/2014 |
| JP | 2015-523113 A | 8/2015 |

(Continued)

OTHER PUBLICATIONS

European Application No. 20168577.3 filed Jun. 23, 2017—European extended Search Report dated Jul. 3, 2020; 10 pages.
(Continued)

*Primary Examiner* — Janice A Mooneyham
*Assistant Examiner* — Steven G Sanghera
(74) *Attorney, Agent, or Firm* — Amin, Turocy & Watson, LLP

(57) ABSTRACT

Techniques for determining issues associated with a current state of an area of a healthcare facility are provided. In one example, a computer-implemented method comprises identifying an area of a healthcare facility included in image data captured of the healthcare facility, and characterizing aspects of a current state of the area of the area based on analysis of the image data, including determining object information characterizing objects included in the area. The method further comprises determining whether one or more of the aspects of the current state of the area deviate from a defined requirement for the area based on evaluation of the object information. Based on a determination that an aspect of the current state of the area deviates from the defined requirement for the area, the method can further comprise generating feedback information regarding the deviating aspect of the current state of the area.

18 Claims, 21 Drawing Sheets

(51) Int. Cl.
*G06T 19/00* (2011.01)
*G16H 40/63* (2018.01)
*G06K 9/00* (2006.01)
*G16H 40/67* (2018.01)
*G16H 20/40* (2018.01)

(52) U.S. Cl.
CPC .......... *G06T 19/006* (2013.01); *G16H 20/40* (2018.01); *G16H 40/63* (2018.01); *G16H 40/67* (2018.01); *G06T 2210/41* (2013.01)

(56) References Cited

U.S. PATENT DOCUMENTS

| | | |
|---|---|---|
| 7,331,929 B2 | 2/2008 | Morita et al. |
| 7,518,502 B2 | 4/2009 | Austin et al. |
| 7,774,044 B2 | 8/2010 | Sauer et al. |
| 7,958,079 B2 | 6/2011 | Fogel et al. |
| 8,407,081 B1 | 3/2013 | Rajasenan |
| 8,686,851 B2 | 4/2014 | Davis |
| 8,688,607 B2 | 4/2014 | Pacha |
| 9,208,474 B2 | 12/2015 | McKeown et al. |
| 9,256,711 B2 | 2/2016 | Horseman |
| 10,339,497 B2 * | 7/2019 | Gabbai ................. G06Q 10/04 |
| 10,467,811 B1 * | 11/2019 | Cederlof ................. G06F 3/011 |
| 2002/0099273 A1 | 7/2002 | Bocionek et al. |
| 2004/0153340 A1 | 8/2004 | Christ et al. |
| 2008/0059292 A1 | 3/2008 | Myers et al. |
| 2008/0082463 A1 | 4/2008 | Cheng et al. |
| 2008/0106374 A1 | 5/2008 | Sharbaugh |
| 2010/0167248 A1 | 7/2010 | Ryan |
| 2011/0153341 A1 | 6/2011 | Diaz-Cortes |
| 2013/0009993 A1 | 1/2013 | Horseman |
| 2013/0093829 A1 | 4/2013 | Rosenblatt et al. |
| 2013/0267838 A1 | 10/2013 | Fronk et al. |
| 2013/0301901 A1 | 11/2013 | Satish et al. |
| 2014/0031668 A1 * | 1/2014 | Mobasser ............ A61B 5/0075 600/409 |
| 2014/0275760 A1 | 9/2014 | Lee et al. |
| 2015/0187038 A1 | 7/2015 | Johnson |
| 2015/0209114 A1 * | 7/2015 | Burkholz .............. A61M 5/315 600/562 |
| 2016/0004911 A1 | 1/2016 | Cheng et al. |
| 2016/0026253 A1 * | 1/2016 | Bradski .............. H04N 13/3444 345/8 |
| 2016/0232687 A1 | 8/2016 | Morand et al. |
| 2016/0306505 A1 | 10/2016 | Vigneras et al. |

FOREIGN PATENT DOCUMENTS

| | | |
|---|---|---|
| JP | 2016-157435 A | 9/2016 |
| WO | 2013/006642 A2 | 1/2013 |
| WO | 2013049386 A1 | 4/2013 |
| WO | 2015054240 A1 | 4/2015 |
| WO | 2015/116805 A1 | 8/2015 |

OTHER PUBLICATIONS

Wee Sim Khor et al: "Augmented and virtual reality in surgery-the digital surgical environment: applications, limitations and legal pitfalls", Annals of Translational Medicine, vol. 4, No. 23, Dec. 1, 2016 (Dec. 1, 2016), pp. 454-454, XP055423487, ISSN: 2305-5839, DOI: 10.21037/atm.2016.12.23 the whole document. 11 pages.
International Search Report and Written Opinion for International Application No. PCT/US2017/038949, dated Feb. 8, 2018. 17 pages.
Vallejo, E., "Sight: Contact Lenses with Augmented Reality—Futuristic Video," YouTube, Jul. 29, 2012, https://www.youtube.com/watch?v=GJKwHAvR4ul.
The Verge, "Microsoft HoloLens: what it's really like," YouTube, Apr. 1, 2016, https://www.youtube.com/watch?v=4p0BDw4VHNo.
CN2 Inc., "CN2—Augmented Reality Medical Glasses," YouTube, Jun. 19, 2015, https://www.youtube.com/watch?v=FRWcYvSv2To.
Philips Healthcare, "Google Glass proof of concept—Philips Healthcare," YouTube, Oct. 3, 2013, https://www.youtube.com/watch?v=ssIdTFWBv3E.
Non-Final Office Action received for U.S. Appl. No. 15/442,386 dated Sep. 24, 2020, 70 pages.
Final Office Action received for U.S. Appl. No. 15/442,386 dated Jan. 24, 2020, 56 pages.
International Search Report and Written Opinion for International Application Serial No. PCT/US2107/038949 dated Feb. 8, 2018, 17 pages.
Non-Final Office Action received for U.S. Appl. No. 15/442,386 dated Jun. 25, 2019 , 71 pages.
Invitation to Pay Additional Fees and Partial International Search for International Application Serial No. PCT/US2107/038949 dated Nov. 21, 2017, 12 pages.
Wee Sim Khor et al.; "Augmented and Virtual Reality in Surgery—the Digital Surgical Environment: Applications, Limitations and Legal Pitfalls", Annals of Translation Medicine, vol. 4, No. 23, Dec. 1, 2016; pp. 454-454.
Notice of Reasons for Refusal received for Japanese Patent Application U.S. Appl. No. 2019-544806 dated Feb. 9, 2021, 10 pages.
Final Office Action received for U.S. Appl. No. 15/442,386 dated Mar. 15, 2021, 85 pages.

* cited by examiner

ASSESSING THE CURRENT STATE OF A PHYSICAL AREA OF A HEALTHCARE FACILITY USING IMAGE ANALYSIS

RELATED APPLICATION

This application is a continuation of and claims priority to U.S. patent application Ser. No. 15/442,386, filed Feb. 24, 2017 and titled "PROVIDING AUXILIARY INFORMATION REGARDING HEALTHCARE PROCEDURE AND SYSTEM PERFORMANCE USING AUGMENTED REALITY," the entirety of which application is incorporated herein by reference.

TECHNICAL FIELD

The subject matter disclosed herein relates to techniques for assessing the current state of a physical area of a healthcare facility using image analysis.

BACKGROUND

In the healthcare field, there are often best practices for performing healthcare related procedures, whether it is a medical procedure performed by a healthcare clinician on a patient, a clerical procedure involving data entry, a maintenance procedure involving ensuring a medical environment and associated equipment is properly maintained, or the like. These best practices can be government mandated or implemented by the medical organization's internal policies, and are intended to facilitate optimal performance of the healthcare organization in terms of quality of patient care and financial return. Further, certain activity may have different official procedures based on which government or insurance company is paying for the healthcare activity.

Given the complexity of modern healthcare organizations attributed to the medical services provided and the highly variable and sensitive nature of patient care, it can be extremely difficult for healthcare professionals to adhere to such best practices. For example, administering medical procedures to a patient traditionally relies on many healthcare personnel interacting with one another in highly variable and volatile scenarios. The ability for each of individual to adhere to best practice standards can be influenced by the actions of everyone involved, the condition of the patient, the stress and fatigue of the clinicians, the availability and proper functioning of necessary supplies and equipment, and possible distractions in the surroundings. Human error is inevitable. In the healthcare field, the costs associated with human errors can have a severe impact on patient well being as well as financial cost to the serving healthcare organization. Further, many insurance companies only pay for certain procedures if the procedure have been performed according to their set forth protocol. Thus mechanisms for facilitating adherence to defined practice standards and minimizing errors associated with deviations from the defined practice standards are of great importance.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, apparatus and/or computer program products that facilitate providing auxiliary information regarding healthcare procedure and system performance using augmented reality.

In one embodiment, a system is provided that comprises a memory that stores computer executable components, and a processor that executes computer executable components stored in the memory. The computer executable components can comprise a procedure characterization component configured to determine descriptive information regarding performance of a healthcare related procedure by a user based on input data generated in real-time during the performance of a healthcare procedure by the user, wherein the input data comprises video captured of the user during the performance of the healthcare related procedure. The computer executable components can further comprise a procedure assessment component configured to determine whether an aspect of the performance of the healthcare related procedure currently being performed by the user deviates from a defined protocol for the healthcare related procedure based on comparison of the descriptive information with reference descriptive parameters for the healthcare related procedure, and a feedback component configured to determine feedback information regarding correction of the aspect in response to a determination that the aspect deviates from the defined protocol. In some implementations, the computer executable components can also comprise an augmented reality data component configured to generate overlay data representative of the feedback information for projection on a display over a current view of the user in response to the determination that the aspect deviates from the defined protocol.

In another embodiment, a system is provided that comprises a memory that stores computer executable components, and a processor that executes computer executable components stored in the memory. The computer executable components can comprise a recognition component that analyzes captured image data of a physical area of a healthcare facility and identifies one or more objects within the captured image data, and an assessment component that assesses a state of performance of the healthcare facility based on the one or more of the objects. The computer executable components can further comprise a feedback component that determines feedback information regarding the state of performance, a selection component that selects a subset of the feedback information for providing to a user based in part on a context of the user, and an augmented reality data component that generates overlay data representative of the subset of the feedback information for projection on a display over a current view of the physical area of the healthcare facility that is viewed by the user.

In one or more additional embodiments, a method is described that comprises receiving, by a system comprising a processor, input data generated in real-time during performance of a healthcare procedure by a user, wherein the input data comprises video captured of the user during the performance of the healthcare related procedure. The method further comprises determining, by the system, descriptive information characterizing the performance based on the input data, wherein the descriptive information characterizes at least actions performed by the user during the procedure. The method further comprises determining, by the system, whether an aspect of one of the actions currently being performed by the user deviates from a defined protocol for the healthcare related procedure based on comparison of the descriptive information with reference descriptive parameters for the healthcare related procedure, and determining, by the system, feedback information regarding correction of the aspect in response to a determination that the aspect deviates from the defined protocol. In some implementations, the method can also comprise generating, by the system, overlay data representative of the feedback information for projection on a display over a current view of the user in response to the determination that the aspect deviates from the defined protocol.

DETAILED DESCRIPTION

Figure 1:
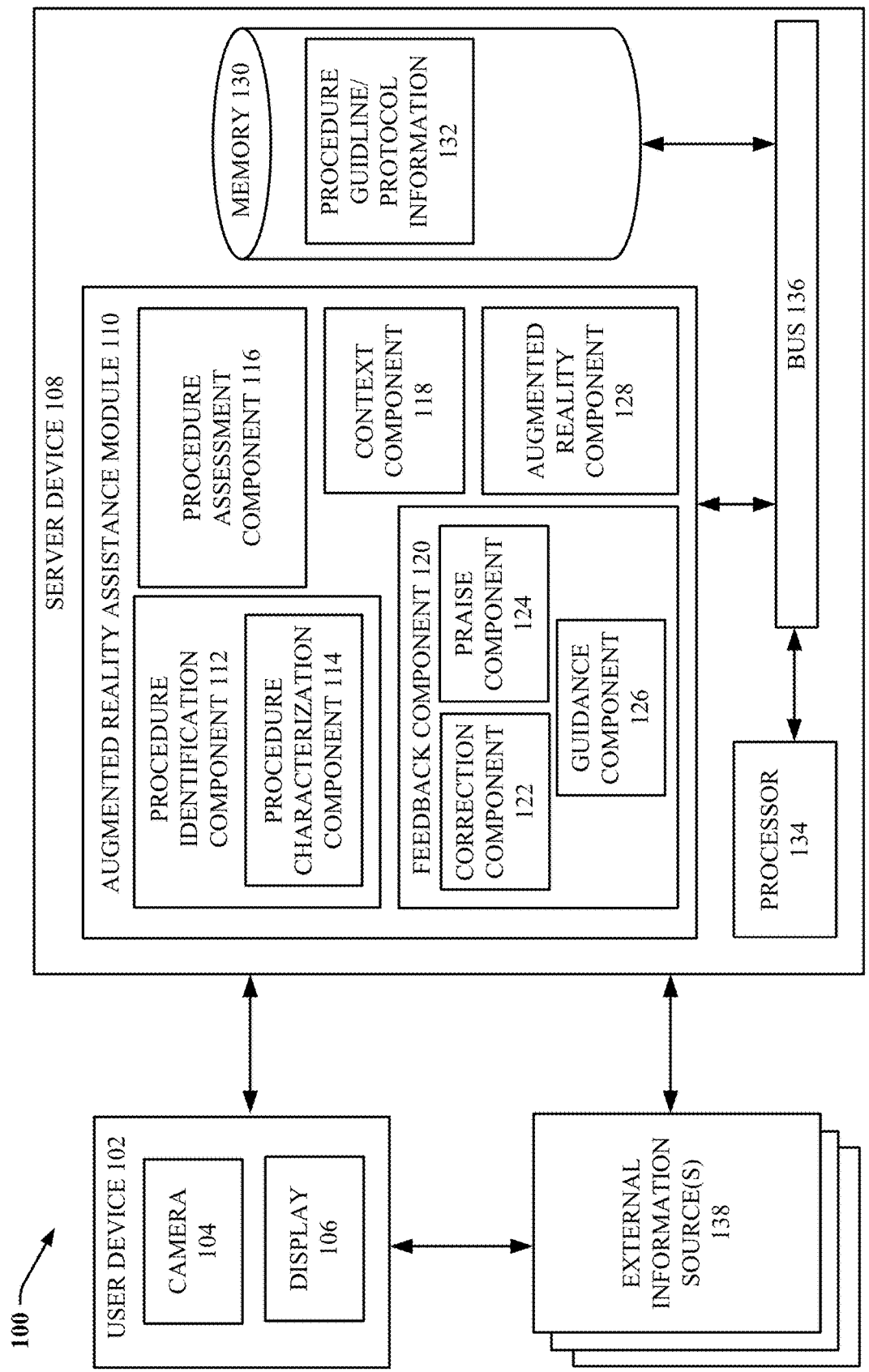
FIG. 1 illustrates a block diagram of an example system that facilitates providing auxiliary information regarding healthcare procedure performance using augmented reality (AR) in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments of the subject disclosure are directed to computer processing systems, computer-implemented methods, apparatus and/or computer program products that facilitate preventing or minimizing human error associated with performance of healthcare related procedures by a healthcare professional providing auxiliary information regarding healthcare procedure performance using augmented reality (AR). In particular, one or more embodiments of the disclosed systems provide mechanisms to improve human behavior through AR guidance. For example, the subject AR systems and methods contemplated herein can help guide staff to complete the correct procedure steps based on which procedure is correct based on many factors discussed herein, and including which government and/or insurance agency may be paying for the activity. Further, in some implementations, the subject AR systems can detect when human behavior may be an improvement over current procedures and methods and propose those improvements to leadership.

The term "healthcare professional" is used herein to refer to any entity that performs a healthcare related procedure or action. The type of the healthcare related procedure or action can vary. For example, a healthcare related procedure can include but is not limited to, a medical procedure performed by a healthcare clinician on a patient, a clerical procedure performed by a clerical employee, a maintenance procedure performed by a maintenance employee, or the like. Thus a healthcare professional can include for example but not limited to: a clinician (e.g., a physician, a nurse, a physician's assistant, a therapist, a medical technician, etc.), a clerical worker of a healthcare organization (e.g., a medical records technician, a medical secretary, a medical billing assistant), a maintenance worker of a healthcare organization (e.g., a medical equipment technician), or the like. A medical procedure is a course of action intended to achieve a result in the delivery of healthcare. A medical procedure with the intention of determining, measuring, or diagnosing a patient condition or parameter is also called a medical test. Other common kinds of medical procedures are therapeutic (e.g., intended to treat, cure, or restore function or structure), such as surgical and physical rehabilitation procedures. In regard to the subject disclosure, a medical procedure may involve some physical interaction between a clinician and a patient. Medical procedures are often defined by a standardized coding system wherein the respective procedures have defined codes. The coding system can vary from one medical organization to another or may be standardized by a governing body.

In one or more implementations, as a healthcare professional is performing a healthcare related procedure, a computer system can monitor the respective actions performed by the healthcare professional in real-time. For example, in some embodiments, image data (e.g., video and/or still images) and audio data can be captured of the healthcare professional performing the procedure. With these embodiments, the computer system can receive the image and audio data in real-time (e.g., as it is being captured). Using image based pattern recognition techniques (e.g., object detection, movement/motion detection, etc.), the computer system can determine respective aspects of the procedure being performed in real-time. For example, based on analysis of the image data, the computer system can identify a specific type of procedure being performed by the healthcare professional (e.g., a specific type of medical procedure performed on a patient, a specific type of clerical procedure, a specific type of maintenance procedure, etc.). The computer system can further identify respective actions performed by the healthcare professional in association with performance of the procedure and characteristics of the respective actions. For example, in association with monitoring a clinician performing an intravenous (IV) cannulation procedure, the computer system can identify and characterize steps of the procedure including but not limited to: preparation of the IV site, preparation of the tubing and the fluid bag, application of the tourniquet, selection of the catheter, insertion of the catheter, removal of the tourniquet, attaching the tubing, and opening of the IV line. According to this example, using automated pattern recognition image analysis techniques, the computer system can identify if and when the healthcare professional is performing the respective steps of the IV cannulation procedure, timing of performance of the respective steps, order of performance of the respective steps, and various defined characteristics of the respective steps (e.g., location of the IV site, size of the tubing, size of the catheter, dosage of the fluid bag, location of the tourniquet, etc.).

In some embodiments, the computer system can also receive various other forms of input/feedback that can be used to monitor and characterize various aspects of a procedure being performed by a healthcare professional. For example, these other forms of input/feedback can include audio spoken by the healthcare professional, the patient, other healthcare professionals involved in the procedure and/or audio generated by a machine associated with the procedure (e.g., an alarm sound). In another example, the feedback can include sensory feedback captured via motion and/or biometric sensors worn by the healthcare professional, the patient, or other healthcare professionals involved in the procedure. In yet another example, the feedback can include motion data regarding motion of a medical instrument or device used during the procedure. In yet another example, the feedback can include input received or captured by a machine or instrument used during the procedure.

In association with identifying and characterizing the respective steps of the procedure performed by the healthcare based on the various types of input/feedback discussed above, the computer system can further analyze the steps to determine whether the healthcare professional is performing the procedure correctly and in accordance with predefined best practice standards for the procedure. In some implementations, if the computer system determines the healthcare professional is performing an aspect of the procedure incorrectly or otherwise in deviation of the predefined standards for the procedure, the computer system can provide the healthcare professional with auxiliary information in real-time regarding the error. For example, the computer system can provide the healthcare professional with auxiliary information identifying the error. In another example, the computer system can provide the healthcare professional with auxiliary information indicating how to correct the error. In other implementations, if the computer system determines the healthcare professional is performing an aspect of the procedure correctly, the computer system can provide the healthcare professional with auxiliary information in real-time acknowledging or praising the healthcare professional's good performance. In yet another implementation, based on recognition of a type of procedure being performed by a healthcare professional, the computer system can monitor the performance of the procedure and provide auxiliary information with step by step guidance regarding how to perform the procedure correctly.

In accordance with various embodiments described herein, the auxiliary information can be provided to the healthcare professional in real-time in using an AR device. Augmented reality (AR) is a live direct or indirect view of a physical, real-world environment whose elements are augmented (or supplemented) by computer-generated sensory input such as graphics, sound, video, or other data. As used herein, an "AR device" includes a computer device capable of generating an AR experience. In some embodiments, an AR device can include a device that comprises a display configured to render overlay data onto a live view of real-world physical environment. For example, in some implementations, the AR device is an eyewear device, such as glasses, goggles, a heads-up display (HUD), a contact lens or pair of contact lenses, or the like, that is configured to render overlay data onto a display of the eyewear device while a user is wearing the eyewear device and also viewing the real-world environment. In another implementation, the AR device can include an eyewear device or a handled computing device (e.g., a tablet, a smartphone, or the like), configured to render overlay data onto live image or video data captured of the environment. In other implementations, an AR device can include a device configured to render audio, vibratory or other sensory signals in association with viewing a real-world environment. The AR device may include speakers or headphones for audio output.

In this regard, in one or more embodiments, as a healthcare professional is performing a healthcare related procedure, the healthcare professional can wear, hold, or otherwise view an AR device. The AR device can provide a real or live image/video view of the healthcare professional's environment from the healthcare professional's perspective via a display of the AR device. For example, with reference to the IV cannulation procedure example, a healthcare professional performing the IV cannulation procedure can wear or otherwise employ an AR device during the procedure that presents a live view, from the healthcare professional's perspective, of the IV site, the patient, the fluid bag, etc., as the healthcare professional is viewing these objects when performing the procedure. If the system determines that the healthcare professional is performing or has performed an aspect of the procedure incorrectly, the system can generate auxiliary information regarding the error in the form of overlay data to be projected on the display of the AR device over the live view (e.g., either real or video/image data) of the environment. For example, the overlay data can include but is not limited to: text, a symbol, a marker, a tag, an image, a video, an animation, or a hyperlink. The AR device can further render the overlay data via the display of the AR device over the live view (e.g., either real or video/image) of the environment also presented on or viewed through the display.

In some implementations, depending on the type of overlay data and/or the aspect of the procedure the overlay data associated with, the overlay data can be displayed in a manner such that it appears spatially situated (e.g., in two-dimensional (2D) or three-dimensional (3D) space) relative to an object or part of an object associated with the aspect of the procedure. For example, with reference again to the IV cannulation procedure example, if the system detects incorrect placement of the IV needle relative to the patient's IV site, the system can generate overlay data that indicates the incorrect placement of the IV needle and identifies how to correct the placement of the IV needle relative to the patient's IV site. The AR device can further render the overlay data such that it appears spatially situated relative to a live view of the patient's IV site. By providing such visual auxiliary information regarding healthcare procedure performance in real-time using AR, the disclosed techniques greatly reduce human error by giving the healthcare professional real-time and relevant instructions that guide the healthcare professional with making necessary adjustments during the procedure.

One or more additional embodiments of the subject disclosure are directed to computer processing systems, computer-implemented methods, apparatus and/or computer program products that facilitate providing auxiliary information regarding healthcare system performance in real-time using AR. With respect to large scale healthcare organizations providing various different patient services and having many (e.g., hundreds, thousands, or more) employees that perform a variety of interrelated clinical and non-clinical roles, it can be extremely difficult for an administrative worker to have a thorough understanding of a current state of performance of the healthcare organization with respect to different areas of the healthcare organization, let alone the healthcare organization as whole. A healthcare administrator is generally responsible for the overall directing of operations of the healthcare organization to achieve the long-range and short-range goals and objectives of the organization. For example, the administrator may be responsible for the daily administration and leadership of the a certain department or sector of the organization or the organization (e.g., surgery); accountable for directing, coordinating and controlling all aspects of financial management, inventory management, facility maintenance, surgical services, patient relations and staff; responsible for fostering positive work relationships and serve as a liaison between the governing body, medical staff, employees and all areas of the department; and accountable for improving the clinical and financial operations of the department. It is often difficult for an administrator to perform these duties merely by looking at data reports with charts and numbers. For example, the administrator may not have a strong concept regarding how the different types of equipment, supplies, and clinician services associated with a particular department are utilized on a regular basis, and the current issues affecting their performance. In another example, the administrator may not have a good understanding of what a particular piece of equipment is used for, how its use impacts the workflow of a particular medical sector of the hospital, how its use influences other supplies and systems of the healthcare facility, and the like.

The subject disclosure provides computer processing systems, computer-implemented methods, apparatus and/or computer program products that facilitate a user (e.g., an administrator of the healthcare organization or another suitable entity) with understanding information concerning a state of performance of a healthcare organization by providing the healthcare administrator with auxiliary information associated with a current physical area of a healthcare facility of the organization the healthcare professional is viewing or otherwise examining. In one or more implementations, the state of performance can relate to a clinical and/or financial performance state of the healthcare organization. In particular, based on captured image data and/or other input information a computing system can determine an area of a healthcare facility that the user is currently looking at, or has requested to look at. The computing system can further identify objects, equipment, supplies, people, etc., included in the area (or associated with the area), and further determine auxiliary information associated with the objects, equipment, supplies, people, etc., The auxiliary information can include but is not limited to, equipment information regarding utilization and/or performance of equipment associated with the area, employee information regarding utilization and/or performance of the employees associated with the area, and recommendation information regarding recommendations for improving the performance of the healthcare organization in association with changing an aspect of the equipment and/or employee utilization and/or performance associated with the area (e.g., addition or removal of resources). For example, in association with viewing a particular room in a hospital, the user can be automatically provided with auxiliary information associated with performance of the healthcare organization based on utilization of the room, including but not limited to: information identifying medical supplies and equipment included in the room, information regarding usage of the medical supplies and equipment, and financial information concerning usage of the medical supplies and equipment. In another implementation, the auxiliary information can include employee information regarding employees included in the room or otherwise associated with the room. For example, the employee information can but is not limited to: identities of employees included in or otherwise associated with the room (e.g., employees that use the room, employees scheduled for procedures in the room, employees responsible for maintenance of the room and the like), role description information describing one or more aspects of the role or service provided the employee, performance information regarding performance of the employee with respect to their role or job duties, financial information regarding ROI associated with the respective employees, personal information associated with the respective employees, and the like. The auxiliary information can further include various other types of information associated with utilization of the room that relates to or have an impact on the clinical and financial performance of the healthcare organization, such as but not limited to: procedures performed in the room, frequency of the procedures, outcomes of the procedures, ROI of the procedures, maintenance issues associated with the room, scheduled updates to the room, purchase orders, and the like.

In various implementations, the amount and type of auxiliary information that is provided to a particular administrator can be filtered and selected based on a current context of the user. For example, the auxiliary information that is provided to a maintenance worker can reflect maintenance issues associated with equipment in an observed area while the auxiliary information that is provided to a finance executive can concern cost and ROI performance data associated with equipment and/or medical services supported by the area. In another example, in association with providing a user with information regarding employees the user interacts with, the auxiliary information provided can be based on a relationship between the user and the employee and/or an intention for interacting with the employee. For example, if the user is merely passing by an employee that the user is not well acquainted with, the user can be provided with information reminding the user of the employee's name and prompting the user to congratulate the employee on his or her promotion. Alternatively, if the user is meeting with an employee to discuss improving the employee's performance, the user can be provided with auxiliary information that highlights some important past performance statistics.

Similar to the auxiliary information provided to user in association with performance of a procedure, in some implementations the auxiliary information regarding the state of performance of the healthcare organization can be provided to the user using an AR experience. For example, using an AR device, a user can physically visit an area of a healthcare facility and receive auxiliary information concerning the performance of the area, including equipment and supplies associated with the area, people (e.g., employees, patients, visitors, etc.) associated with the area, and the like. The auxiliary information can be rendered to the user via the display of the AR device as overlay data that is overlaid onto a current view of the area viewed through or on the display. In another implementation, the user can remotely view the area by viewing video and/or image data captured of the area (e.g., via one or more cameras dispersed throughout the healthcare facility). According to this implementation, the auxiliary data can be overlaid onto the video and/or image data of the area that is displayed on the user's remote device. Still in yet another implementation, the user can view the area using a virtual reality (VR) system/device. VR is a realistic and immersive simulation of a three-dimensional environment, created using interactive software and hardware, and experienced or controlled by movement of the body. According to this implementation, using a VR device, a user can be presented with a 3D space model/visualization of the area that appears to the user as if the user is actually standing in the 3D space model. The auxiliary data regarding the area can be projected onto or otherwise integrated within the 3D space model view of the area.

In various embodiments, regardless as to whether the user is viewing the auxiliary data using an AR device or a VR device, the auxiliary data can be spatially aligned with respective objects, people, equipment/supplies, etc., that is associated with. For example, auxiliary data concerning how a supply cabinet in a room is under stocked with certain supplies can be overlaid on a direct view of the supply cabinet (e.g., the supply cabinet viewed through a transparent display, such as AR glasses or goggles), or an indirect view of the supply cabinet (e.g., video/image data or 3D model data of the supply cabinet presented on a display).

The various embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 illustrates a block diagram of an example, non-limiting system 100 that facilitates providing auxiliary information regarding healthcare procedure performance using AR in accordance with one or more embodiments described herein. Aspects of systems (e.g., system 100 and the like), apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

System 100 includes a user device 102, a server device 108 and one or more external information sources 138. The respective devices/sources of system 100 can include computer executable hardware and/or software components. For example, in the embodiment shown, the server device 108 includes (or is otherwise operatively coupled to) at least one memory 130 that stores computer-executable components. In one or more embodiments, these computer executable components include the augmented reality (AR) assistance module 110 and associated components. The server device 108 can also include (or is otherwise operatively coupled to) at least one processor 134 that executes the computer-executable components stored in the memory 130. The server device 108 can further include a system bus 136 that can couple the various components of the server device 108 including, but not limited to, the AR assistance module 110, the memory 130 and the processor 134.

The AR assistance module 110 can be configured to perform various AR type services associated with facilitating healthcare professionals performing their jobs. In accordance with system 100, the AR assistance module 110 is particularly configured to assist healthcare professionals when performing a defined procedure by providing the healthcare professional with auxiliary information, determined in real-time, that is relevant to a current aspect of the procedure being performed. In various implementations, the auxiliary information is designed to help the healthcare professional perform the procedure in accordance with a predefined protocol, standard, or best practice for performing the procedure. The auxiliary information can be provided to the healthcare professional in real-time during performance of the procedure via a user device 102 associated with the healthcare professional.

For example, in one or more embodiments, the user device 102 is an AR device that is worn by (e.g., an eyewear device) or otherwise viewed by the healthcare professional during performance of the procedure. According to these embodiments, the auxiliary information can be rendered via a display (e.g., display 106) of the AR device in the form of overlay data that is overlaid or projected onto a live view of the healthcare professional's environment. For example, the live view can include a direct view of the healthcare professional's environment as viewed through a transparent display (e.g., display 106), such as a transparent display that is worn over the healthcare professionals eye or eyes (e.g., glasses, goggles, contact lenses, etc.). In another example, the live view can include an indirect view of the healthcare professional's environment that comprises video or image data of the environment captured from the healthcare professional's perspective via a camera (e.g., camera 104) and rendered on a display (e.g., display 106) of the AR device.

For example, in the embodiment shown, the user device 102 includes at least one camera 104 and a display 106. Speakers or other audio output may also be included in some embodiments. The camera 104 can include any suitable camera configured to capture image data, including still images and/or video. For example, in one or more embodiments, the camera 104 can capture live video of a healthcare professional's environment in association with performance of a healthcare procedure by the healthcare professional. The live video can be rendered via the display 106 and/or provided to the server device 108 for processing by the AR assistance module in association with monitoring the healthcare professional's performance of the healthcare procedure and providing real-time feedback to the healthcare professional regarding the performance. In some implementations, the camera 104 can be configured to capture and/or determine depth or distance information for features included in the captured image data. The depth information can be used to facilitate spatially aligning overlay data with objects appearing in the image data and/or a real physical view of the healthcare professional's environment. The spatial data can also be used to facilitate identifying objects appearing in the image data, spatial relationships of objects appearing in the image data, and tracking movement of objects appearing in sequence of images captured over time (i.e., video data).

In other embodiments, one or more additional cameras external to the user device 102 can be dispersed throughout a healthcare environment and capture image data (e.g., still images and/or video) of a healthcare professional performing a healthcare procedure. For example, one or more cameras can be located at different positions in an operating room, examination room, laboratory room, at different positions throughout a hospital, etc. These cameras can be configured to capture image data and/or video data associated with procedures performed in the healthcare environment and provide the image data to the server device 108 in real-time for processing by the AR assistance module 110.

The one or more external information sources 138 can include various systems and databases that can provide information to the AR assistance module 110 that facilitates evaluating performance of a healthcare related procedure and/or performance of various aspects of a healthcare organization. For example, the one or more external information sources 138 can include systems, servers, devices, etc., that are internal to a particular healthcare organization providing and/or controlling the server device 102 and associated AR assistance module 110, as well as various remote systems, server, devices, etc., accessible via a network (e.g., the Internet). The one or more external information sources 138 can also include various systems and databases that facilitate the AR assistance module 110 with respect to generating and providing auxiliary information to healthcare professional, in real-time, based on the performance evaluations.

For example, the one or more external information sources 138 can include a source with information regarding various defined healthcare related procedures that can be monitored by the AR assistance module 110, including information identifying the respective procedures and descriptive information comprising descriptive parameters describing characteristics of the respective procedures. In another example, the one or more external information sources 138 can include information regarding defined guidelines or protocols for the respective healthcare related procedures. These guidelines/protocols can be defined by the healthcare organization and/or government mandated. For example, government organizations like the U.S. institutions of National Institutes of Health or Medicare may be examples of institutions with mandated procedures in certain cases.

In some implementations, these guidelines and protocols can be optimized over time using various machine learning techniques and data monitored for repeated or similar procedures. For example, the procedure guideline/protocol information can include descriptive parameters that define required steps or actions for a procedure and timing for the respective steps or actions, including an order of for performance of the respective actions. The procedure guideline/protocol information can also include descriptive parameters that define how the respective actions/steps should be performed, what supplies/instruments should be used, how to dispose of supplies, how to interact with a patient and/or other healthcare professionals during a procedure and the like. In another example, the guideline/protocol information can include descriptive parameters regarding responsive actions/steps to be taken when various potential events, reactions, or complications arise during a procedure. It should be appreciated that the various types of information included in guideline/protocol information regarding how to perform a medical related procedure according to a desired standard can vary depending on the type of procedure performed and the organization defining the guideline/protocol. In the embodiment shown, such procedure guideline/protocol information is located at the server device 108 (e.g., in memory 130 as procedure guideline/protocol information 132), however, it should be appreciated that the specific location of information can vary so long as it is accessible to the AR assistance module to facilitate real-time evaluation of procedures being performed by healthcare professionals.

In another example, the one or more external information sources 138 can include employee information identifying all healthcare professional employees of a healthcare organization that employs the AR assistance module 110 to facilitate monitoring and improving the performance of the healthcare organization. Such healthcare organizations can include but are not limited to: hospital networks, hospitals, nursing homes, assisted living facilities, physical therapy organizations, billing organizations, pharmacies, etc. For example, the employee information can identify the respective healthcare professional employees, their roles (e.g., job title), the patients they work with (if having a clinician role), the procedures they are authorized to perform, the procedures they are expected to perform, and the like. The employee information can also include any possible performance information that can be monitored and recorded for the employee over time, such as hours worked, procedures performed, outcomes of the procedures, evaluations of the procedures, satisfaction of patients, reviews of the employee, information regarding how the employee performs certain tasks relative to other employees or another benchmark, and the like. The employee information can also include financial information regarding salary of the respective employees, return on investment (ROI) generated from the respective employees, and the like. The employee information can also include personal information associated with the respective employees, such as information regarding an employee's family and friends, preferences, birthday, hobbies, awards, vacations, and the like. The employee information can be updated on a regular basis (e.g., hourly, daily, weekly, etc.) such that the information source provides current information regarding various aspects of an employee's work life and personal life.

The one or more external information sources 138 can also include patient record information, including information identifying patients of a healthcare organization or healthcare provider that employs the AR assistance module 110 to facilitate monitoring and improving the performance of the healthcare organization or healthcare provider. The patient information can include but is not limited to: patient health records (e.g. electronica medical records or "EMRs"), patient laboratory result information, patient imaging study information, patient diagnosis information, scheduling information, physician information, prescription information, care plan information, allergy information, insurance information, and the like. The patient information can also include personal information associated with the patient, such as information regarding the patient's family and friends, preferences, birthday, hobbies, and the like.

The one or more external information sources 138 can also include information regarding the physical environment of a healthcare organization facility, such as but not limited to: information regarding the layout or floor plan of the facility, information identifying relative locations of the respective buildings, sectors, rooms, etc., information identifying what the respective buildings, sectors, rooms, etc., are used for, information regarding equipment at the healthcare facility and relative physical locations of the equipment, information regarding medical supplies at the healthcare facility and relative locations of the medical supplies, and the like. The one or more external information sources 138 can also include information regarding operating status and maintenance issues associated with the equipment. The one or more external information sources 138 can also include performance information associated with services rendered, quality of patient, and financial performances of the healthcare organization based on specific areas and equipment of the facility. For example, such performance information can relate to utilization of the equipment and supplies including financial information associated with the utilization of the equipment and supplies, procedures performed in the respective buildings, sectors, rooms, etc., outcomes of the procedures, quality of the procedures, frequency of the procedures, durations of the procedures and financial information associated with the procedures. Such performance information can include information regarding relationships between patients, patient medical conditions, patient outcomes, patient quality, aspects of courses of patient care (e.g., diagnoses, inpatient and outpatient length of stay, operations/procedures performed), medical procedures, medical personnel, resources employed, pharmaceuticals employed, medical devices employed, costs, reimbursement, return on investments (ROI), and the like.

In the embodiment shown, the user device 102 and the server device 108 are configured to operate in a server/client relationship, wherein the server device 108 employs the AR assistance module to monitor and evaluate a medical related procedure being performed by a healthcare professional and provide auxiliary information regarding the procedure to the healthcare professional at the user device 102. In some embodiments, the user device 102 can provide the server device 108 with image/video data captured of the healthcare professional performing the procedure, (e.g., via the camera 104), that is used by the AR assistance module 110 to evaluate the performance. In other implementations, the image/video data can be captured by and provided to the server device 108 via one or more other cameras in the located in the healthcare professional's environment that are configured to capture video/image data of the healthcare professional performing a medical related procedure. However, it should be appreciated that although system 100 employs a server/client architecture, the various features of the subject disclosure are not limited to this architecture. For example, in some embodiments, the AR assistance module 110 and/or one or more components of the AR assistance module 110 can be provided at the user device 102 or another device (not shown). In another example, the one or more external information sources 138 can be located at the user device 102 and/or the server device 108.

In one or more embodiments, the user device 102, the server device 108 and/or the one or more external information sources 138 can be communicatively coupled either directly or indirectly via one communication networks (not shown). Such communication networks can include wired and wireless networks, including, but not limited to, a cellular network, a wide area network (WAN) (e.g., the Internet) or a local area network (LAN). For example, the user device 102 can be configured to communicated with the server device 108 (and vice versa) using virtually any desired wired or wireless technology, including but not limited to: wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Zigbee and other 802.XX wireless technologies and/or legacy telecommunication technologies, BLUETOOTH®, Session Initiation Protocol (SIP), ZIGBEE®, RF4CE protocol, WirelessHART protocol, 6LoWPAN (IPv6 over Low power Wireless Area Networks), Z-Wave, and/or an ultra-wideband (UWB) standard protocol.

The user device 102 can include any suitable computing device associated with a user and that can receive and/or render auxiliary information generated by the AR assistance module 110. For example, the one user device can include a desktop computer, a laptop computer, a television, an Internet enabled television, a mobile phone, a smartphone, a tablet user computer (PC), or a personal digital assistant (PDA). In various exemplary embodiments, the user device 102 includes a wearable computing device configured to provide an AR, virtual reality (VR) and/or mixed reality experience in association with rendering auxiliary data associated with performance of a medical related procedure by a healthcare professional. For example, the user device 102 can include device configured to be worn on or near a user's eye, such as glasses, goggles, contact lenses, a HUD device, and the like. As used in this disclosure, the terms "user," "healthcare professional," "clinician," "employee," "administrator" and the like refer to a person, entity, system, or combination thereof that can employ system 100 (or additional systems described in this disclosure) using a user device 102.

In the embodiment shown, the AR assistance module 110 includes procedure identification component 112, procedure assessment component 116, context component 118, feedback component 120, and augmented reality (AR) component 128. In order to facilitate generating and providing auxiliary information to a healthcare professional that is relevant to a current aspect of a medical related procedure being performed by the healthcare professional, the AR assistance module 110 can monitor and evaluate input received in real-time (e.g., during the performance of the procedure) regarding the healthcare professional's performance of the procedure. In one or more embodiments, this real-time input includes video or image data captured of the healthcare professional during performance of the healthcare related procedure (e.g., via camera 104 or one or more additional cameras in the healthcare professional's environment. For example, in some implementations, the healthcare professional can wear a device (e.g., user device 102) having a camera (e.g., camera 104) during performance of the procedure that can capture video and/or image data from a perspective of the healthcare professional during performance of the procedure. For example, device worn by the user can include an eyewear device (e.g., an AR eyewear device, a HUD, or another hands free device. According to this example, the camera can stream or otherwise provide the captured image and/or video data to the server device 108 in real-time (e.g., as it is captured). In other implementations, the video/image data can be captured by one or more cameras located in the same room or environment of the healthcare professional that are aimed at the healthcare professional during performance of the procedure. These cameras can also stream or otherwise provide the captured image data to the AR assistance module 110 in real-time.

In addition to video/image feedback captured of the healthcare professional during performance of a healthcare related procedure, in other embodiments, the AR assistance module 110 can receive other forms of input that can be used to monitor and characterize various aspects of a procedure being performed by the healthcare professional. In some implementations, this additional feedback/input can include audio feedback, motion feedback and/or biometric feedback capture performance of the procedure by the healthcare professional. For example, the audio feedback can include audio recorded during the procedure, such as speech of the healthcare professional, the patient, and/or potentially other healthcare professionals involved in the procedure. In another example, the audio feedback can include audio generated by a machine or other computing system associated with the procedure (e.g., an alarm signal, a heartbeat sound produced by a heart-rate monitor, etc.). The motion feedback can include motion data generated from one or more motion sensors (e.g., accelerometers, gyroscopes, etc.) worn by the healthcare professional, the patient and/or other healthcare professionals involved in the procedure. For example, the motion feedback can provide information regarding position, orientation and movement of a user, including specific positions, orientations and movements of respective body parts of the user. In another example, the motion feedback can include information regarding pressure or force applied to a patient by the healthcare professional or medical instrument used by the healthcare professional (e.g., as captured via a motion sensor or pressure sensor). The motion feedback can also include motion data captured from a motion sensor associated with a medical device or instrument used during the procedure. For example, this type of motion feedback can include information regarding position, orientation and/or movement of the medical instrument relative to a patient's anatomy. The biometric feedback can include biometric sensor feedback regarding physiological responses of the healthcare professional, the patient and/or other healthcare professionals involved in the procedure. For example, the biometric feedback can include information regarding a user's vital signs (e.g., body temperature, pulse rate, respiration rate, blood pressure, etc.), stress levels, fatigue levels, attention levels, and the like. Such biometric feedback can be captured via one or more biometric sensors or biometric sensing devices worn by or otherwise physically coupled to the healthcare professional, the patient, and/or other healthcare professionals involved in the procedure.

In addition to the various types of visual, audio, motion and biometric feedback discussed above, in some implementations in which a medical related procedure involves usage of a device configured to capture or generate data (in addition to the cameras and motion or biometric sensors discussed above), the AR assistance module 110 can also receive this data as feedback. For example, in implementations in which the medical related procedure involves data entry by the healthcare professional into another computing system, the AR assistance module can also receive feedback from the other computing system regarding the data entry. For example, if the procedure involves entering patient information into a computing system, the AR assistance module 110 can receive or access this patient information as it is entered. In another example, if the procedure involves entering programming information into a computing system that controls a medical device involved in the procedure (e.g., an implantable medical device (IMD), a robotic device, an imaging device, a laser device, etc.), the AR assistance module 110 can receive or access this programming information as it is entered. In another example, if the procedure involves entering billing information (e.g., billing codes, procedure codes, insurance information, etc.) into a billing system, the AR assistance module 110 can receive this billing information as it is entered. In other implementations in which the medical related procedure involves usage of a medical device or instrument configured to capture or generate data during a procedure, the AR assistance module 110 can also receive this data as input. For example, the medical device or instrument can be configured to capture and/or measure physiological data associated with the patient using various sensors and provide this data to the AR assistance module. In another example, the medical device or instrument can include an imaging device used during a procedure that captures images of a patient's body (e.g., internal or external) during a medical procedure. For example, such imaging devices can include but are not limited to: radiography imaging devices, magnetic resonance imaging devices, nuclear imaging devices, ultrasound imaging devices, elastography imaging devices, tactile imaging devices, photoacoustic imaging devices, and the like. In another example, the AR assistance module 110 can receive image data captured from one or more cameras provided on or within medical instruments used during a procedure. For example, many invasive surgical devices such as probes, catheters, endoscopes, include imaging sensors that capture images of a patient's internal body during a surgical procedure to facilitate the procedure. Still in yet another example, the AR assistance module 110 can receive 2D and 3D imagining models of a patient's body or internal organs that are used and/or generated during a surgical procedure to facilitate the procedure.

In one or more embodiments, the procedure identification component 112 can be configured to analyze this visual, audio, motion, biometric, data entry and/or medical device generated input as it is received in real-time to identify and characterize various aspects of a procedure that occur in real-time. This can include the type of procedure and various specific characteristics of the procedure, such as the respective actions and events of the procedure and characteristics of these actions or events. For example, in association with monitoring a medical procedure, the procedure identification component 112 can identify the specific medical procedure being performed. The procedure characterization component 114 can further generate descriptive information that describes the respective actions/steps performed by the healthcare professional during the procedure based on the received input. For example, in one or more embodiments, the procedure characterization component 114 can identify actions or steps being performed by the healthcare professional and characteristics of those actions or steps. The characteristics can vary depending on the type of procedure being performed and the type of input/feedback received. In various implementations, the characteristics described by the procedure characterization component 114 can generally describe what the healthcare professional is doing, how the healthcare professional is doing it, what the healthcare professional is using or applying and how (e.g., drug and dosage), the state of a patient, system or instrument before performance of a procedural action or step, and the state of the patient, system or instrument after performance of the procedural action or step. For example, in some implementations, the characteristics can relate to the physical position/orientation or movement of the healthcare professional, a body part of the healthcare professional or an instrument operated by the healthcare professional, in association with performance of the procedural action/step. In another example, the characteristics can relate to a state, status, or appearance of systems and equipment used in a procedure. In another example, the characteristics can include a physiological response of the healthcare professional, the patient, and/or other healthcare professionals involved in the procedure. In some aspects, these physiological responses can indicate mental states of the healthcare professional throughout the procedure (e.g., focused, confused, fatigued, stressed, concerned, etc.).

For example, with respect to an IV cannulation procedure, based on visual, audio, motion, biometric, etc., input received during the procedure, the procedure identification component 112 can identify or determine that an IV cannulation procedure is being performed. The procedure characterization component 114 can further generate descriptive information regarding the steps/actions performed as they are performed, such as but not limited to: preparation of the IV site, preparation of the tubing and the fluid bag, application of the tourniquet, selection of the catheter, insertion of the catheter, removal of the tourniquet, attaching the tubing, and opening of the IV line. The procedure characterization component 114 can further provide detailed information about the respective actions/steps observed, such as for example: timing of the actions, order of the actions, instruments used, sizing of the instruments, location of the instruments, location of the IV site, positions of the healthcare professional hands, physiological responses of the patient, physiological responses of the healthcare professional (e.g., indicating stress, fatigue, etc.), pressure applied to the patient during insertion of the needle and tubing, dosage applied to the IV fluid, etc. It should be appreciated that the amount and type of the descriptive information will vary based on the type of procedure being performed and the type of input/feedback received by the AR assistance module during the procedure. Thus in summary, the procedure identification component 112 can be configured to analyze the various input discussed above to identify a specific procedure being performed and the procedure characterization component 114 can further generate descriptive information that describes or narrates the respective actions and events of the procedure as they occur.

In one or more embodiments, the AR assistance module 110 can be configured to monitor and assess a defined set of healthcare related procedures. These procedures can include medical procedures, clerical procedures and/or maintenance procedures. Each of the procedures can be associated with a unique identifier or code that identifies the specific procedure. The AR assistance module 110 can further access information (e.g., stored in memory 130, at one or more external information sources 138, or another device/system), that identifies the respective procedures the AR assistance module 110 is configured to monitor and evaluate. In some embodiments, prior to or during performance of a healthcare related procedure, the procedure identification component 112 can receive explicit information identifying the procedure being performed (e.g., the identifier for the procedure, the name of the procedure, etc.). This can be because the procedure is scheduled in the system. For example, each medical bay in a facility may have procedures defined for it during the day. Or a nurse's schedule may have set procedures for her to perform that day and in a specific order. And in some implementations, in association with beginning a medical related procedure, the healthcare professional can enter (e.g., via a suitable input mechanism) or otherwise provide, information to the user device 102 identifying the specific procedure being performed. The user device 102 can further provide this information to the AR assistance module 110.

In other embodiments, the procedure identification component 112 can determine the procedure being performed based on analysis of the received input data associated with performance of the procedure. For example, based on the received input (e.g., visual, audio, motion, biometric, data entry, medical device generated, etc.), the procedure characterization component 114 can generate one or more descriptive parameters regarding characteristics of the procedure observed (e.g., identified objects, people, words, actions or event, characteristics of those actions or events, etc.). The procedure identification component 112 can further determine the type of procedure being performed by comparing the one or more descriptive parameters with predefined information (e.g., in memory 130, at one or more external information sources 138, or at another device) that associates the one or more descriptive parameters (e.g., the identified objects, people, words, actions or event, characteristics of those actions or events, etc.) or patterns in the descriptive parameters with a defined type of procedure.

A data structure storing the procedure information may have this predefined information as trigger circumstances. A procedure may have four trigger circumstances like a certain image of a drug is captured in image data, or a certain type of medical instrument is found in image data, or a certain phrase is captured in audio data ("I'm going to be administering your prescription now"). Further, the data structure storing the procedure information may specific how many of the trigger circumstances need to be meet for the system to detect the procedure is underway. Thus, if the procedure identification component 112 detects one or more trigger circumstances as predefined information, a procedure may be detected on-the-fly.

For example, based on reception of image data including a healthcare professional preparing a patient's IV site, the procedure characterization component 114 can generate descriptive information that indicates "IV site preparation" is performed or "an image of a patients IV site" has been detected. The procedure identification component 112 can further determine that the healthcare professional is performing an IV cannulation procedure based on data associating the determined descriptive information with an IV cannulation procedure. In another example, based on reception of audio input from healthcare professional involved in a procedure stating "I'm preparing the IV site," the procedure characterization component 114 can determine and/or generate corresponding descriptive data corresponding to keywords identified in the audio signal (e.g., prepare, IV, and site). Based on these keyword descriptors, trigger circumstances, and information associating these keyword descriptors with an IV cannulation procedure, the procedure identification component 112 can determine the healthcare professional is performing an IV cannulation procedure.

In some embodiments in which the procedure identification component 112 does not receive direct or explicit information identifying a procedure being performed, in addition to the descriptive information generated by the procedure characterization component 114, the procedure identification component 112 can use contextual information to facilitate identifying a procedure being performed. This contextual information can relate to but is not limited to: a location associated with the procedure (e.g., a specific room, area, sector, etc., of a hospital), a role of a user performing the procedure (e.g., a doctor, a type of the doctor, a nurse, etc.), a time of day, and/or patient information regarding a patient involved in the procedure. For example, certain locations in a healthcare environment can be associated with one or more known procedures. Thus depending on where a user performing a procedure is located, the procedure identification component 112 can determine which process type is likely happening (e.g., operating room B is often where cardiac procedures are performed, floor 3 is generally where rehabilitation procedures are performed, etc.). Further, a healthcare professional's role or title can also limit the number and type of procedures the person is authorized to perform. Thus the procedure identification component 112 can limit detection of procedures performed by a certain healthcare professional to only those the healthcare professional is authorized to perform. Still in other embodiments, respective healthcare professionals can become associated with information indicating the procedures they are likely to perform (e.g., based on historical data regarding past performance of the respective healthcare professionals). The procedure identification component 112 can further limit detection of performance of a procedure by a particular healthcare professional based on those procedures the healthcare professional is likely to perform. In another example, various procedures can be associated with performance at different times of day or different days of the week. Thus in some implementations, the procedure identification component 112 can restrict identification of a certain procedure being performed based on the time of day or day of week. Still on other implementation in which a procedure involves a patient, the procedure identification component 112 can restrict detection of procedures associated with that patient based on those procedures which the patient is scheduled to receive and/or authorized to receive.

According to these embodiments, the AR assistance module 110 can include context component 118 to facilitate determining this contextual information, including but not limited to: a current location associated with the procedure, a role of a user performing the procedure, a time of day, and/or patient information regarding a patient involved in the procedure. For example, the context component 118 can determine an identify of a location of healthcare professional performing a procedure, a role of the healthcare professional, an identity of the healthcare professional, an identity of the patient, and a time of day/day of the week. The context component 118 can further access predefined information (e.g., stored in memory 130, at one or more external information sources 138, or another device), that associates certain procedures with one or more of: specific locations in a healthcare facility, specific times of day/day of week, specific healthcare professionals or healthcare professional roles, specific patients, and the like. The context component 118 can employ various known techniques to determine a current location of a user. For example, these techniques can be based on global positioning system (GPS) data associated with the user or a user device 102 employed by the user, triangulation based locating methods, radio frequency identification tag (RFID) detection methods, monitoring user movement using cameras, beacons, and/or motion sensors, movement information monitored for the user, and the like. The context component can also employ various mechanisms to determine identities of healthcare professionals and/or patients. For example, in some embodiments, the context component 118 can determine an identity of a user based on image data captured of the user and suitable facial recognition techniques. In other embodiments, the context component 118 can determine an identity of a user performing a procedure based in part on information associating the user with a certain device (e.g., user device 102) operated by the user and usage of that device by the user in association with performance of the procedure.

The procedure characterization component 114 can further generate descriptive information that describes various aspects of a procedure over the course of the procedure. In one or more embodiments, in addition to facilitating identifying a procedure being performed, this descriptive information can be used by the procedure assessment component 116 to evaluate the performance of the procedure in real-time over the course of the procedure. As noted above, the descriptive parameters identified and/or generated by the procedure characterization component 114 can describe various aspects of a procedure being performed, including respective actions and events of the procedure and characteristics of those actions or events. For example, descriptive information generated by the procedure characterization component over the course of procedure can include but is not limited to: objects associated with a procedures or procedural environment, features of the objects, people associated with a procedure or procedural environment, features of the people, procedural actions/steps performed, characteristics of the procedural actions or steps, physical actions/motions performed by a user or an instrument, changes in appearance of a user or instrument, words spoken, sounds detected, physiological responses, and the like.

The mechanisms via which the procedure characterization component 114 generates descriptive parameters for a procedural environment and/or a procedure being performed by a healthcare professional can vary based on the type of received input. For example, regarding video and/or still image data captured of a procedural environment and/or of healthcare professional performing a procedure, in one or more embodiments, the procedure characterization component 114 can use various image recognition algorithms to identify objects in the image data (including people/faces), and features of the objects (e.g., color, size, brand, relative location, orientation, etc.). In addition, by analyzing a sequence or series of images (e.g., video data), the procedure characterization component 114 can identify actions, motions, behaviors and facial expressions represented by the image data. Image recognition algorithms rely on matching, learning, or pattern recognition algorithms using appearance-based or feature-based techniques. Common techniques include edges, gradients, histogram of oriented gradients (HOG), haar wavelets, and linear binary patterns. In various embodiments, the procedure characterization component 114 can generate information identifying objects, people, facial expressions, actions, behaviors, motions, etc., appearing in image data using a variety of models, including but not limited to: extracted features and boosted learning algorithms, bag-of-words models with features such as speeded-up robust features (SURF) and maximally stable extremal regions (MSER), gradient-based and derivative-based matching approaches, Viola-Jones algorithm, template matching, and image segmentation and blob analysis.

Regarding audio feedback, the procedure characterization component 114 can used pattern recognition techniques to identify unique characteristics in an audio signal. Based on the unique characteristics, the procedure characterization component 114 can identify distinct words or sounds and generate descriptive information identifying the words or sounds. Regarding motion data received from motion sensors worn by the healthcare professional, the patient, or another individual involved in the procedure, the procedure characterization component 114 can identify patterns in the motion data that correspond to known movements or gestures. For example, the procedure characterization component 114 can determine if a user is moving a certain body part and how, if the user is walking, standing, sitting, etc. Likewise, based on motion sensor data regarding motion of tool or instrument, the procedure characterization component 114 can determine relative positions and orientations of the instrument (e.g., relative to the patient, the person operating the instrument, etc.), and movements of the instrument. The procedure characterization component 114 can further generate descriptive information defining the movements of a user and an instrument throughout a procedure. The procedure characterization component 114 can also generate descriptive information that corresponds to input received from pressure sensors, biometric devices and other computing devices. For example, in response to reception of physiological information from a biometric device worn by a user (e.g., the healthcare professional, the patient, other healthcare professionals, etc.) during a procedure, the descriptor generator component 114 can generate descriptive data that identifies the physiological information (e.g., heart rate, vital signs, etc.). In another example, in response to entry of data into an associated compute system regarding a drug dosage to apply to a patient, the procedure characterization component 114 can generate descriptive information identifying the event, the drug, and the specific dosage.

In various embodiments, the procedure characterization component 114 can generate descriptive information describing an aspect of a procedure being performed based on a combination of observed objects, persons, motions, physiological responses, and the like. For example, using various machine learning techniques, patterns in various combinations of such data can be learned which equate to defined procedural events. In particular, many procedural events can be characterized by a combination of several descriptors, such as a sequence of motions involving a certain body part or instrument followed by a defined physiological response in the patient, and ending with position of the instrument or body part at a defined position/location.

Machine learning is a type of artificial intelligence (AI) that provides computers with the ability to learn without being explicitly programmed Machine learning focuses on the development of computer programs (e.g., the procedure identification component 112, the procedure characterization component 114, and the procedure assessment component 116) that can change when exposed to new data. Machine learning techniques use that compiled data to detect patterns in the data and adjust program actions accordingly. Machine learning algorithms are often categorized as being supervised or unsupervised. Supervised algorithms can apply what has been learned in the past to new data. Unsupervised algorithms can draw inferences from datasets. Deep learning is an aspect of AI that is concerned with emulating the learning approach that human beings use to gain certain types of knowledge. At its simplest, deep learning can be thought of as a way to automate predictive analytics. While traditional machine learning algorithms are linear, deep learning algorithms are stacked in a hierarchy of increasing complexity and abstraction. Each algorithm in the hierarchy applies a non-linear transformation on its input and uses what it learns to create a statistical model as output. Iterations continue until the output has reached an acceptable level of accuracy. The number of processing layers through which data must pass is what inspired the label "deep."

Thus in one or more embodiments, using one or more machine learning or deep learning techniques evaluating feedback data (e.g., visual data, motion data, audible data, biometric data, medical device generated data, etc.) received for many performances (e.g., by the same user or different users) of the same procedure over time, patterns in the feedback data can be identified which correlate to defined steps or actions of the procedure and characteristic of those steps and actions. This can be repeated for every procedure the AR assistance module 110 may potentially evaluate. For each procedure, reference pattern information can thus be developed that associates combinations and/or patterns in image descriptors, audio descriptors, motion descriptors, physiological descriptors, and the like, with defined procedural events or actions and characteristics of the actions or events for the procedure. The procedure characterization component 114 can access this reference pattern information (e.g., stored in memory, at one or more external information source, or at another device), to identify patterns in currently received feedback data (e.g., visual data, motion data, audible data, biometric data, medical device generated data, etc.) during performance of a procedure by a healthcare professional to identifying corresponding reference patterns and associated procedural actions and/or characteristics of those actions.

In one or more embodiments, the procedure assessment component 116 can be configured to assess or evaluate a procedure being performed in real-time based on the descriptive information generated/determined by the procedure characterization component 114. In particular, the AR assistance module 110 can be configured to evaluate a set of known medical related procedures. Each of these procedures can have defined guidelines or protocols that define a desired manner for performing the procedure. These guidelines/protocols can be defined by the healthcare organization and/or government mandated. In some implementations, these guidelines and protocols can be optimized over time using various machine learning techniques and data monitored for repeated or similar procedures (as discussed infra with reference to optimization component 604). Information identifying the respective procedures and the guidelines/protocols for the respective procedures can be included in memory 130 (e.g., as procedure guideline/protocol information 132), at one or more external information sources 138, or another source accessible to the AR assistance module. The guideline/protocol information for each procedure can include reference descriptive parameters that describe various aspects of the procedure, including but not limited to: required steps or actions for a procedure and timing for the respective steps or actions, including an order of for performance of the respective actions. The procedure guideline/ protocol information 132 can also include reference descriptive parameters that define characteristics of the required steps or actions, such as but not limited to descriptive parameters related to: how the respective actions/steps should be performed, what supplies/instruments should be used, how to dispose of supplies, how to interact with a patient and/or other healthcare professionals during a procedure and the like. In another example, the guideline/protocol information can include descriptive parameters regarding responsive actions/steps to be taken when various potential events, reactions, or complications arise during a procedure.

In various embodiments, during performance of a procedure by a healthcare professional, the procedure assessment component 116 can be configured to compare the descriptive parameters characterizing various aspects of the procedure generated by the procedure characterization component 114 with the reference descriptive parameters included in defined guidelines/protocols for the procedure. Based on the comparison, the procedure assessment component 116 can determine what steps or actions included in the defined procedure guidelines/protocols the healthcare professional is currently performing. The procedure assessment component 116 can further determine how the healthcare professional is performing various aspects of the procedure relative to the defined guidelines/protocols for the procedure. In particular, in one or more embodiments, the procedure assessment component 116 can determine if and when the healthcare professional is deviating from the defined guidelines/protocols for the procedure or otherwise performing an aspect of the procedure incorrectly (e.g., against the defined guidelines and protocols for the procedure). The procedure assessment component 116 can also identify the specific aspect of the procedure the healthcare professional is performing incorrectly.

For example, based on comparison of descriptive information generated by the procedure characterization component 114 regarding steps/actions of the procedure that are performed and with reference descriptive information for the procedure, the procedure assessment component 116 can determine if the healthcare professional performed the step/action out of order, if the healthcare professional is performing a step or action too slow or too fast, if the healthcare professional skipped a step or action, if the healthcare performed an unnecessary step or action, and the like. In another example, with respect to a specific action or step of the procedure, the procedure assessment component 116 can compare information generated by the procedure characterization component 114 describing one or more characteristic of the specific action or step being performed by the healthcare professional with reference information defining required characteristics for the procedural action. Based on the comparison, the procedure assessment component 116 can determine if the healthcare professional's performance of the procedural action is on par with the required characteristics for the procedural action. For example, with respect to a specific step of a surgical procedure, the procedure assessment component can determine if the healthcare professional is positioned correctly relative to the patient, if the healthcare professional is operating on the correct side and/or body part of the patient, if the healthcare professional is using the correct instruments, if the patient's vital signs are appropriate for the step, if the healthcare professional's level of fatigue is acceptable, and the like. In addition to determining if and how a healthcare professional has performed or is performing an aspect of a procedure incorrectly, in various embodiments, the procedure assessment component 116 can also determine if and when a healthcare professional has performed or is performing an aspect of a procedure correctly.

In some embodiments, the procedure assessment component 116 can further tailor its evaluation of a healthcare professional's performance of a procedure based on a particular context of the procedure. For example, the manner in which certain medical procedures are performed are often tailored to the patient based on the condition of the patient, the physical health of the patient, health records of the patient, the severity of the ailment of the patient, the sensitivity of the patient, the preferences of the patient, the age of the patient, the allergies of the patient, the mental stability of the patient, and the like. Such conditional factors can affect the particular actions/steps of a procedure that are performed, the manner in which they are performed, the pharmaceuticals that are applied, the dosage of the pharmaceuticals and the like. In some implementations, prior to performing a procedure, a clinician can determine and provide information regarding various aspects of a procedure that have been tailored to a particular patient. This information can be made accessible to the procedure assessment component (e.g., at one or more external information sources 138 or another device). In another example, the manner in which certain medical procedures are performed can depend on the equipment and supplies that are available. Thus in various embodiments, the context component 118 can determine such contextual information regarding a patient associated with a procedure, the equipment/supplies available, and the environment of the procedure (e.g., by identifying the relevant contextual information in one or more external information sources 138). The procedure assessment component 116 can further tailor evaluation of the procedure based on such contextual information.

In some embodiments, in addition to generating descriptive information that narrates a procedure being performed, the procedure characterization component 114 can further evaluate an environment in which the procedure is occurring or will occur to characterize the environment. For example, using image data captured from the environment, the procedure characterization component 114 can identify the objects in the environment, as well as the state or status of the objects, including medical instruments, supplies and devices (e.g., on/off, used/unused, working properly/improperly, etc.), and the relative positions of the objects. The procedure characterization component 114 can also access information (e.g., stored in memory 130, at an external information sources 138, or another device), that provides information regarding the state or status of the objects. Based on information describing the procedure environment, the procedure assessment component 116 can make determinations regarding whether the environment is properly prepared and equip for performance of the procedure in accordance with predetermined quality control standards. The procedure assessment component 116 can further assess the procedural environment at various points throughout the procedure and upon completion of the procedure to determine whether all instruments, supplies, equipment and personnel that should be present are present, whether the instruments, supplies, equipment and personnel are in the correct positions, and whether the instruments, supplies, equipment and personnel are in the correct state/status.

According to these embodiments, the procedure guideline/protocol information 132 can also include reference information identifying requirements for the procedural environment at various points throughout the procedure, such as but not limited to: what equipment and supplies should be included in the environment, status/state of the equipment/supplies at various points throughout the procedure (e.g., on/off, operating properly/improperly, used/unused, etc.), relative positions of the equipment and supplies at various points throughout the procedure (e.g., external to patient, in patient, in sanitation bag, in trash unit, etc., what people that should be located in the procedural environment, where and/when, how those people should appear (e.g., what they should be wearing), etc. Based on information determined by the procedure characterization component regarding the procedural environment, the procedure assessment component 116 can further assess the procedural environment prior to beginning the procedure, at various points throughout the procedure, and upon completion of the procedure, to determine whether the procedural environment is on par with the required guidelines. For example, the procedure assessment component 116 can determine if certain supplies or equipment is missing from the procedure environment, if certain supplies or equipment is functioning improperly, if supplies/tools were unused when they should have been, whether certain supplies/tools that were used were not disposed correctly (e.g., a sponge was left in the patient), and the like. In another example, the procedure assessment component 116 can determine if a healthcare professional gets the wrong supplies/equipment out for the surgery.

The feedback component 120 can be configured to determine and/or generate feedback information in real-time in response to determinations made by the procedure assessment component 116 regarding performance of a procedure by a healthcare professional and/or the procedural environment. The feedback component 120 can further provide this feedback to a healthcare professional that is performing a procedure, a user supervising performance of the procedure, or another entity (e.g., a remote monitoring system/service, an administrative personnel, etc.). Based on received during performance of a procedure feedback regarding an aspect of a procedure a healthcare profession has performed or is currently performing incorrectly, the healthcare professional can take appropriate action to correct the mistake immediately, thereby minimizing potential complications of the mistake down the road. This has a strong benefit to patients, payors, practitioners, clinicians, governments, and healthcare systems in general. Any reduction in mistakes can save lives and reduce cost.

In one or more embodiments, the feedback component 120 can include correction component 122 to determine and/or generate corrective feedback regarding an aspect of a procedure that has been or is being performed incorrectly and/or an aspect of a procedure environment that is improper. For example, based on a determination by the procedure assessment component 116 that a healthcare professional has skipped a procedural step or action, the correction component 122 can determine or generate information that identifies the skipped step or action and informs the healthcare professional regarding the skipped step or action. In another example, based on a determination by the procedure assessment component 116 that a healthcare professional is performing an unnecessary step or action, the correction component 122 can determine or generate information that identifies the unnecessary step or action and informs the healthcare professional regarding the unnecessary step or action. In another example, based on a determination by the procedure assessment component 116 that a healthcare professional is performing a step or action out of order, the correction component 122 can determine or generate information that identifies the step or action performed in the incorrect order. The information can further describe the correct order for the step. For example, the information can identify one or more steps or actions that should be performed prior to the step or action the healthcare professional is initiating or currently performing.

In another example, based on a determination by the procedure assessment component 116 that a healthcare professional has performed or is performing a step or action incorrectly, the correction component 122 can determine or generate information that identifies the step or action. In some embodiments, correction component 122 can further determine or generate information regarding the specific aspect of the step or action that is incorrect. The correction component 122 can also determine or generate information regarding how to correct the error. For example, the correction component 122 can retrieve the reference information associated with the particular step or action in a reference data structure that defines how the step or action, or the specific aspect of the step or action, should be performed. The data structure for the procedure may have text, video, images, and audio stored with respect to each step or action in a procedure. These all may be used in assisting the healthcare professional through an AR interface.

Regarding an identified error with respect to the procedural environment, the correction component 122 can determine and/or generate information that identifies the aspect of the procedure environment that does not comply with the defined guidelines/requirements for the procedure. For example, based on a determination that a particular instrument needed for a procedure is missing from the procedural environment, the correction component 122 can determine and/or generate information indicating the missing instrument. In another example, based on a determination that a sponge used during a surgical procedure has not been removed from the patient upon initiation of closing up the patient's surgical site, the correction component 122 can determine and/or generate information indicating the incorrect position and/or disposal of the sponge. In another example, based on a determination that an assisting nurse is located near a patient's feet at a time during a procedure when she is needed to be located near the patient's heat to assist a primary healthcare professional with a step of a procedure, the correction component 122 can determine and/or generate information indicating the incorrect position of the nurse and identifying the correct position. In another example, based on a determination that a healthcare professional gets the wrong supplies/equipment out for the surgery, the correction component can generate corrective feedback indicating the wrong supplies/equipment have been selected and provide the healthcare professional with feedback indicating the wrong supplies/equipment and instructing the healthcare professional get the right supplies/equipment out so as not to open and waste supplies/equipment that aren't needed.

The feedback component 120 can also include praise component 124 to determine and/or generate praise information regarding one or more aspects of a procedure a healthcare professional is performing or has performed correctly. For example, over the course of a procedure, if the procedure assessment component 116 determines that the healthcare professional performed an action or step of the procedure correctly, the praise component 124 can generate information identifying the step or action that was performed correctly.

The feedback component 120 can also include guidance component 126 to facilitate providing a healthcare professional with guidance information that guide the healthcare professional throughout a procedure. For example, this guidance information can inform a healthcare professional regarding how to perform each step of a procedure and when. Such information can be useful to train healthcare professionals how to perform new procedures and/or to guide a healthcare professional that needs or desires such step by step assistance. For example, in some embodiments, the guidance component 126 can retrieve reference guideline/protocol information for a procedure that is being performed. The reference guideline/protocol information can defines how to perform the procedure, including how to perform each step or action of the procedure, when to perform each step or action, and the characteristics of the respective steps or actions. The guidance component 126 can further provide the healthcare professional with information for each step at the time when the step is to be performed, generating a live step by step tutorial explaining how to perform each step of the procedure. In some embodiments, the guidance component 126 can determine what information to provide the healthcare professional at various points based on information determined by the procedure assessment component 116 regarding when certain steps or actions are completed or initiated by the healthcare professional. For example, with respect to a procedure including 10 steps, based on information determined by the procedure assessment component 116 that the healthcare professional has completed step 1 and/or is initiating step 2, the guidance component 126 can determine or retrieve information describing how to perform step 2 and provide this information to the healthcare professional at this time.

Figure 6:
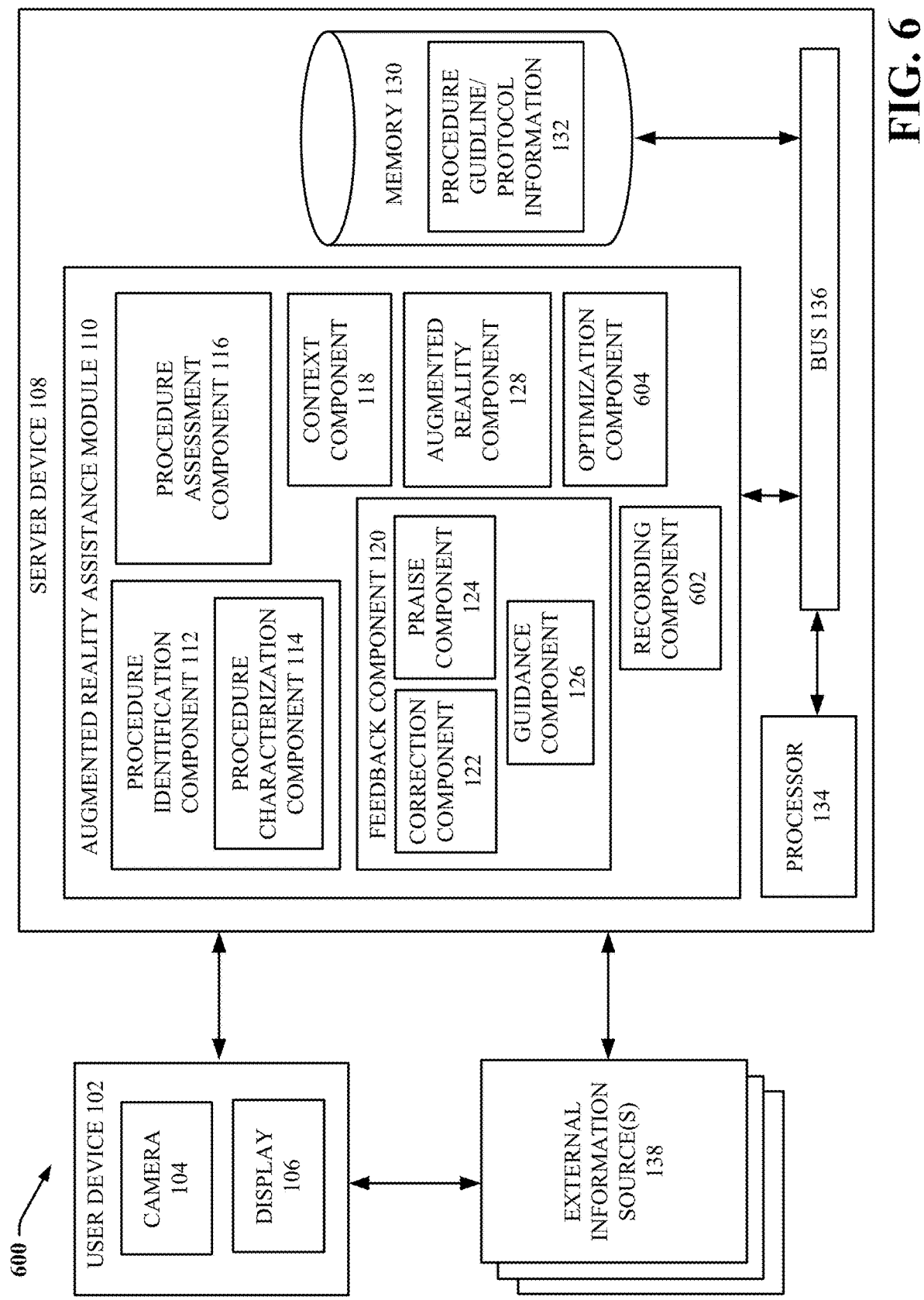
FIG. 6 illustrates a block diagram of an example system that facilitates providing auxiliary information regarding healthcare procedure performance using AR in accordance with one or more embodiments described herein.

Further in some embodiments, the feedback component 120 can access past performance information (e.g., stored in memory 130, at one or more external information sources 138, or another device) recorded for the healthcare professional regarding the healthcare professional's past performance of the same procedure that is currently being performed by the healthcare professional (e.g., via recording component 602 discussed infra with reference to FIG. 6). For example, each time the healthcare professional's performance of a particular procedure is evaluated by the AR assistance module 110, the AR assistance module (e.g., via recording component 602) can generate report information that documents the information determined and/or generated by the procedure identification component 112, the procedure assessment component 116 and/or the feedback component 120 regarding the healthcare professionals performance, such as information regarding what steps/actions were performed correctly and incorrectly, what aspects of those actions were performed correctly or incorrectly, duration of performance of the respective steps, and the like. The feedback component 120 can further compare past performance information with current performance information to determine, in real-time, how the healthcare professional is performing respective steps of a procedure relative to past performance of the same steps. The feedback component 120 can further determine and provide the healthcare professional with information that indicates how a healthcare professional's current performance of a procedural step compares with her past performance of the same step. For example, with respect to a surgical procedure that involves 10 procedural steps, the feedback component 120 can access past performance information indicating the success rate for performance of each step. For example, such information may indicate that the healthcare professional performs steps 1-5 correctly 90% of the time, yet performs step 6 incorrectly 50% of the time. Thus when the healthcare professional reaches step 6 during a current performance of the procedure, if the procedure assessment component 116 determines that the healthcare professional performs step 6 incorrectly, the correction component 122 can determine and/or generate information regarding the incorrect performance of step 6. The correction component 122 can also generate feedback information indicating the 50% success rate of step 6 in the past, and the degree to which her success rate for step 6 has decreased based on the current error. Alternatively, if the procedure assessment component 116 determines that the healthcare professional performs step 6 correctly, the praise component 124 can generate and provide information to the healthcare professional regarding the correct performance and the improvement to her success rate for step 6.

Further, in some embodiments, the guidance component 126 can be configured to automatically generate and provide guidance information regarding how to perform certain steps of a procedure based on past performance information for those steps. For example, based on past performance information indicating that this healthcare professional regularly performs step 6 incorrectly, when the healthcare professional reaches step 6 during the procedure, the guidance component 126 can generate/provide the healthcare professional with guideline information describing how to perform step 6 correctly.

The manner in which the feedback component 120 provides feedback to a healthcare professional (or other individual/entity) in association with performance of a healthcare procedure can vary. However, in various exemplary embodiments, the AR assistance module 110 can include AR component 128 to facilitate providing feedback determined/generated by the feedback component 120 to a healthcare professional using AR visioning techniques. According to these embodiments, the AR component 128 can be configured to generate overlay data comprising or otherwise representing the feedback information determined/generated by the feedback component 120. For example, the overlay data can include text, an image, a video, a symbol, a marker, an icon, a hyperlink or other suitable visual data object that can be projected onto a display that views or includes a visualization of the healthcare professional's environment from the perspective of the healthcare professional. For example, in various embodiments, the user device 102 includes a AR device that is worn by the healthcare professional during performance of the procedure. In some embodiments, the display 106 of the user device 102 can include a transparent display through which the healthcare professional views the environment. In another example, the display 106 can present a live video or image of the healthcare professional's environment. Regardless of the type of display, the overlay data can be configured for rendering on the display over or within a view of the environment.

In some embodiments, the overlay data can be spatially aligned with one or more objects included in the environment and viewed on or through the display. For example, if a healthcare professional prepares an incision site incorrectly, the overlay data can be rendered spatially on or near the incision site. According to these embodiments, the AR component 128 can determine the object to spatially align the overlay data with based on the feedback information and/or the specific aspect of the procedure for which the overlay data is based. The AR component 128 can further provide the user device 102 (or the device at which the overlay data is to be displayed), with the overlay information and information identifying the object to spatially align the overlay data with. The user device 102 can further be configured to render the overlay data relative to the object included in the display accordingly.

For example, in some embodiments, the feedback information generated by the feedback component 120 can be determined or selected from a set of defined feedback options for each procedure. According to these embodiments, each feedback option can be associated with information (e.g., included in memory 130, at one or more external information sources 138, or at another) identifying an object or objects for association with overlay information. The AR component 128 can thus determine the object to spatially align the overlay data with based on previously determined information associating the feedback information with the object. In another embodiment, the AR component 128 can identify key words or terms associated with the feedback information that the overlay data includes or represents. For example, the feedback information can indicate that the "incision site is incorrectly prepared." With theses implementations, based on recognition of the key word "incision site," the AR component 128 can determine the object to associate the overlay data with is the incision site. In some implementations of this embodiment, the AR component 128 can also employ index information (e.g., stored in memory, at one or more external information sources 138, or another device), that associates previously determined key terms that may potentially be included in feedback information determined or generated by the feedback component 120 with objects. In some embodiments, each procedure can be associated with an index tailored to that procedure that includes key terms and associated objects relevant to that procedure. In some implementations, the index can further include hierarchy information that indicates what key term and/or associated object to select when two or more key terms are included in feedback information to be represented by the overlay data. For example, if feedback information indicates that "the location of the physician's instrument relative to the incision site is incorrect," the AR component 128 can recognize both the terms "instrument" and "incision site." The hierarchy information however can indicate the term "instrument" receives priority over the term "incision site" and the AR component 128 can select the incision site over the instrument as the object for associating the overlay data.

In some embodiments in which the overlay data can be interacted with. For example, in embodiments in which the overlay data includes a video, the video can be selected for playback via the display 106. For instance, the video can include a visual demonstration regarding how to perform a particular aspect of a procedure. According to this example, the healthcare professional can stop his or her performance of a procedure to watch the provided video prior to continuing with the procedure. In another example, in which the overlay data includes a hyperlink, the healthcare professional can select the hyperlink to retrieve the information associated with the hyperlink.

Figure 2:
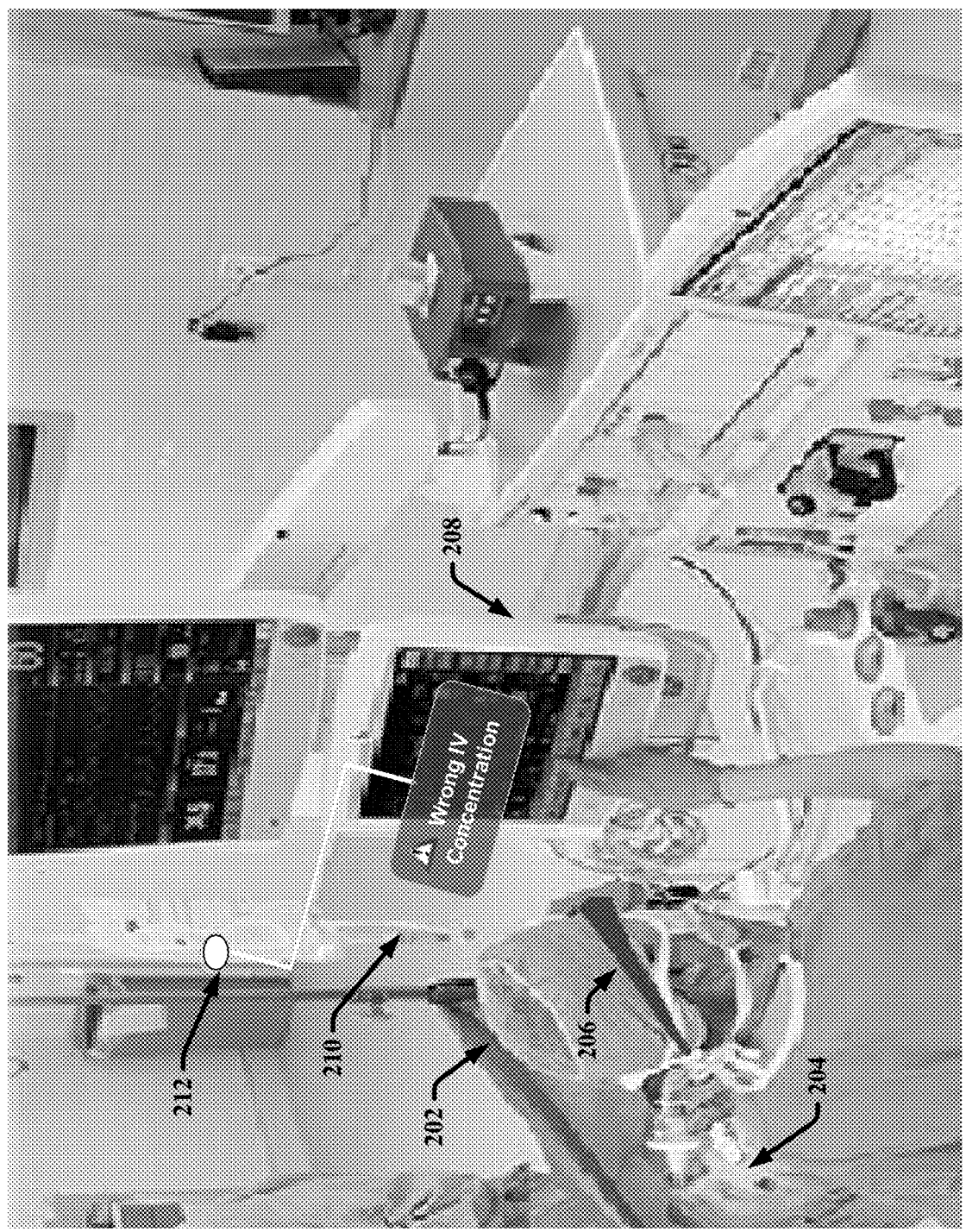
FIGS. 2-4 present example AR visualizations including auxiliary information presented to a clinician regarding current performance of a healthcare procedure by the clinician in accordance with one or more embodiments described herein.
Figure 3:
Figure 4:

FIGS. 2-4 present example AR visualizations including auxiliary information presented to a clinician regarding current performance of a healthcare procedure by the clinician in accordance with one or more embodiments described herein. One or more aspects of the example AR visualizations demonstrate the features and functionalities of system 100 (and additional systems described herein).

With reference to FIGS. 1 and 2, visualization 200 depicts a clinician 202 performing a medical procedure on a patient 204. In order to facilitate performance of the medical procedure by the clinician 202, the clinician is wearing an AR device 206 that includes a transparent display (not shown) through which the clinician 202 can view his environment clearly (e.g., display 106). In various embodiments, the AR device 206 can be or include user device 102. Further, the AR device 206 can include or be communicatively coupled to the AR assistance module 110 to facilitate monitoring the performance of the procedure by the clinician 202 in real-time and providing the clinician 202 with overlay data that guides or assists the clinician 202 with performing the procedure.

In the embodiment shown, the clinician 202 is currently performing an action of the medical procedure that includes entering IV information into a computing system 208 that controls concentration of IV fluid supplied to the patient 204. Based on feedback received by the AR assistance module 110 and patient information indicating the proper IV concentration for the patient, the AR assistance module 110 has determined that the clinician 202 has entered the wrong IV concentration for the patient 204. In one or more embodiments, the feedback can include image data captured of the clinician entering the incorrect IV concentration. For example, the image data can include (e.g., video and/or still images) captured via a camera on the AR device 206 (not shown) with a field of view that corresponds or substantially corresponds to that of the clinician (e.g., with camera 104). In another implementation, the image data can be captured via another camera in the operating room. In other embodiments, the feedback can include the actual concentration information data entered into the computing system 208 by the clinician.

As a result of the detected error, the AR assistance module 110 has generated overlay data including feedback regarding the wrong IV concentration. The overlay data is further rendered on the display (not shown) of the AR device 206 so that it is seen by the clinician overlaid onto the current view of the procedural environment viewed through the display. For example, in accordance with visualization 200, this current view includes at least the touch screen of the computing system 208 via which the clinician is entering information and the IV bag. The overlay data includes a semi-transparent pop-up display window 210 with text and a warning symbol indicating the error of entering the wrong IV concentration. The overlay data also includes a line connecting the display window 210 to the actual IV bag, which is highlighted with additional coloration data 212 that draws attention to the IV bag. In an aspect, the coloration data 212 can be a bright color (e.g., red, yellow) or flash such that the clinician's attention is drawn to the IV bag. In one or more implementations, the overlay data can remain in the clinician's view until the error is corrected, at which time it is dismissed. For example, based on a determination by the AR assistance module 110 that the clinician has entered the correct IV concentration information, the AR assistance module 110 can provide a message to the user device 102 instructing the user device to remove the overlay data from the display.

It should be appreciated that the appearance and location of the overlay data (e.g., the display window 210 and the coloration data 212) is merely exemplary and intended to convey the concept of what is actually viewed by the clinician 202 through the AR device 206. However, the appearance and location of the overlay data in visualization 200 is not technically accurate, as the actual location of the overlay data would be on the glass/display of the AR device 206 which is not visible given the position of the clinician in the image.

With reference to FIGS. 1 and 3, visualization 300 depicts another clinician 302 performing a medical procedure on a patient 304. In order to facilitate performance of the medical procedure by the clinician 202, the clinician is wearing an AR device 306 that includes a transparent display (not shown) through which the clinician 302 can view her environment clearly (e.g., display 106). In various embodiments, the AR device 306 can be or include user device 102. Further, the AR device 306 can include or be communicatively coupled to the AR assistance module 110 to facilitate monitoring the performance of the procedure by the clinician 302 in real-time and providing the clinician 302 with overlay data that guides or assists the clinician 302 with performing the procedure.

In the embodiment shown, the clinician 302 is currently operating on the patient 304. Based on feedback received by the AR assistance module 110 and information regarding the medical supplies that should be accessible to the clinician 302 at this stage of the procedure, the AR assistance module 110 has determined that a 12 gauge needle is missing from the supply table. In one or more embodiments, the feedback can include image data captured of the procedural environment via a camera on the AR device 306 (not shown) with a field of view that corresponds or substantially corresponds to that of the clinician (e.g., with camera 104). In another implementation, the image data can be captured via another camera in the operating room. As a result of the detected error, the AR assistance module 110 has generated overlay data including feedback regarding the missing 12 gauge needle. The overlay data is further rendered on the display (not shown) of the AR device 306 so that it is seen by the clinician 302 overlaid onto the current view of the procedural environment viewed through the display. For example, in accordance with visualization 300, this current view includes at least the operating area of the patient (e.g., the patient's stomach), a portion of the assisting clinician and the supply table. The overlay data includes a semi-transparent pop-up display window 308 with text and a warning symbol indicating missing 12 gauge supply needle. The overlay data also includes a line connecting the display window 308 to a graphical image 310 of a 12 gauge supply needle that is overlaid onto the table to draw the clinician's attention to the supply table and the missing needle.

It should be appreciated that the appearance and location of the overlay data (e.g., the display window 308 and the graphical image 310) is merely exemplary and intended to convey the concept of what is actually viewed by the clinician 302 through the AR device 306. However, the appearance and location of the overlay data in visualization 300 is not technically accurate, as the actual location of the overlay data would be on the glass/display of the AR device 306 which is not visible given the position of the clinician in the image.

With reference to FIGS. 1 and 4, visualization 400 depicts another clinician 402 performing a medical procedure on a patient 404. In order to facilitate performance of the medical procedure by the clinician 402, the clinician is wearing an AR device 406 that includes a transparent display through which the clinician 402 can view his environment clearly (e.g., display 106). In various embodiments, the AR device 406 can be or include user device 102. Further, the AR device 406 can include or be communicatively coupled to the AR assistance module 110 to facilitate monitoring the performance of the procedure by the clinician 402 in real-time and providing the clinician 302 with overlay data that guides or assists the clinician 402 with performing the procedure.

In the embodiment shown, the clinician 402 is currently operating on the patient 404. Based on feedback received by the AR assistance module 110 and information regarding the defined steps of the medical procedure, the AR assistance module 110 has determined that the clinician is inserting the catheter instrument without having properly prepared the incision site. In one or more embodiments, the feedback can include image data captured of the procedural environment via a camera on the AR device 406 (not shown) with a field of view that corresponds or substantially corresponds to that of the clinician (e.g., with camera 104). In another implementation, the image data can be captured via another camera in the operating room. In another implementation, the feedback can be based on motion data captured via one or more motion sensors worn by the clinician 402 and/or attached to the catheter instrument. As a result of the detected error, the AR assistance module 110 has generated overlay data including feedback regarding the failure to prepare the incision site before performing the insertion step. The overlay data is further rendered on the display (not shown) of the AR device 406 so that it is seen by the clinician 402 overlaid onto the current view of the procedural environment viewed through the display. For example, in accordance with visualization 400, this current view includes at least the operating area of the patient 404. The overlay data includes a semi-transparent pop-up display window 408 with text and a warning symbol instructing the clinician to stop and prepare the incision site before insertion.

Again, it should be appreciated that the appearance and location of the overlay data (e.g., the display window 410) is merely exemplary and intended to convey the concept of what is actually viewed by the clinician 402 through the AR device 406. However, the appearance and location of the overlay data in visualization 400 is not technically accurate, as the actual location of the overlay data would be on the glass/display of the AR device 406.

Figure 5:
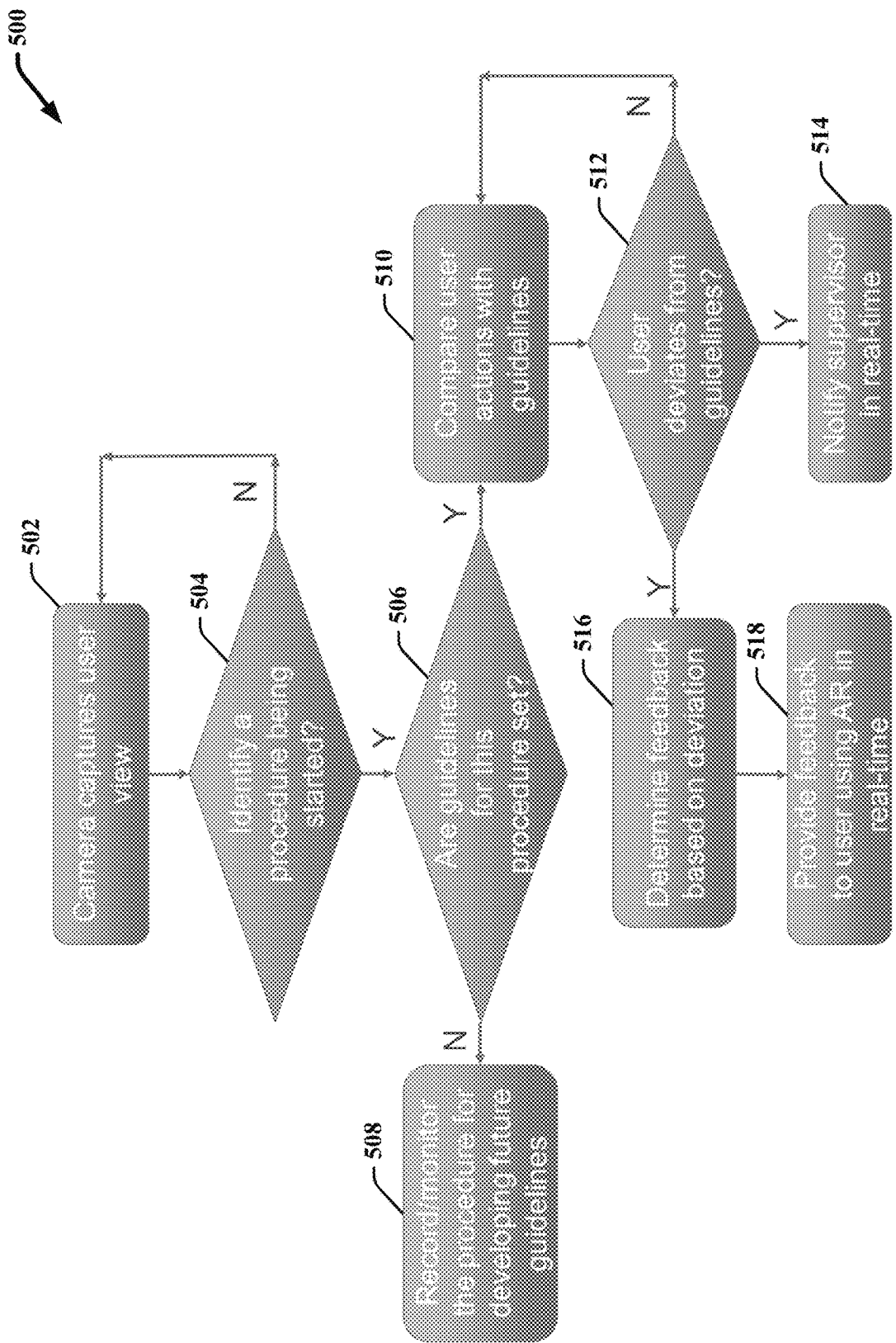
FIG. 5 provides a flow diagram of an example method for providing auxiliary information regarding healthcare procedure performance using AR in accordance with one or more embodiments described herein.

FIG. 5 provides a flow diagram of an example method 500 for providing auxiliary information regarding healthcare procedure performance in real-time using AR in accordance with one or more embodiments described herein. In various embodiments, method 500 can be performed by system 100 and the like using user device 102, server device 108 and/or one or more external information sources 138. In one implementation of method 500, a user (i.e., a healthcare professional) working in a healthcare environment wears an AR device (e.g., user device 102) throughout the workday. For example, the AR device can include an eyewear device (e.g., a HUD, glasses, goggles, or the like) that allows the user to see the environment through a transparent display (e.g., display 106). The eyewear device can also include a camera (e.g., camera 104), that captures video and/or still images of the user's environment from the perspective of the user. In other implementations, one or more cameras can be positioned at various locations throughout the user's environment and capture image data (e.g., video and/or still images) of the user as the user goes about his or her workday.

With reference to FIGS. 1 and 5, at 502, a camera captures a current view of the user. For example, the camera can capture a video of the user's environment from the user's perspective. In accordance with system 100, the video data can be provided to AR assistance module 110 in real-time (e.g., streamed as it is captured) for processing by the AR assistance module 110. At 504, the video data is analyzed to determine whether it appears the user is performing a procedure or starting performance of a procedure (e.g., via procedure identification component 112). If the procedure identification component 112 determines that a procedure is not being started, the AR assistance module 110 can continue to analyze new video data as it is received until it determines the user is starting a procedure. At 506, based on a determination that the user has started a procedure, the AR assistance module determines whether guidelines are set for the procedure (e.g., via procedure assessment component 116).

In some embodiments, if guidelines are not set for the procedure, at 508 the AR assistance module 110 (e.g., via the procedure characterization component 114, the procedure assessment component 116, and/or the recording component 602), can record/monitor the procedure being performed to facilitate developing future guidelines for the procedure. For example, procedure characterization component 114 and/or the procedure assessment component 116 can determine descriptive information for the procedure regarding the various actions or steps performed and the characteristics of those actions or steps. The descriptive information generated for the procedure can be stored (e.g., in memory 130, at one or more external information sources 138, or another device) to facilitate evaluating the procedure to develop guidelines for the procedure. For example, the descriptive information can be combined with additional descriptive data regarding performance of the same procedure (by the user and/or other users). The combined data can be processed using one or more machine learning or deep learning techniques to develop guidelines regarding optimal steps for the procedure and characteristics of the steps.

If guidelines are set for the procedure, at 510, the AR assistance module 110 can compare (e.g., using the procedure assessment component 116) the user actions (and characteristics of the actions, as determined via the procedure characterization component 114) with the guidelines. Based on the comparison, at 512, the AR assistance module 110 can determine whether the user deviates from the guidelines. If the user does not deviate the guidelines, the AR assistance module can continues to monitor the user's performance. In some implementations, if the AR assistance module can also provide the user with praise information regarding the good performance. If however the user does deviate from the guidelines, at 516, the AR assistance module 110 can determine feedback for providing to the user based on the deviation, and at 518 feedback can be provided to the user in real-time using AR (e.g., at user device 102). In other implementations, if the user does deviate from the guidelines, at 514, the AR assistance module can notify the user's supervisor in real-time. Details regarding generating and sending such notifications are described infra with reference to FIG. 7 and notification component 702.

FIG. 6 illustrates a block diagram of an example system 600 that facilitates providing auxiliary information regarding healthcare procedure performance using AR in accordance with one or more embodiments described herein. System 600 includes same or similar features and functionality as system 100 with the addition of recording component 602 and optimization component 604 to the AR assistance module 110. Repetitive description of same or similar functionalities of like components described in prior embodiments is omitted for sake of brevity.

In one or more embodiments, the AR assistance module 110 can include recording component 602 to record and compile data received and processed by the AR assistance module 110 over time. This compiled data can be regularly processed by the optimization component 604 using one or more machine learning techniques and/or deep learning techniques to facilitate automatically optimizing or enhancing the accuracy and quality of determinations made by the procedure identification component 112, the procedure characterization component 114, and the procedure assessment component 116.

For example, each time the AR assistance module is used to monitor and evaluate a procedure performed by a healthcare employee, the recording component 602 can record or store (e.g., in memory 130, in one or more external information sources 138, or another device) information regarding the received input used to evaluate the procedure. This information can include for example, visual (e.g., image and/or video) data received, audio data received, motion data received, biometric data received, machine generated data, and the like. The recording component 602 can further record descriptive information determined by the procedure characterization component 114 based on the received input. This information can include for example, information regarding objects and people detected, information regarding movement of the people and objects, information identifying the procedure being performed, information regarding actions or steps performed (e.g., as determined based on the people, objects and movements, and other inputs), information regarding characteristics of the procedure actions/steps, and the like. The recording component 602 can record such information for all procedures monitored by the AR assistance module over time performed by various healthcare professionals. Using this compiled data as well as data available at one or more external information sources 138, the optimization component 604 can perform one or more machine learning and/or deep learning techniques to improve the determinations made by the procedure identification component 112 regarding accurately identifying a procedure that is being performed. In addition, using this compiled data as well as data available at one or more external information sources 138, the optimization component 604 can perform one or more machine learning and/or deep learning techniques to improve the determinations made by the procedure characterization component 114 regarding accurately characterizing the various actions and characteristics of a procedure being performed and the procedural environment.

Similarly, for each procedure evaluated, the recording component 602 can record or store information (e.g., in memory 130, in one or more external information sources 138, or another device) regarding the various assessments made by the procedure assessment component 116 based on the data determined and/or generated by the procedure characterization identification component 114 and the procedure characterization component. For example, the recording component 602 can record information regarding whether and how the user's performance of the procedure deviates from the defined guidelines/protocols for the procedure. The recording component 602 can also record information regarding whether and how and aspect of the procedural environment is in accordance or discord with the defined guidelines/protocols for procedure. The recording component 602 can record such information for all procedures monitored by the AR assistance module 110 over time performed by various healthcare professionals. Using this compiled data as well as data available at one or more external information sources 138, the optimization component 604 can perform one or more machine learning and/or deep learning techniques to improve the determinations made by the procedure assessment component 116 regarding accurately determining whether and how a user's performance of a procedure and/or procedural environment deviates from guidelines/protocols for the procedure that is being performed. In some embodiments, based on the compiled data and information regarding patient and financial outcomes associated with a monitored procedure, using machine learning and/or deep learning techniques, the optimization component 604 can modify the defined guidelines/protocols for respective procedures.

In order to provide for or aid in the numerous inferences described herein, optimization component 604 can examine the entirety or a subset of the data to which it is granted access and can provide for reasoning about or infer states of the system (e.g., system 600 and the like), environment, etc. from a set of observations as captured via events and/or data. An inference can be employed to identify a specific context or action, or can generate a probability distribution over states, for example. The inference can be probabilistic (e.g., the computation of a probability distribution over states of interest can be based on a consideration of data and events). An inference can also refer to techniques employed for composing higher-level events from a set of events and/or data.

Such an inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x4, x4, xn), to a confidence that the input belongs to a class, such as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

Figure 7:
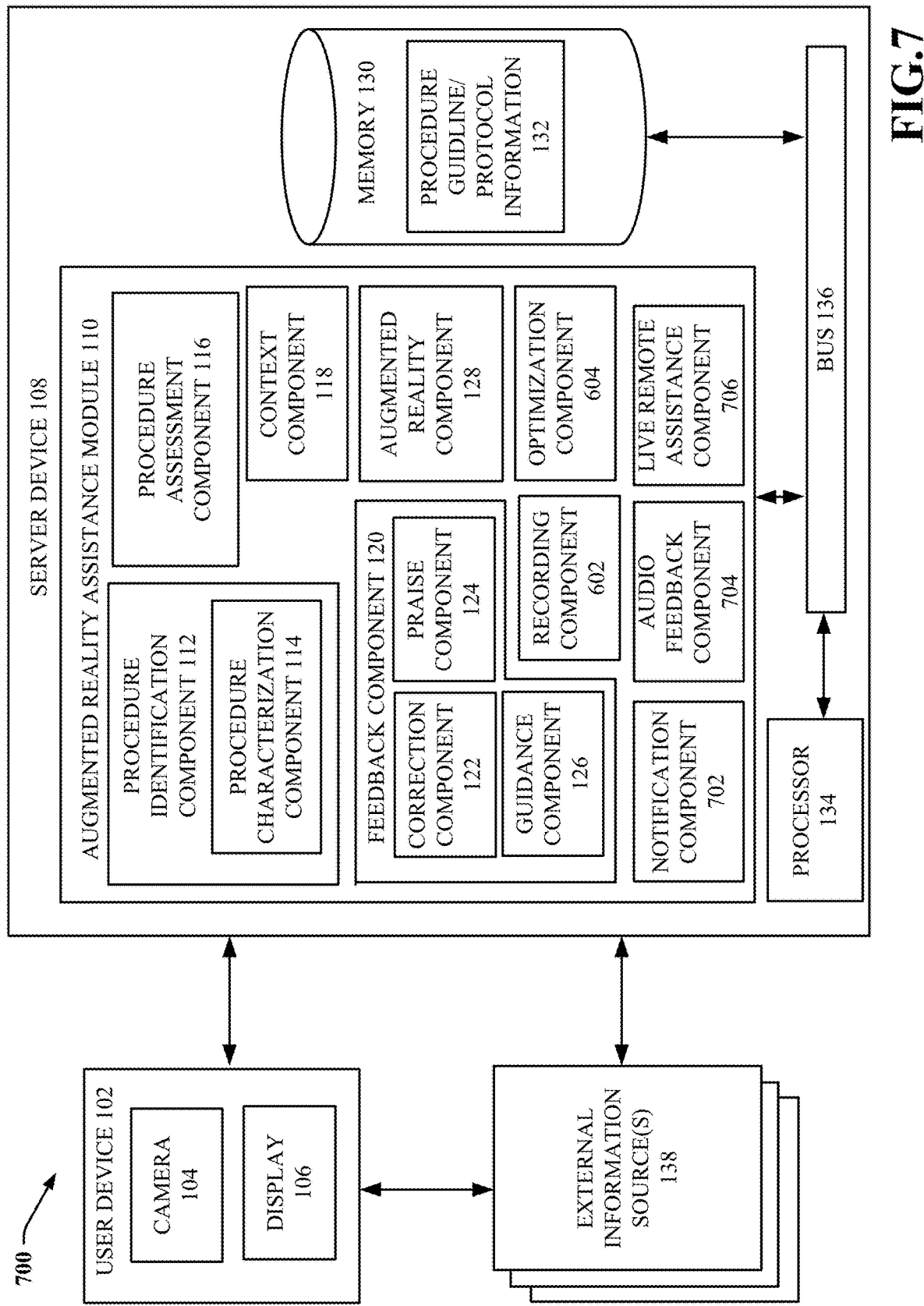
FIG. 7 illustrates a block diagram of an example system that facilitates providing auxiliary information regarding healthcare procedure performance using AR in accordance with one or more embodiments described herein.

FIG. 7 illustrates a block diagram of another example system that facilitates providing auxiliary information regarding healthcare procedure performance using AR in accordance with one or more embodiments described herein. System 700 includes same or similar features and functionality as system 600 with the addition of notification component 702, audio feedback component 704 and live remote assistance component 706 to the AR assistance module 110. Repetitive description of same or similar functionalities of like components described in prior embodiments is omitted for sake of brevity.

In various embodiments, in addition to providing a user with feedback regarding performance of a procedure or a procedural environment using AR visualizations, the AR assistance module 110 can also be configured to generate and provide notifications, audio feedback and/or live remote assistance during the procedure. For example, the notification component 702 can be configured to generate notifications in real-time regarding an aspect of a procedure being performed that deviates from the defined guidelines/protocols for the procedure. Such notifications can be provided to an entity other than the user performing the procedure. For example, based on a determination (e.g., by procedure assessment component 116) that aspect of a procedure being performed by a healthcare professional deviates from the defined guidelines/protocols for the procedure, the notification component 702 can be configured to generate and send a notification regarding the deviation to a supervisor of the healthcare professional or another suitable entity. For example, the notification can be sent to a device of the supervisor in the form an electronic message, a phone call, or the like.

In some embodiments, the entity (and associated device) that the notification component 702 sends the notification to can be based on the type of the notification or the reason for the notification. According to these embodiments, the notification component 702 can determine a type of the notification based on the deviation for which the notification is based. For example, if the notification concerns missing or inoperative supplies or equipment, the notification component 702 can be configured to send the notification to a particular maintenance employee. In another implementation, certain potential errors can be associated with different severity classifications. According to this implementation, based on a determination that a particular aspect of a procedure deviates from protocol, the notification component 702 can access information (e.g., stored in memory 130, at one or more external information sources 138, or another device), that indicates a classification for the current error. For example, if the error is performance of step 2 of a particular procedure incorrectly, the notification component 702 can access information that indicates a severity classification for performance of step 2 of this particular procedure incorrectly. Based on the severity classification, the notification component 702 can be configured to send the notification to a defined entity that is instructed to supervise notifications having that severity classification. In another aspect, the notification component 702 can include information indicating the severity of the error in the notification. The type of the notification can also vary based on the severity classification (e.g., a code blue notification can indicate moderate severity, while a code red notification indicates high severity).

In some implementations, the notification component 702 can be configured to send notifications for only certain types of errors having a severity classification above a defined threshold level. In yet another implementation, the notification component 702 can be configured to monitor the number, frequency and/or severity levels associated with errors or deviations detected during performance of a procedure by a healthcare professional. The notification component 702 can further be configured to generate and send a notification to a defined entity (e.g., a supervisor) based on the number, frequency and/or compiled severity levels of the errors/deviations being above a threshold level. Certain procedures can be marked as high, medium, and low risk as severity classifications, for example. The higher the severity, the more damage to patient health or the healthcare institution could occur if the procedure is not performed correctly. For example, checking a patient in at the front desk might be a low risk procedure and performing a heart surgery might be a high risk procedure.

The audio feedback component 704 can be configured to provide feedback determined and/or generated by the feedback component 120 to a healthcare professional performing a procedure in audio form (in addition to or in the alternative to an AR form). According to the embodiment, the healthcare professional can wear (e.g., included in the user device 102) or otherwise be within audible range of a speaker via which the audio feedback component 704 can send the audio feedback for playback. In some implementations, the audio feedback component 704 can provide the healthcare professional with a defined sound to indicate when an error is detected (e.g., an alarm sound). Likewise, the audio feedback component 704 can also provide the healthcare professional with another device sound if the healthcare professional performs an aspect of a procedure correctly. In other implementations, the audio feedback component 704 can generate a spoken rendering of the feedback generated by the feedback component 120 for playback to the healthcare professional as speech. For example, if the healthcare professional performs step 2 of a procedure incorrectly, the audio feedback component 704 can generate and provide the healthcare professional with a verbal instruction stating that step 2 was performed incorrectly. The verbal instruction can also explain the aspect of step 2 that was performed incorrectly and further provide instruction regarding how to correct the error. Thus while performing the procedure, the healthcare professional can listen to the feedback and respond accordingly in real-time.

The live remote assistance component 706 can be configured to provide a healthcare professional with live remote assistance during a procedure when such assistance is needed or requested. For example, in some embodiments, based on detection of certain errors associated with high severity levels (e.g., based on a predefined severity classification system), errors above a certain amount, frequency, severity, etc., the live remote assistance component 706 can be configured to automatically connect the healthcare professional to another person at a remote location to help guide the healthcare professional. In other embodiments, the healthcare physician can initiate and request the live remote assistance functionality on demand. Using the connection, the healthcare professional and the remote assisting entity can communicate via a voice and/or voice and video media session. The live remote assisting entity can further provide the healthcare professional with live assistance during the procedure. In some implementations, the remote assisting entity can be provided with a live visual feed (e.g., capture via camera 104 or another camera in the procedure environment) of the procedure and/or the procedural environment to facilitate assisting the healthcare professional. For example, in some implementations, the user device 102 can include a phone or phone application with voice and/or video capabilities. According to this example, the live remote assistance component 706 can automatically a call to the user's phone or phone application that connects the healthcare professional to the remote assisting entity. In another example implementation, the call or live media session can be established between the remote assisting entity and another device in the procedure environment that can be seen and/or heard by the healthcare professional.

Figure 8:
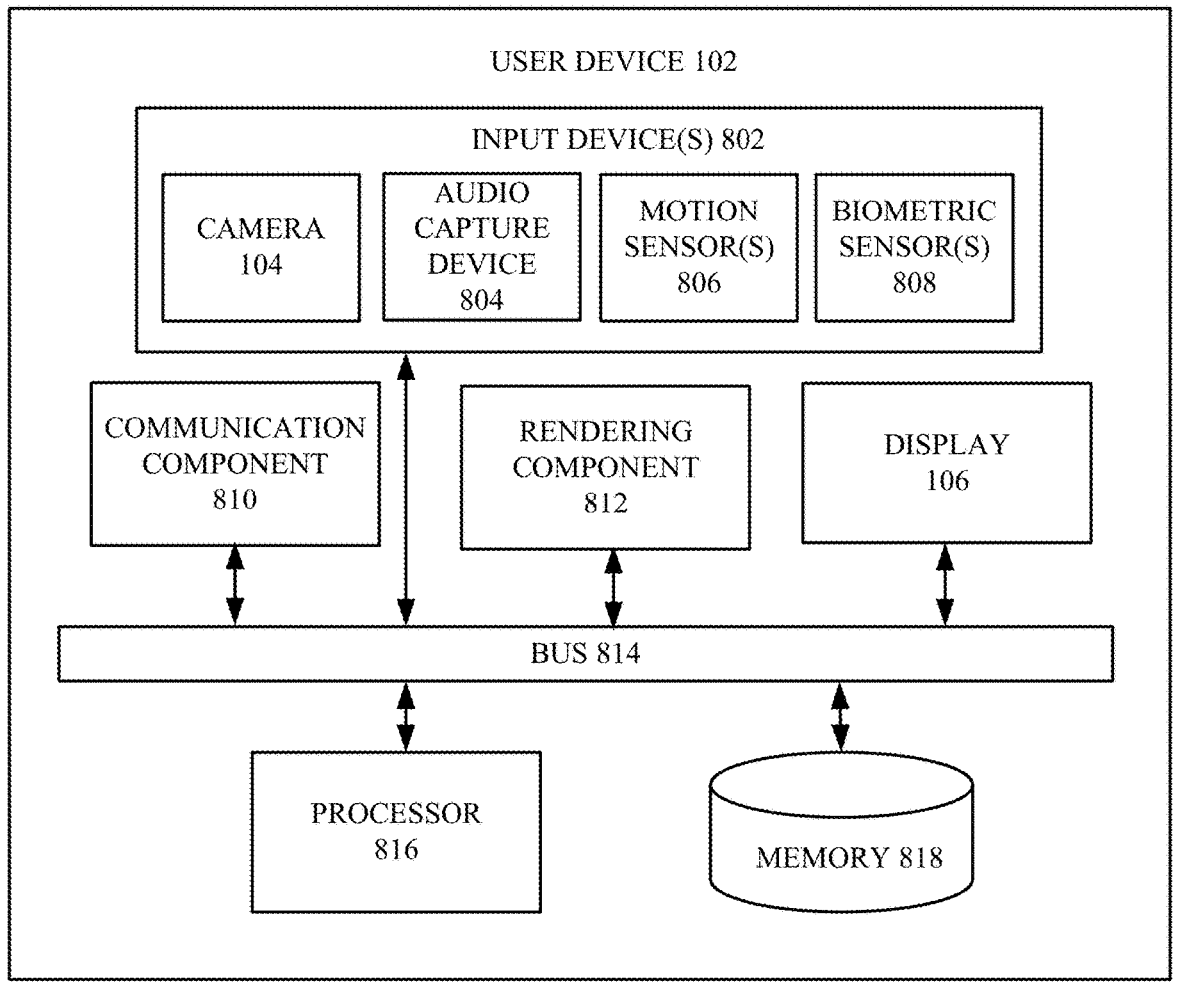
FIG. 8 illustrates a block diagram of an example user device that facilitates providing auxiliary information regarding healthcare procedure and system performance using AR in accordance with one or more embodiments described herein.

FIG. 8 illustrates a block diagram of an example user device (e.g., user device 102) that facilitates providing auxiliary information regarding healthcare procedure and system performance in real-time using AR in accordance with one or more embodiments described herein. Repetitive description of like embodiments employed in respective embodiments is omitted for sake of brevity.

User device 102 can include one or more input devices 802, communication component 810, rendering component 812 and display 106. The user device 102 can also include or otherwise be associated with at least one memory 818 that stores computer-executable components (e.g., the rendering component 812). The user device 102 can also include or otherwise be associated with at least one processor 816 that executes the computer-executable components stored in the memory 818. The user device 800 can further include a device bus 814 that can couple the various components including, but not limited to, the one or more input devices 802, the communication component 810, the rendering component 812, the display 106, the processor 816 and the memory 818.

In one or more embodiments, the user device 102 can capture feedback regarding performance of a healthcare procedure by a healthcare professional and/or regarding a healthcare environment. The user device 102 can further provide this feedback to the AR assistance module 110 for processing in real-time in association with evaluating performance of the procedure and/or the environment. For example, the one or more input device 802 can include camera 104 which is previously described. The one or more input devices 802 can also include but are not limited to, an audio capture device 804, one or more motion sensors 806 and/or one or more biometric sensors. The audio capture device 804 can include a microphone or another type of audio capture device that can receive and record audio during a procedure, such as speech spoken by the healthcare professional performing the procedure, the patient, and/or one or more other healthcare professionals involved in the procedure. In some implementations, the audio capture device 804 can further process captured audio to convert detected speech to text for providing to the AR assistance module 110. The one or more motion sensors 806 can include, for example, an accelerometer and/or a gyroscope that can detect motion of the user device 102 when worn, held or otherwise operated by the user. The one or more biometric sensors 808 can include biometric sensors that detect biometric information for the user during performance of a procedure, including but not limited to, heart rate, respiratory rate, stress hormone levels of the user, and the like. In some implementations, one or more of the motion sensors 806 and/or the biometric sensors 808 can be external to the user device 102 (e.g., worn by a user, implanted within a user, etc.) and communicatively coupled to the user device 102.

The communication component 810 can facilitate wired and/or wireless communication between the user device 102 and the server device 108, the one or more external information sources 138 and/or another suitable external device (not shown). For example, the communication component 310 can receive real-time feedback information from the AR assistance module (e.g., via the AR component 128, the notification component 702, the audio feedback component 704, and/or the live remote assistance component 706) regarding performance of a procedure or procedural environment. The communication component 310 can be or include hardware (e.g., a central processing unit (CPU), a transceiver, a decoder), software (e.g., a set of threads, a set of processes, software in execution) or a combination of hardware and software that facilitates the various type of wireless communicating information of information described herein.

The rendering component 812 can be configured to render the feedback received from the AR assistance module 110 in real-time. For example, in an embodiment in which the auxiliary information includes audio, the rendering component 812 can cause the audio to be played at the user device 102 via a speaker of the user device (e.g., not shown). In another example, in an embodiment in which the feedback includes visual overlay data provided by the AR component 128 (e.g., text, symbols, icons, images, video, hyperlinks, etc.), the rendering component 812 can generate a graphical user interface that can be displayed via the display 106 of the user device 102. The graphical user interface can include the overlay data overlaid onto a view of the user's environment. In some implementations, the view includes a real direct view of the environment as viewed through a transparent display (e.g., glasses, goggles, contact lenses, etc). In other implementations, the view can include live or recorded video/image data of the environment rendered from a current perspective of the user relative to the environment. In another example implementation, the view can include a 2D or 3D model of the environment rendered from the current perspective of the user relative to the environment.

The manner in which the overlay data is rendered in the graphical user interface can vary. For example, as exemplified in FIGS. 2-4, the overlay data can be displayed as text and/or symbols included in semi-transparent pop-up display window or frame. In some implementations, the overlay data can include visual data that highlights (e.g., in a distinguishing color), or otherwise draws attention to a particular object viewed by the user via the display. For example, as exemplified in FIG. 2, the overlay data can include color data that highlights the appearance of the IV fluid bag. In some embodiments, the overlay data can be selected or otherwise interacted with (e.g., to follow a hyperlink represented in the overlay data, to play a video represented in the overlay data, and the like).

In one or more embodiments, the rendering component 812 can render the overlay data such that it is spatially aligned with one or more defined objects included in the view of the user's environment viewed through or on the display 106 (e.g., a real direct view or an indirect view consisting of image/video data or model data). According to these embodiments, the one or more objects for spatially aligning the overlay data with can be determined by the AR component 128 and provided to the rendering component 812 with the overlay data (e.g., as metadata). For example, the AR component 128 can provide the rending component 812 with overlay data as well as information indicating the overlay data should be aligned with a certain object, such as the "incision site." Based on the information identifying the object, in some implementations, using image analysis techniques, the rendering component 812 can identify the incision site in the image data of the environment corresponding to a current perspective of the user relative to the environment. For example, the image data can include a still image of the environment, live video data of the environment, or model data of the environment as viewed from the current perspective of the user to the environment. The rendering component 812 can further determine the relative spatial location of the object in the image data to the user, including the relative (3D) location of the object to the user (e.g., based depth information associated with the object and a known position/orientation of the user). In other embodiments, the rendering component 812 can receive information from the procedure characterization component 114 identifying the relative spatial location of the object to the user in corresponding image data. The rendering component 812 can further render the overlay data on the display 106 based on the relative spatial location of the object in the image data and the current perspective of the user relative to the object such that it appears to be spatially aligned on or near the object.

Figure 9:
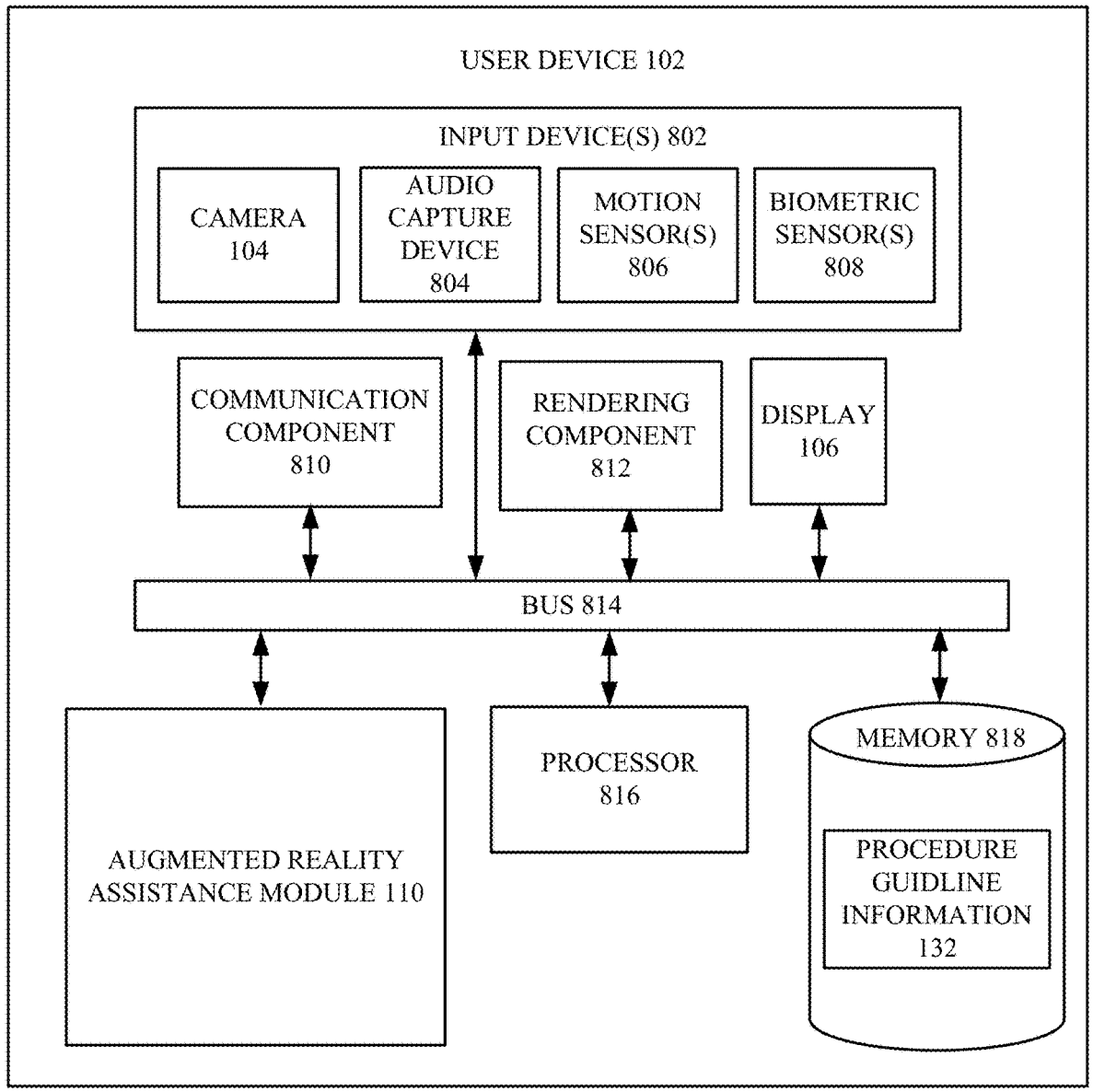
FIG. 9 illustrates a block diagram of an example user device that facilitates providing auxiliary information regarding healthcare procedure and system performance using AR in accordance with one or more embodiments described herein.

FIG. 9 illustrates a block diagram of another example user device (e.g., user device 102) that facilitates providing auxiliary information regarding healthcare procedure and system performance in real-time using AR in accordance with one or more alternative embodiments described herein. In particular, in the embodiment shown, the user device 102 includes the AR assistance module 110. The user device 102 also include the procedure guideline/protocol information 132 in memory 818. According to this embodiment, the user device 102 can perform the various processing functions provided by the AR assistance module 110 without communicating with the sever device 108. The user device 102 can further communicate with one or more external information sources 138 to access information as needed. Repetitive description of like embodiments employed in respective embodiments is omitted for sake of brevity.

Figure 10:
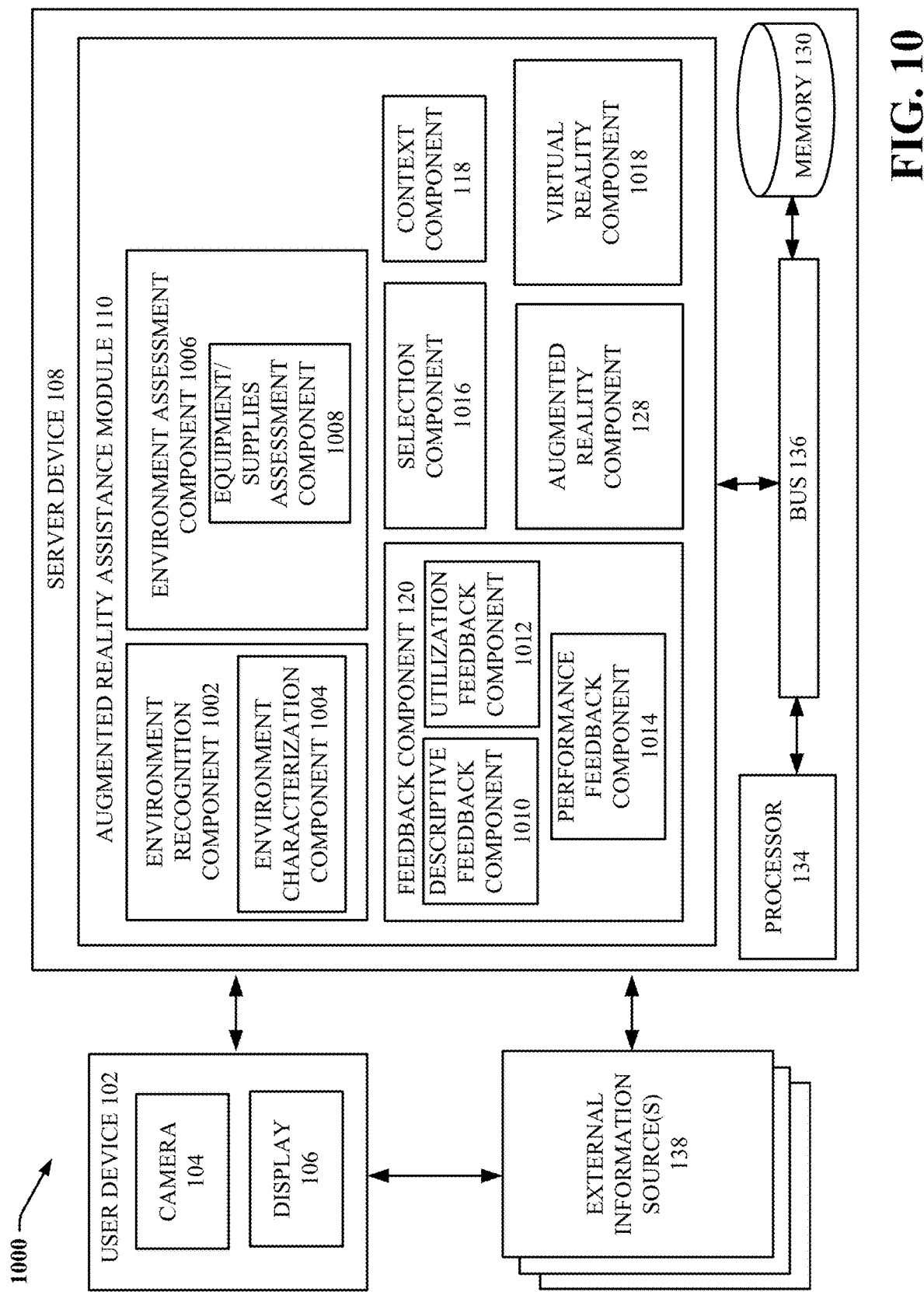
FIG. 10 illustrates a block diagram of an example system that facilitates providing auxiliary information regarding healthcare system performance using AR in accordance with one or more embodiments described herein.

Referring now to FIG. 10, presented is a block diagram of an example system 1000 that facilitates providing auxiliary information regarding healthcare system performance in real-time using AR in accordance with one or more embodiments described herein. System 1000 can include same or similar features and functionality as systems 100, 600 and 700. However, system 1000 adds some additional components to the AR assistance module 110 that facilitate additional and/or alternative functions of the AR assistance module 110 related to providing a user auxiliary information in real-time regarding the utilization and performance of physical elements of a healthcare facility that are currently being viewed by the user. These additional components include environment recognition component 1002 and an associated environment characterization component 1004, environment assessment component 1006 and associated equipment/supplies assessment component 1008, selection component 1016, and virtual reality (VR) component 1018. These additional components also include some new subcomponents of the feedback component 120, including descriptive feedback component 1010, utilization feedback component 1012, and performance feedback component 1014. Repetitive description of same or similar functionalities of like components is omitted for sake of brevity.

The AR assistance module 110 can be configured to perform various AR type services associated with facilitating healthcare professionals performing their jobs. As described with reference to systems 100, 600 and 700, in various embodiments, the AR assistance module 110 can be configured to assist healthcare professionals when performing a defined healthcare procedure by providing the healthcare professional with auxiliary information, determined in real-time, that is relevant to a current aspect of the procedure being performed.

In various additional embodiments, as exemplified in system 1000 (and additional systems 1300 and 1600 described supra), the AR assistance module 110 can be configured to assist healthcare administrators (or other type of healthcare organization employee) in understanding and assessing various aspects of a state of performance of a healthcare organization by providing the healthcare administrators with auxiliary information associated with a current physical area of a healthcare facility of the organization the healthcare professional is viewing or otherwise examining. For example, the healthcare organization can include but is not limited to: a hospital network, a hospital, a nursing home, an assisted living facility, a physical therapy facility, a pharmacy, a clinic, a medical imaging facility, a laboratory, and the like. The different areas of the healthcare facility will vary based on the type of healthcare facility. For example, with respect to a hospital, the different areas may be associated with different sectors or departments of the hospital that provide different medical services (e.g., emergency, surgery, pediatrics, internal diseases, gynecology, nursing, laboratory, imaging, etc.), and different rooms/areas in the respective sectors or departments (e.g., patient waiting room, patient examination room, clerical room, supplies room, etc.).

In one or more embodiments, the environment recognition component 1002 can be configured to determine an area or environment of a healthcare facility that user is currently viewing or would like to view and the environment characterization component 1004 can be configured to characterize various aspects of the environment or area. In this regard, the environment characterization component 1004 can be configured to identify physical objects (e.g., equipment, supplies, furniture, people, etc.) included in the area. The environment characterization component 1004 can further be configured to determine the relative 2D and/or 3D spatial locations of the objects to one another and a user viewing the area based on the current perspective of the user.

In some embodiments, the environment recognition component 1002 can determine the area/environment based on received image data (e.g., video and/or still images) captured of the area/environment. For example, in one implementation, a user can wear or hold the user device 102 as the user moves throughout a healthcare facility and capture image data (e.g., video and/or still images) of the healthcare facility via the camera 104 from the perspective or the user. The user device 102 can further provided the image data to the AR assistance module 110 for processing thereof in real-time. According to this implementation, using one or more image analysis techniques, the environment characterization component 1004 can identify one or more objects and features of a current area or environment being viewed by the user. For example, the environment characterization component 1004 can identify objects (e.g., equipment, supplies, furniture, people) included in the image data using pattern recognition techniques or other image analysis techniques. The environment characterization component 1004 can further be configured to determine the relative 2D and/or 3D spatial locations of the objects to one another and a user viewing the area based on the current perspective of the user. For example, in some implementations, the image data can be associated with depth or distance information for respective objects (i.e., groups of identified pixels forming the respective objects) included therein. This depth information be can be captured via the camera that captures the image data and/or determined using stereoscopy analysis of partially overlapping images. The environment characterization component 1004 can further determine the spatial locations of the objects based on the depth or distance information. In some implementations, the environment recognition component 1002 can further access indexed information (e.g., stored in memory 130, one or more external information sources 138, or at another device) that associates the one or more objects and/or patterns in the image data (e.g., regarding relative positions of the objects and the types of objects) with defined physical locations or positions (e.g., camera positions/perspectives) in the healthcare facility. The environment recognition component 1002 can then determine the location and/or current position/perspective of the area of the environment being viewed based on comparison of the detected objects and/or patterns in the detected objects with the indexed information.

In another implementation, the environment recognition component 1002 can receive image data (e.g., video and/or still images) of a user as the user moves about a healthcare facility. For example, the image data can be captured via cameras dispersed at various locations throughout the healthcare facility and provided to the AR assistance module 110 in real-time for processing. According to this implementation, using one or more image analysis techniques, the environment characterization component 1004 can identify the user and track the user as the user moves throughout the environment. Using one or more image based analysis techniques, the environment characterization component 1004 can further identify objects included in a current area or environment being viewed by the user as the user moves about the healthcare facility. For example, the environment characterization component 1004 can identify objects (e.g., equipment, supplies, furniture, people), and relative locations of the objects in the image data that appear within a determined field of view of the user. In some implementations, the environment recognition component 1002 can further access indexed information (e.g., stored in memory 130, one or more external information sources 138, or at another device) that associates the one or more objects and/or patterns in the image data with defined physical locations or positions (e.g., camera positions/perspectives) in the healthcare facility. The environment recognition component 1002 can then determine the location and/or current position/perspective of the area of the environment being viewed based on comparison of the detected objects and/or patterns in the detected objects with the indexed information.

Various additional techniques can be used to determine a current position of a user relative to various areas and associated objects in a healthcare facility as the user moves about the healthcare facility. For example, in embodiments in which the user wears or holds the user device 102 as the user moves about the facility, the user device 102 can be configured to determine the current location of the user using various location based detection methods (e.g., GPS, triangulation, beacons, detection of RFID tags associated with defined location information and/or perspectives of the facility). In another example, the context component 118 can determine the location of the user by evaluating movement of the user based on image data captured of the user and/or from the user's perspective (e.g., via camera 104 in implementations in which the user wears or holds the user device). Similarly, in some implementations, the user device can include one or more motion sensors configured to generate motion data as the user moves about the healthcare facility and/or looks in different directions/orientations with the user device (e.g., when the user device 102 includes an eyewear device). The context component 118 and/or the user device can further evaluate the motion data in real-time to determine the current location and/or perspective of the user based on the motion data (e.g., including movement and orientation information).

In some implementations, based on determination of a current location and/or perspective of a user relative to an area/environment of a healthcare facility (e.g., determined using GPS data, triangulation, RFID tags, motion information, etc.), the environment characterization component 1004 can determine objects that are associated with the current location and perspective of the user using indexed information that associates known objects with the current location/perspective. Still in other embodiments, the user device 102 can be configured to identify objects that are in line of site and/or a current field of view of the user based on image data captured by the camera 104 and a know position/orientation of the user. The user device 102 can further provide the AR assistance module 110 with object information identifying the objects and the relative positions of the objects to the user based on the user's current position/orientation.

In another implementation, the user can be located at a different location relative to the area or environment of the healthcare facility that the user desires to view. For example, using a device (e.g., user device 102) that is located a remote location, the user can access and view image data (e.g., video and/or still image data) of a selected area of the healthcare facility. For example, the user can provide input indicating an area of the healthcare facility the user would like to view (e.g., such as input requesting a view of operating room B). Based on received user input indicating a desired area and/or view of the healthcare facility, the user device 102 can be configured to render (e.g., via rendering component 812) image data of the desired area. The image data can include live video data being captured of the selected area, still image data captured of the selected area, or model data (e.g., 2D/3D model data) including a regenerated representations or models of the selected area. With this implementation, the particular area and/or view of the environment will be known to the environment recognition component 1002 based on the input selection made by the user. In some one or more embodiments, the environment characterization component 1004 can use image analysis to identify objects and relative locations of the objects in the image data that is rendered to the user. For example, in implementations in which live video data of the selected location is rendered to the user, the environment characterization component 1004 can analyze the image data to identify objects and relative locations of the objects in the image data. In other embodiments, the environment characterization component 1004 can access indexed information (e.g., in memory 130, at one or more external information sources 138, or at another device), that associates known objects with respective areas in the healthcare facility. Based on the selected area, the environment characterization component 1004 can employ the indexed information to identify objects that are included in the selected area. In some implementations, the environment characterization component 1004 can used this indexed information to assist with identifying objects included in the rendered image data using one or more image based analysis techniques.

The environment assessment component 1006 can be configured to assess a current area of a healthcare facility that is viewed (or has been selected for view) by a user based on the information determined, generated and/or received by the environment recognition component 1002 identifying the current area and/or information determined, generated, and/or received by the environment characterization component 1004 identifying objects and relative locations of the objects included in the user's current view. The environment assessment component 1006 can be configured to determine a variety of information associated with the area and the one or more objects included in the view of the area.

In implementations in which the one or more objects include equipment or supplies, the environment assessment component 1006 can employ the equipment/supplies assessment component 1008 to determine various types of equipment/supplies information associated with the equipment or supplies. For example, the equipment can include medical equipment (e.g., imaging machines, anesthesia machines, etc.) and non-medical equipment (e.g., computers used for clerical purposes, maintenance equipment, etc.). The supplies can include any type of medical supply, for example tools or instruments used for performing a procedure (e.g., surgical supplies), laboratory supplies, pharmaceuticals, and the like. In some implementations, the supplies can also included non-medical supplies (e.g., office supplies). The equipment/supplies information can include but is not limited to: descriptive information that describes specifications of the equipment or supplies, utilization information regarding utilization of the equipment or supplies, and performance information regarding clinical and/or financial performance of the healthcare facility associated with the equipment or supplies. For example, descriptive information associated with a particular piece of medical equipment or supply can include the type of information that would be likely be associated with the equipment or supply on a sales specification, such as but not limited to: a name or title for the equipment or supply, a description of the intended use, a manufacturer make and model, a dimension or sizing information, cost information, and the like. Utilization information regarding utilization of a particular piece of medical equipment or supply can include information regarding usage of the medical equipment or supply by the current healthcare organization. For example, such usage information can describe how the healthcare facility uses the medical supply or equipment, information regarding degree of past usage, information regarding frequency of past usage, information regarding expected usage, and the like. In another example, the usage information can relate to current usage state or status of the medical supply or equipment (e.g., used or unused). In yet another example, the usage information can include information that effects usage of a medical supply or equipment, such as information regarding maintenance type issues associated with a piece of medical equipment or supply.

Performance information regarding clinical performance of the healthcare facility associated with the equipment or supplies can include for example information regarding patient success outcome information and quality of care associated with usage of a piece of medical equipment or medical supply. In some embodiments, this type of performance information can be compared to usage of alternative supplies, such as relative success rates and relative quality of care. Clinical performance information associated with medical supplies can also include regarding usage and availability of supplies that affect the clinical performance of the healthcare organization. For example, such information can indicate whether there is a surplus or deficiency in amount of the supply available to meet patient needs. In another example, such information can indicate whether a supply or tool was used properly, disposed of properly, cleaned properly, stored properly and the like. Likewise, performance information regarding financial performance of the healthcare facility associated with equipment or supplies can include financial gain and loss information attributed to usage of a piece of medical equipment or medical supply.

In various embodiments, the descriptive, utilization and/or performance information that is associated with the equipment and supplies identified by the environment characterization component 1004 can be predetermined and included in one or more databases accessible to the AR assistance module 110 (e.g., in memory 130, at one or more external information sources 138, or at another device). For example, such information can have been previously generated in various inventory logs, device logs, purchase reports, maintenance reports, and performance evaluation reports/logs, billing reports, and the like, and associated with the respective supplies and/or equipment. Usually, such device logs and error logs are reviewed by only folks with deep technical know-how. With the system and methods contemplated herein, system 100 can find relevant information and make it easy to view and understand for non-technical folks such as clinicians and hospital administrators.

According to these embodiments, the equipment/supplies assessment component 1008 can scan various databases and sources to find and retrieve such information associated with a supply or medical equipment that is included in a user's current view. In other implementations, the equipment/supplies assessment component 1008 can run real-time reports on the data included in the various databases and sources to generate the utilization and performance information in real-time. For example, with respect to financial performance information associated with equipment and supplies included in an area of a healthcare facility viewed by a user, the equipment/supplies assessment component 1008 can access purchase information, usage information, maintenance information, billing information, etc. associated with usage and performance of the respective supplies and equipment and determine monetary values indicating costs associated with the respective supplies and equipment. For example, the cost information can indicate costs to the healthcare organization attributed to purchasing, using and maintaining the respective supplies and equipment and/or ROI associated with the supplies and/or equipment. The equipment/supplies assessment component 1008 can also access information regarding expected and/or budgeted costs for the equipment and supplies and determine information regarding a degree to which the actual costs associated with certain supplies and equipment are over budget or under budget.

The feedback component 120 can be configured to collate the information retrieved, generated or determined by the environment assessment component 1006 for potential provision as auxiliary information to the user viewing the assessed area as feedback in real-time. For example, the descriptive feedback component 1010 can collect and collate descriptive information generated by the equipment/supplies assessment component 1008 that describes specifications of the equipment or supplies. The utilization feedback component 1012 can collect and collate utilization information generated by the equipment/supplies assessment component 1008 regarding utilization of the equipment or supplies, and the performance feedback component 1014 can collect and collate performance information generated by the equipment/supplies assessment component 1008 regarding clinical and/or financial performance of the healthcare facility associated with the equipment or supplies. Such collection and collation of the descriptive, utilization, and performance information can include cleaning and indexing the information based on the respective objects (e.g., equipment or supply) each piece of information is associated with. In various implements, the feedback component 120 can associate metadata with each piece of information identifying the particular object that it is associated with.

Given the amount of potential feedback information that can be gathered by the feedback component 120 regarding an area of a healthcare facility that is being viewed by a user, in many scenarios it may not be feasible or useful to provide the user with all the feedback information. For example, with respect to supplies and hardware identified, a user may only be interested in receiving financial performance information associated with a single piece of equipment in the room. The in various implementations, the amount and type of feedback information that is provided to a particular user can be filtered and selected by the selection component 1016 based on a current context of the user. In particular, the selection component 1016 can select a subset of the feedback information (e.g., generated/collated by the feedback component 120) for provision to a user viewing an area of a healthcare facility based on a current context of the user. In some implementations, the current context of the user can be determined by the context component 118 (e.g., based on information included in memory or one or more external information sources 138, based on received information regarding movement of the user, and the like). In this regard, the current context can include but is not limited to: a role of the user at the healthcare facility (e.g., job title and description), authorization of the user to receive various types of information (e.g., the CEO is more privy to certain financial information relative to entry level secretary), or a purpose of the user for viewing a particular area (e.g., to gain financial information, to evaluate sanitation and maintenance, to perform maintenance duties, etc.). For example, the auxiliary information that is provided to a maintenance worker can reflect maintenance issues associated with equipment in an observed area while the auxiliary information that is provided to a finance executive can concern cost and ROI performance data associated with equipment and/or medical services supported by the area.

In some implementations, the context can also include a degree of mobility of the user. According to this implementation, the amount of information that should be displayed for each object a user views should reflect the amount of time the user will be viewing the object and the ability of the user to read or comprehend the amount of information provided. For example, if the user is walking through a hospital, the user can pass by many different objects quickly and thus not have enough time to read detailed information about each object. However, if a user is standing still and looking at an area of the healthcare facility, the user can be provided with more information about the respective objects in area.

Similar to the feedback information provided to user in association with performance of a procedure, in some implementations the AR component 128 can provide the user with feedback information regarding the state of performance of the healthcare organization using an AR experience. According to these implementations, the AR component 128 can generate overlay data that comprises or represents the subset of the information selected by the selection component 1016 for providing to the user. For example, using an AR device (e.g., user device 102), a user can physically visit an area of a healthcare facility and receive overlay data concerning the performance of the area, including equipment and supplies associated with the area, people/employees associated with the area, and the like. The overlay data can be rendered to the user via the display of the AR device as over a current view of the area viewed through or on the display. In an additional implementation, the user can remotely view the area by viewing video and/or image data captured of the area. According to this implementation, the overlay data can be overlaid onto the video and/or image data of the area that is displayed on the user's remote device. Repetitive description of the manner in which the AR component 128 generates and provides overlay data for presenting to a user is omitted for sake of brevity.

The ability to be physically situated near real world healthcare objects and have performance and financial data be overlaid on a physical view of the real world healthcare objects is valuable to clinicians and hospital administrators. They can have a more real and tangible understanding of how their healthcare institution is working, including successes and areas for improvement.

In another implementation, the user can view the area using a virtual reality (VR) system/device. According to this implementation the AR assistance module 110 can include VR component 1018 to facilitate generating overlay data for rendering to a user in a VR experience. For example, using a VR device (e.g., user device 102), a user can be presented with a 3D space model/visualization of the area that appears to the user as if the user is actually standing in the 3D space model. The auxiliary data regarding the area can be projected onto or otherwise integrated within the 3D space model view of the area. The mechanism via which the overlay data is included in a VR visualization of an area of a healthcare facility can be similar to that used for integrating overlay data on a real view of an area. However in some implementations, the overlay data provided in a VR experience can be 3D object and interacted with by the user as if it were a object the use can hold, touch, move, etc. In various embodiments, regardless as to whether the user is viewing the auxiliary data using an AR device or a VR device, the auxiliary data can be spatially aligned with respective objects, people, equipment/supplies, etc., that is associated with. For example, auxiliary data concerning how a supply cabinet in a room is under stocked with certain supplies can be overlaid on a direct view of the supply cabinet (e.g., the supply cabinet viewed through a transparent display, such as AR glasses or goggles), or an indirect view of the supply cabinet (e.g., video/image data or 3D model data of the supply cabinet presented on a display).

In one or more additional embodiments, system 1000 can facilitate providing a user with AR or VR feedback information regarding equipment and supplies associated with a location in a healthcare environment based on explicit input received from the user. For example, in various implementations, the selection component 1016 provides for automatically selecting the appropriate AR or VR feedback to provide to a user based on the user's context (e.g., the user's role or job title, the user's purpose for visiting the location, the user's mobility state, etc.). In other embodiments, the user can provide the AR assistance module with direct input indicating, requesting or selecting a particular type of feedback to be provided to the user via AR or VR. For example, the user can provide input via the user device 102 using a suitable input mechanism (e.g., a keyboard, a keypad, a touch-screen, gesture based input, voice recognition based input, etc.), identifying an object and requesting information about that object. In another example, the user can pose a question asking for information about a location or room in a healthcare facility such as requesting information about where certain supplies are located in the room. In another example, the user can provide input asking for a certain type of information about a location in the healthcare facility. According to this example, the user may say for instance, "show me supplies that are low in stock," "show me the equipment having maintenance issues," "show me the part of this imaging device that is not working properly," etc. This input can be received by the environment assessment component 1006 and/or the feedback components 120. Based on reception of the user input and other input such as the worker's current location, the environment assessment component 1006 can determine the answer to the user's question/request using the mechanisms described herein. The feedback component can further generate feedback information that answers the user's question or responds to the user's request and the AR component 128 can further provide the user with the feedback using AR or VR.

For example, a new maintenance worker wearing an AR device (e.g., user device 102) including a voice recognition input mechanism may walk into a room and provide verbal input asking where the non-latex gloves are located. The equipment assessment component 1006 can then determine where the non-latex gloves are located in the room, and the AR component 128 can provide the user with feedback in the form of an overlay that notes the particular location in the room including the non-latex gloves. For example, if the non-latex gloves are located on the left side second shelf of the supply cabinet, the overlay data can highlight, mark, or otherwise draw attention to the left side second shelf of the supply cabinet. In some implementations, the feedback component 120 can also provide the user with audio feedback instructing the worker where the non-latex gloves are located.

Figure 11:
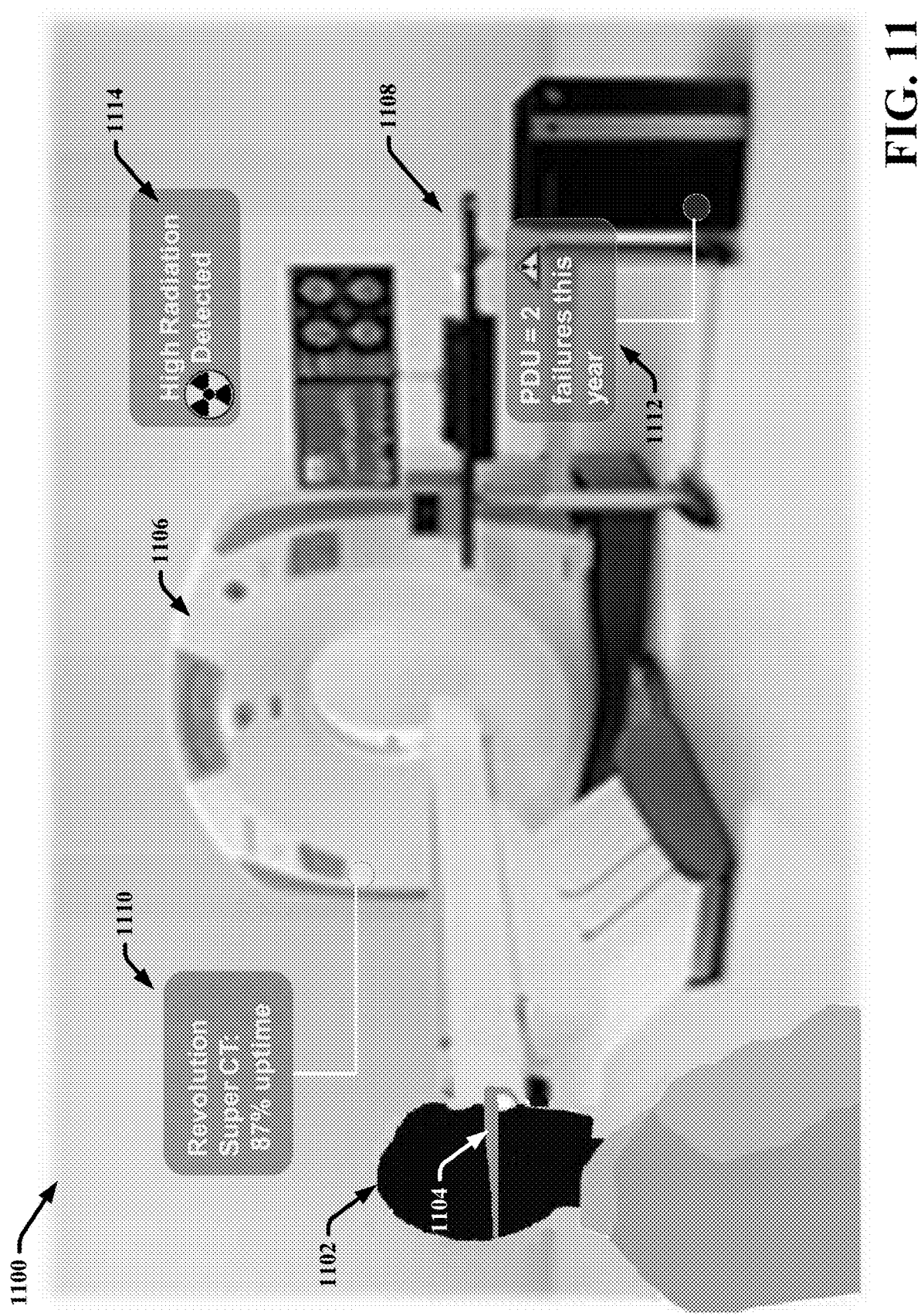
FIG. 11 presents an example AR visualization including auxiliary information regarding usage and/or performance of a healthcare system equipment in accordance with one or more embodiments described herein.
Figure 12A:
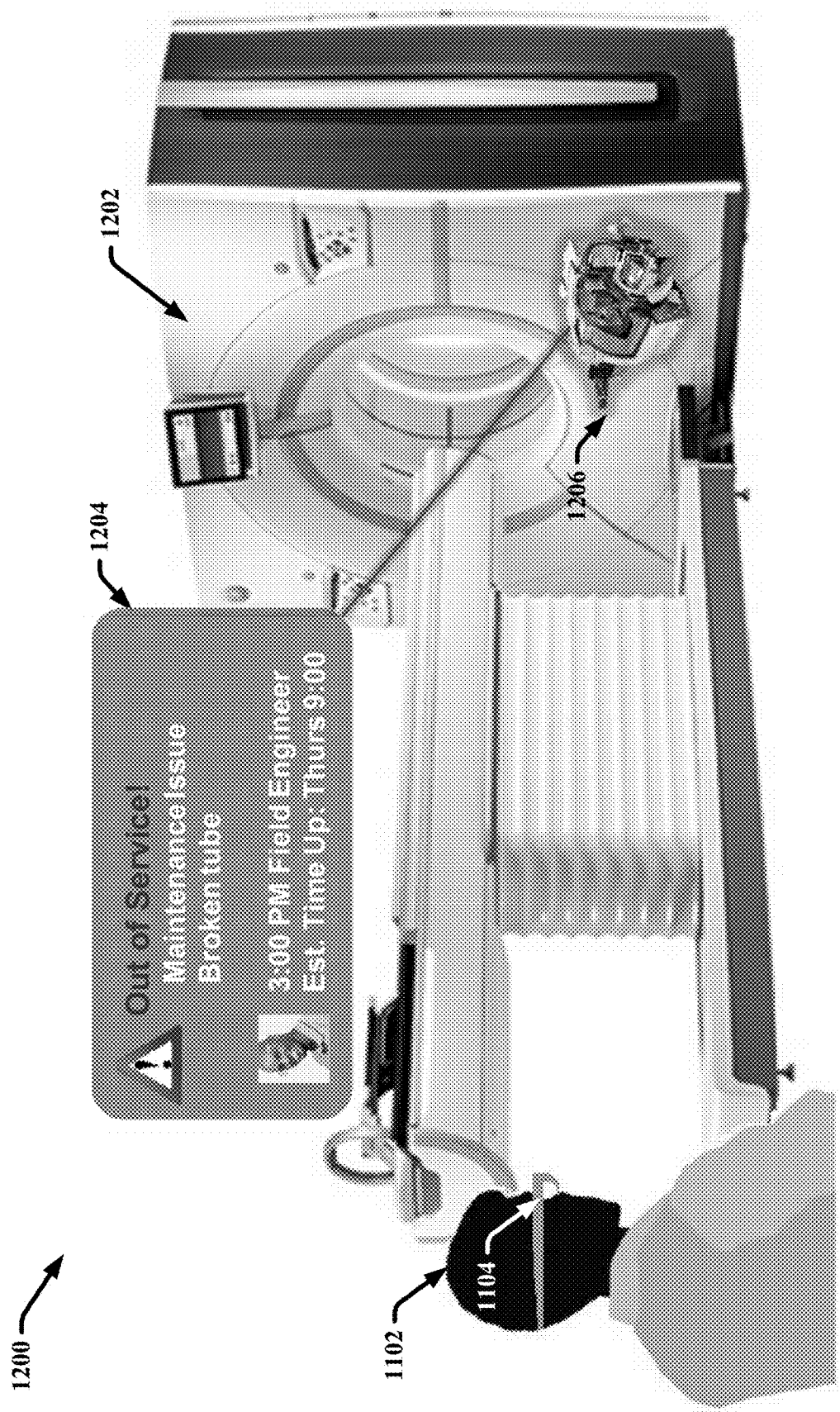
FIGS. 12A-12B presents example AR visualization respectively including auxiliary information regarding usage and/or performance of a healthcare system equipment in accordance with one or more embodiments described herein.
Figure 12B:
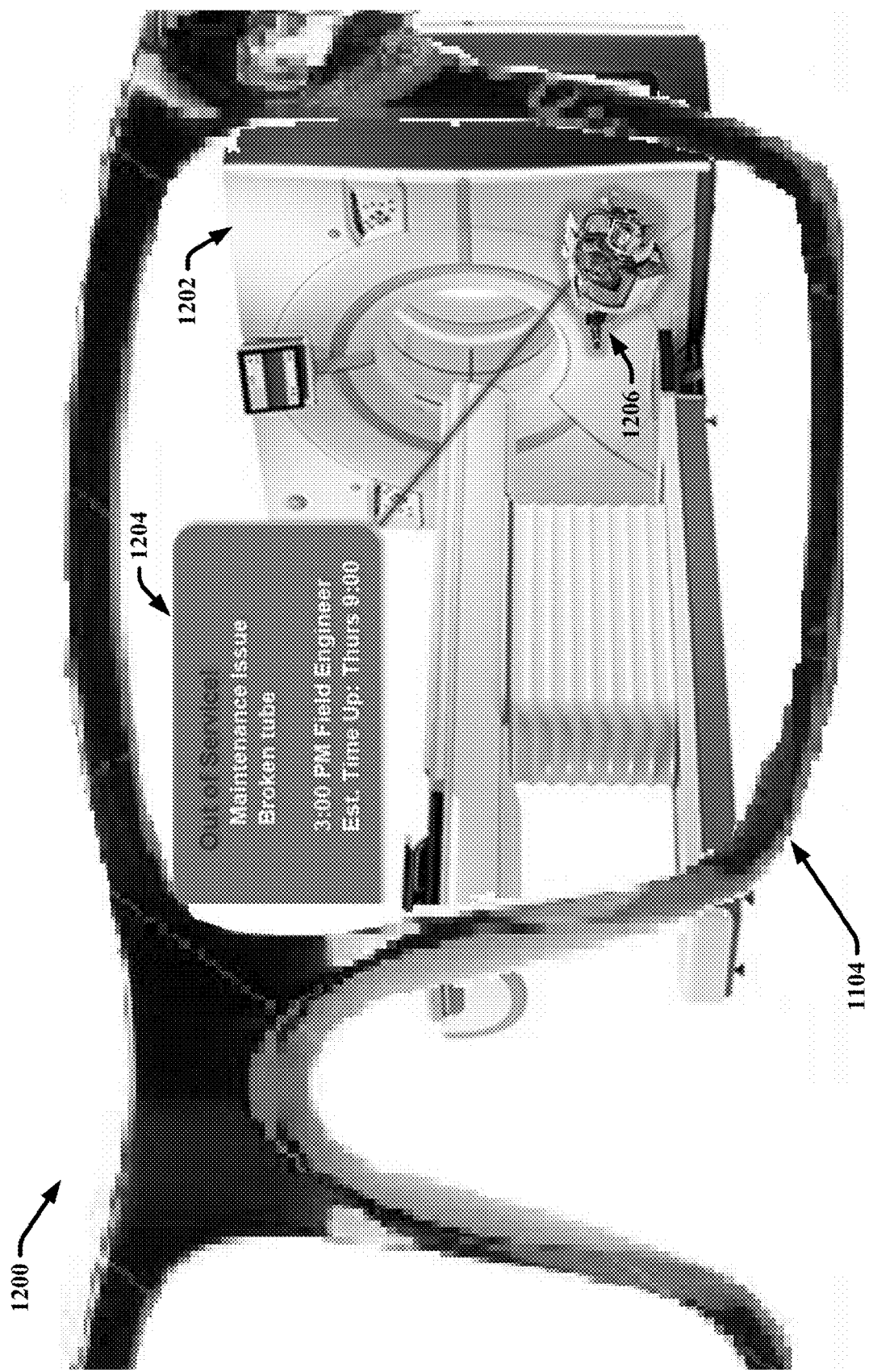

FIGS. 11, 12A and 12B presents example AR visualizations 1100 and 1200 respectively including auxiliary information regarding usage and/or performance of a healthcare system equipment in accordance with one or more embodiments described herein. One or more aspects of the example AR visualizations 1100 and 1200 demonstrate the features and functionalities of system 1000 (and additional systems described herein). Visualizations 1100 and 1200 respectively depict an area of a healthcare facility that is being viewed by a user. In the embodiments shown, the user 1102 is wearing an AR device 1104 and physically standing in the healthcare facility with a direct view of the area of the healthcare facility viewed through transparent display of the AR device 1104. However in other implementations, the user 1102 can be provided at a remote location and view image/video data of the area and/or model data of the area on a remote device. In various embodiments, the AR device 1104 can be or include user device 102. Further, the AR device 1104 can include or be communicatively coupled to the AR assistance module 110 to facilitate providing the user with auxiliary information regarding usage and/or performance of a healthcare system equipment in association with viewing the equipment.

With reference to FIG. 11, in visualization 1100, the user 1102 is viewing an imaging room of a healthcare facility that includes an imaging device 1106 and an associated computing system 1108. Visualization 1100 further includes overlay data associated with the imaging device 1106, the computing system 1108, and the imaging room in general, regarding utilization and/or performance of the imaging room and associated equipment. For example, the overlay data includes a display window 1110 associated with the imaging device 1106. The display window 1110 includes text information identifying the imaging device as a Super CT (computed tomography) machine and indicating that it has an 87% uptime. The overlay data also includes display window 1112 with text indicating that the power distribution unit (PDU) has had two failures this year. The overlay data further includes display window 1114 associated with the imaging room in general with text indicating that high radiation has been detected. This can be detected by radiation sensors in the room or in the CT machine itself.

With reference to FIG. 12A, in visualization 1200, the user 1102 is also viewing an imaging room of a healthcare facility that includes an imaging device 1202. Visualization 1200 further includes overlay data associated with the imaging device 1202 that includes a display window 1204 with text indicating the imaging device has a maintenance issue that involves a broken tube. The text also provides additional information regarding a scheduled maintenance appointment for the imaging device 1202. The display window 1204 also includes a symbol and image associated with the text. The overlay data further includes a graphical depiction 1206 of the particular part of the imaging device that is broken.

With reference to FIGS. 10, 11, and 12A in accordance with the embodiment shown, the overlay data (e.g., display windows 1110, 1112, 1114, 1204 and graphical depiction 1206) was generated by the AR component 128 based on feedback, selected from selection component 1016 regarding equipment description, utilization and/or performance information that was relevant to the user 1102. In one or more embodiments, the feedback was determined and/or generated by the feedback component 120 (e.g., via descriptive feedback component 1010, utilization feedback component 1012, and/or performance feedback component 1014), in accordance with the techniques described with reference to system 1000. The overlay data was further rendered on the display of the AR device 1104 over a direct view of the imaging room equipment viewed by the user 1102 through a transparent display of the AR device 1104.

It should be appreciated that the appearance and location of the overlay data (e.g., display windows 1110, 1112 and 1114) in visualizations 1100 and 1200 is merely exemplary and intended to convey the concept of what is actually viewed by the user through the AR device 1104. However, the appearance and location of the overlay data in visualizations 1100 and 1200 is not technically accurate, as the actual location of the overlay data would be on the glass/display of the AR device 1104. For example, FIG. 12B depicts another perspective of visualization 1200 as viewed through the lenses of the AR device 1104.

Figure 13:
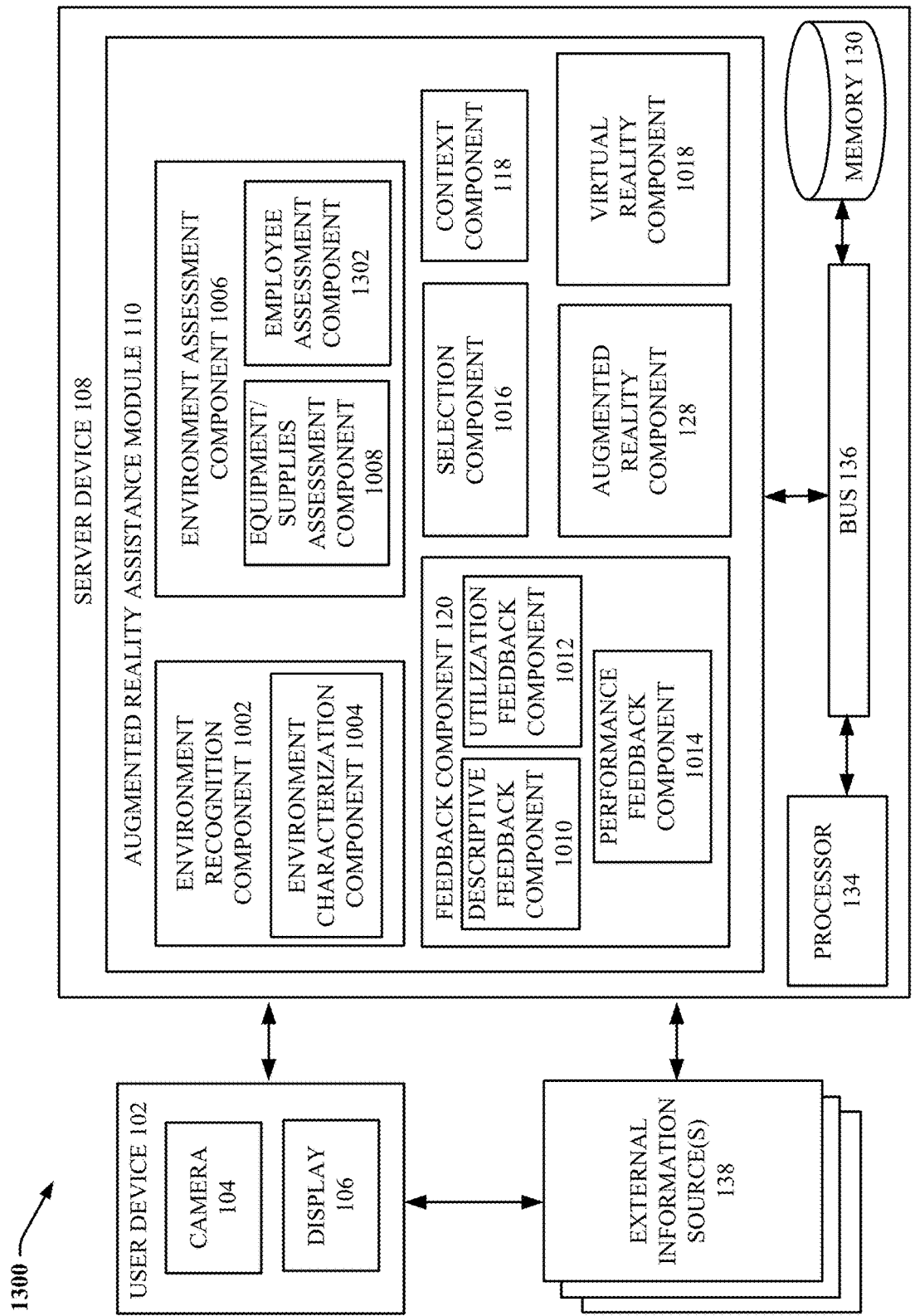
FIG. 13 illustrates a block diagram of an example system that facilitates providing auxiliary information regarding healthcare system performance using AR in accordance with one or more embodiments described herein.

FIG. 13 illustrates a block diagram of another example system 1300 that facilitates providing auxiliary information regarding healthcare system performance in real-time using AR in accordance with one or more embodiments described herein. System 1300 includes same or similar features and functionalities as system 1000 with the addition of employee assessment component 1302 to the environment assessment component 1006. Repetitive description of same or similar functionalities of like components described in prior embodiments is omitted for sake of brevity.

In addition to assessing equipment and supplies included in an area of a healthcare facility that is viewed by a user, the environment assessment component 1006 can include employee assessment component 1302 to assess employees of the healthcare organization that are included in the area. For example, in implementations in which a user is viewing a room at a healthcare facility (e.g., an operating room), the employee assessment component 1302 can determine information regarding the respective employees in the room. In another example, in implementations in which a user is walking through various areas in a healthcare facility, the employee assessment component 1302 can determine information regarding respective employees the user passes by or encounters. In another example, the environment characterization component 1004 can identify an employee that the user is looking at (e.g., within a direct line of site of the user), and determine information regarding the specific employee the user is looking at.

The employee assessment component 1302 can determine a variety of information about employees identified by the environment recognition component 1002. For example, the employee information can include but is not limited to, descriptive information that describes various facts about the employee, utilization information regarding how the employee is used by the healthcare facility, and performance information regarding the employee's evaluating the employee's performance at the healthcare organization. For example, the descriptive information could include information can include information that identifies the employee (i.e., the employee's name), identifies the job title of the employee, identifies the qualifications of the employee, identifies the duration of time the employee has worked for the healthcare organization, identifies the employee's salary, and the like. In another example, the descriptive information can include more personal information regarding the employee's preferences, family, hobbies, and the like. The usage information about an employee could include for example, information regarding the employee's duties at the healthcare organization, information regarding the employee's schedule, information regarding frequency and amount of such duties performed (e.g., number of X type procedures performed per week), and the like. Performance information associated with an employee can include information regarding how well the employee is performing his or her duties at the healthcare organization and as well as financial and/or clinical performance of the healthcare organization attributed to the employee. For example, performance information associated with a physician can include information regarding patient outcomes and satisfaction, efficiency with respect to performing his or her duties, ROI attributed to the physician's performance at the healthcare organization, and the like.

In various embodiments, the descriptive, utilization and/or performance information that is associated with respective employees identified by the environment characterization component 1004 can be predetermined and included in one or more databases accessible to the AR assistance module 110 (e.g., in memory 130, at one or more external information sources 138, or at another device). According to these embodiments, the equipment/supplies assessment component 1008 can scan various databases and sources to find and retrieve such information associated with a supply or medical equipment that is included in a user's current view. For example, the one or more external information sources 138 can include employee information identifying all healthcare professional employees of a healthcare organization that employs the AR assistance module 110 to facilitate monitoring and improving the performance of the healthcare organization. For example, the employee information can identify the respective healthcare professional employees, their roles (e.g., job title), the patients they work with (if having a clinician role), the procedures they are authorized to perform, the procedures they are expected to perform, and the like. The employee information can also include any possible performance information that can be monitored and recorded for the employee over time, such as hours worked, procedures performed, outcomes of the procedures, evaluations of the procedures, satisfaction of patients, reviews of the employee, information regarding how the employee performs certain tasks relative to other employees or another benchmark, and the like. The employee information can also include financial information regarding salary of the respective employees, whether the employee has entered overtime hours, return on investment (ROI) generated from the respective employees, and the like. The employee information can also include personal information associated with the respective employees, such as information regarding an employee's family and friends, preferences, birthday, hobbies, awards, vacations, and the like. The employee information can be updated on a regular basis (e.g., hourly, daily, weekly, etc.) such that the information source provides current information regarding various aspects of an employee's work life and personal life. In other implementations, the employee assessment component 1302 can run real-time reports on the data included in the various databases and sources to generate the utilization and performance information in real-time.

The employee assessment component 1302 can further be configured to determine information about other people identified in an area of a healthcare facility that are not employees. For example, the employee assessment component 1302 can determine information associated with patients, and visitors of the healthcare facility. Such information can also be found in one or more external information sources 138 (e.g., in patient information and records).

The feedback component 120 can be configured to collate the information retrieved, generated or determined by the employee assessment component 1302 for potential provision as auxiliary information to the user viewing the assessed area as feedback in real-time. For example, the descriptive feedback component 1010 can collect and collate descriptive information generated by the employee assessment component 1302 that describes the employees. The utilization feedback component 1012 can collect and collate utilization information generated by the employee assessment component 1302 regarding how the healthcare organization uses the respective employees, and the performance feedback component 1014 can collect and collate performance information generated by the employee assessment component 1302 regarding clinical and/or financial performance of the healthcare facility associated with employees. Such collection and collation of the descriptive, utilization, and performance information can include cleaning and indexing the information based on the respective employee each piece of information is associated with. In various implements, the feedback component 120 can associate metadata with each piece of information identifying the particular employee that it is associated with.

Given the amount of potential feedback information that can be gathered by the feedback component 120 regarding employees viewed by user, it may not be feasible or useful to provide the user with all the feedback information for each employee. For example, in some scenarios, the user may only be interested in information about a particular employee included in an area contacting several employees. In another example, the user may only be interested in receiving performance information associated with an employee as opposed to general descriptive information. The in various implementations, the amount and type of feedback information that is provided to a particular user regarding employees can be filtered and selected by the selection component 1016 based on a current context of the user. In particular, the selection component 1016 can select a subset of the feedback information (e.g., generated/collated by the feedback component 120) for provision to a user viewing an area of a healthcare facility based on a current context of the user.

In some implementations, the current context of the user can be determined by the context component 118 (e.g., based on information included in memory or one or more external information sources 138, based on received information regarding movement of the user, and the like). In this regard, the current context can include but is not limited to: a role of the user at the healthcare facility (e.g., job title and description), authorization of the user to receive various types of information (e.g., the CEO is more privy to certain financial information relative to entry level secretary), or a purpose of the user for viewing a particular area (e.g., to gain financial information, to evaluate performance associated with a specific task, etc.). For example, in an implementation in which a user is investigating performance of employees associated with billing issues, the selection component 1016 can be configured to select information to render about employees that is related to billing, such as information regarding how an employee performs at entering billing codes, number of insurance claims filed, number of claims rejected, and the like. The context of the user can also include information regarding an employee the user is currently looking at. According to this implementation, the selection component 1016 can be configured to select information regarding only the particular employee the user is looking at. The context of the user can also relate to the relationship between the user and the one or more employees included in an area viewed by the user. For example, the information provided to a user that is a supervisor of an employee would likely be different than the information provided to a user that is a subordinate of the employee. The context of a user can also include a degree of mobility of the user. For example, if the user is merely passing by an employee that the user is not well acquainted with, the user can be provided with information reminding the user of the employee's name and prompting the user to congratulate the employee on his or her promotion. Alternatively, if the user is meeting with an employee to discuss improving the employee's performance, the user can be provided with auxiliary information that highlights some important past performance statistics.

Similar to the feedback information provided to user in association with equipment and supplies, in some implementations the AR component 128 can provide the user with employee feedback information using an AR experience. According to these implementations, the AR component 128 can generate overlay data that comprises or represents the subset of the employee feedback information selected by the selection component 1016 for providing to the user. In another implementation, the VR component 1018 to generate overlay data for rendering to a user in a VR experience. With respect to rendering the overlay data in either AR or VR, in one or more embodiments, the user device (e.g., via rendering component 812), can be configured to associated the overlay data at positions that coincide with the respective employees that it is associated with.

In large healthcare institutions with hundreds or thousands of employees and even more patients, the ability to provide team members and leadership with quick understanding and information about their colleagues has great value to growing the team and overall employee management. Relationships can be enhanced through such technology as well as improved employee coaching.

Figure 14:
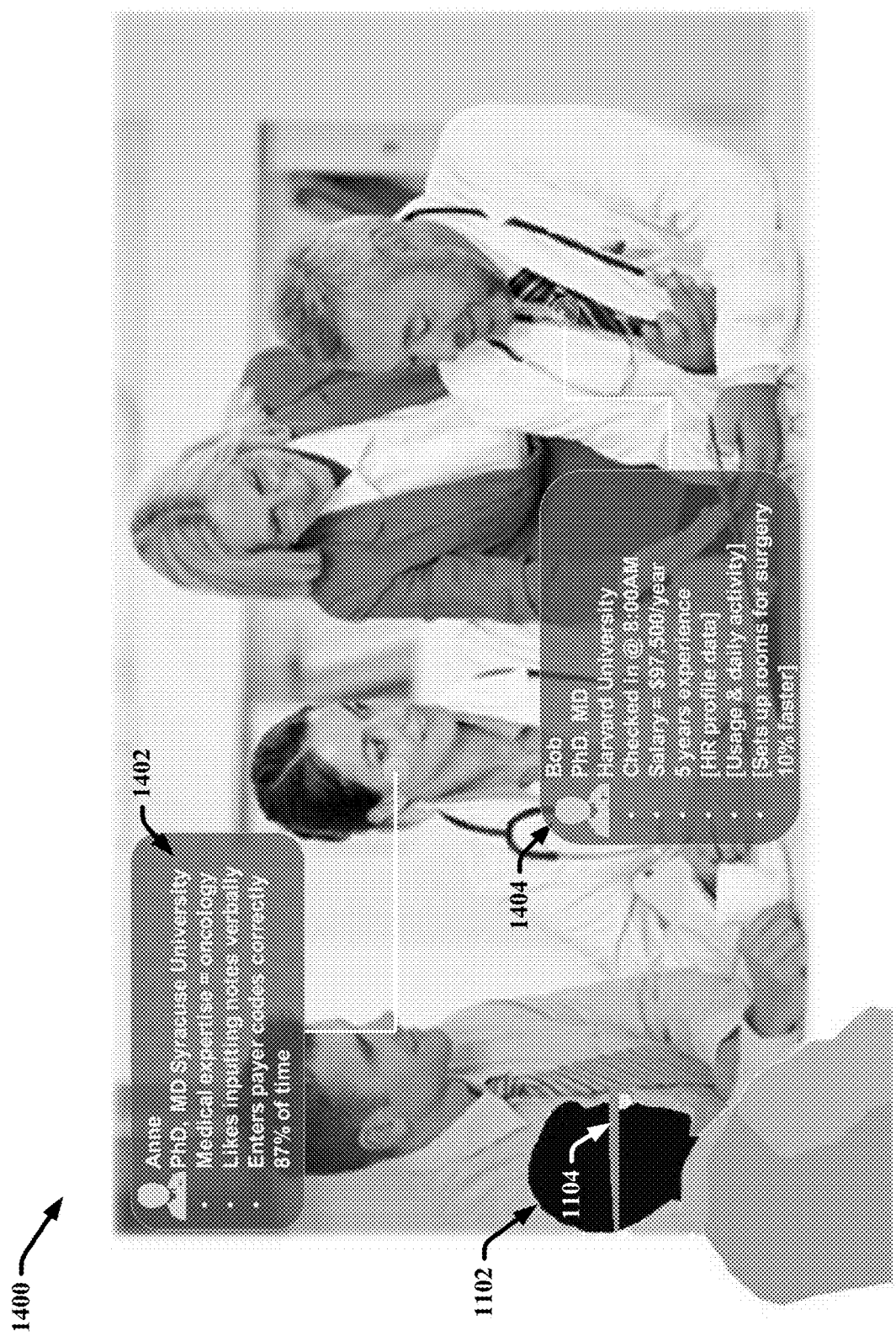
FIG. 14 presents an example AR visualization including auxiliary information regarding employees of a healthcare organization in accordance with one or more embodiments described herein.

FIG. 14 presents an example AR visualization 1400 including auxiliary information regarding employees of a healthcare organization in accordance with one or more embodiments described herein. One or more aspects of the example AR visualization 1400 demonstrate the features and functionalities of system 1300 (and additional systems described herein) with respect to employee assessment component 1302. Visualization 1400 depicts an area of a healthcare facility that is being viewed by a user 1102. The area includes four people, two physicians Anne and Bob, and two administrative personnel. In the embodiments shown, the user 1102 is wearing an AR device 1104 and physically standing in the healthcare facility with a direct view of the area of the healthcare facility viewed through transparent display of the AR device 1104. However in other implementations, the user 1102 can be provided at a remote location and view image/video data of the area and/or model data of the area on a remote device. In various embodiments, the AR device 1104 can be or include user device 102.

Further, the AR device 1104 can include or be communicatively coupled to the AR assistance module 110 to facilitate providing the user with auxiliary information regarding usage and/or performance of a healthcare system equipment in association with viewing the equipment.

Visualization 1400 further includes overlay data associated with physicians Anne and Bob respectively presented in display windows 1402 and 1404. For example, display window 1402 associated with Anne includes a few bullet points with text describing some facts about Anne, including her qualifications, expertise, preferences and performance with respect to entering payer cods correctly. Likewise, display window 1404 associated with bob includes a few more bullet points with text describing some facts about Bob, including his qualifications, check in time, salary, experience, HR profile data, usage and daily activity data, and statistics regarding surgery room set up performance.

With reference to FIGS. 13 and 14 in accordance with the embodiment shown, the overlay data (e.g., display windows 1402 and 1404) was generated by the AR component 128 based on feedback, selected from selection component 1016 regarding employee description, performance and utilization information that was relevant to the user 1102. In one or more embodiments, the feedback was determined and/or generated by the feedback component 120 (e.g., via descriptive feedback component 1010, utilization feedback component 1012, and/or performance feedback component 1014), in accordance with the techniques described with reference to systems 1000 and 1300. The overlay data was further rendered on the display of the AR device 1102 over a direct view of the imaging room equipment viewed by the user 1102 through a transparent display of the AR device 1104. It should be appreciated that the appearance and location of the overlay data (e.g., display windows 1402 and 1404) in visualization 1400 is merely exemplary and intended to convey the concept of what is actually viewed by the user through the AR device 1104. However, the appearance and location of the overlay data in visualization 1400 is not technically accurate, as the actual location of the overlay data would be on the glass/display of the AR device 1104.

Figure 15:
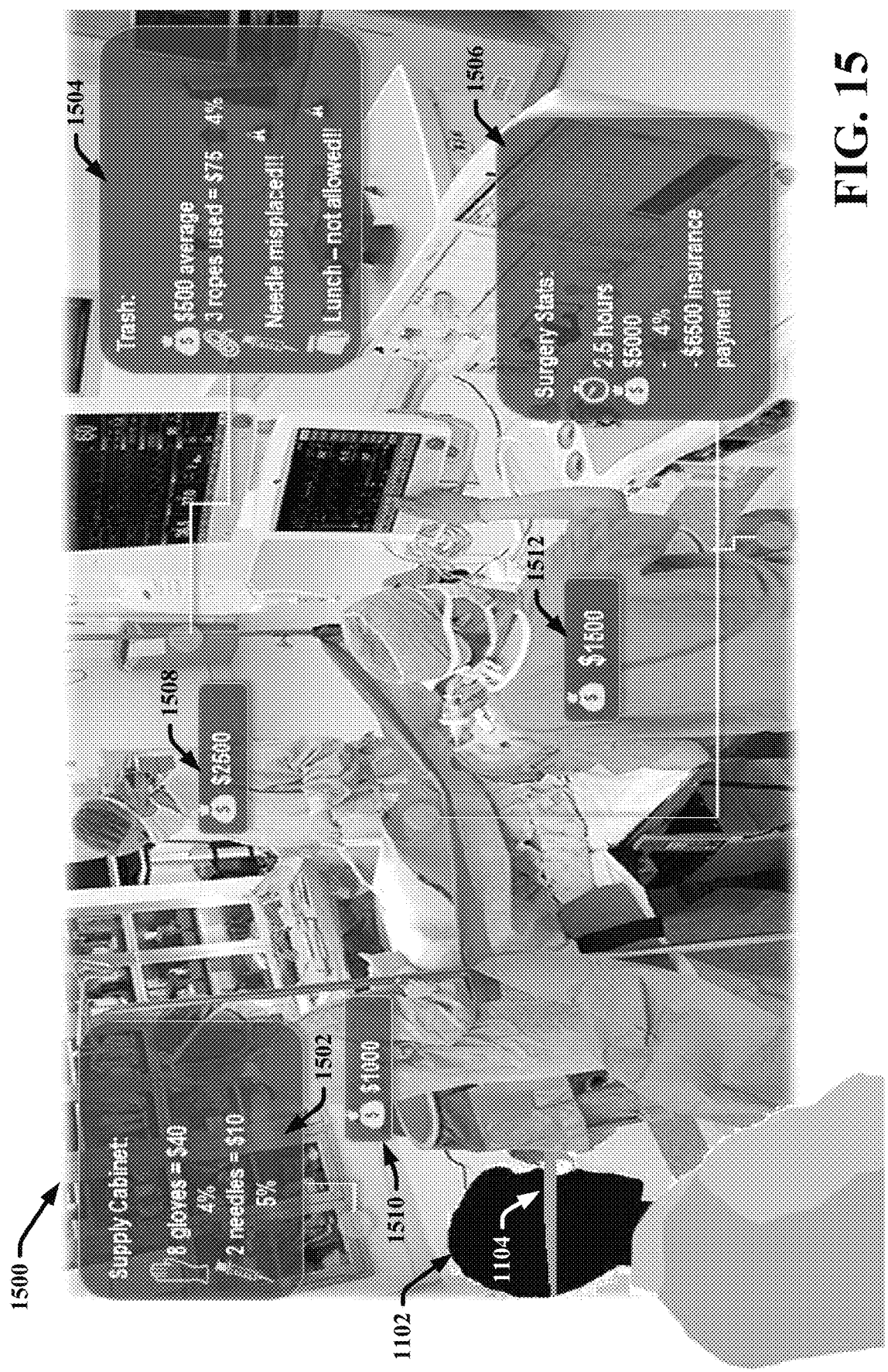
FIG. 15 presents an example AR visualization including auxiliary information regarding various aspects of an operating room environment in accordance with one or more embodiments described herein.

FIG. 15 presents an example AR visualization 1500 including auxiliary information regarding various aspects of an operating room environment in accordance with one or more embodiments described herein. One or more aspects of the example AR visualization 1500 demonstrate the features and functionalities of systems 1000 and 1300 (and additional systems described herein) with respect to equipment/supplies assessment component 1008 and employee assessment component 1302.

Visualization 1500 depicts an operating room environment of a healthcare facility that is being viewed by a user 1102. The environment includes three physicians operating on a patient. In the embodiments shown, the user 1102 is wearing an AR device 1104 and physically standing in the healthcare facility with a direct view of the area of the operating room environment viewed through transparent display of the AR device 1104. However in other implementations, the user 1102 can be provided at a remote location and view image/video data of the area and/or model data of the area on a remote device. In various embodiments, the AR device 1104 can be or include user device 102. Further, the AR device 1104 can include or be communicatively coupled to the AR assistance module 110 to facilitate providing the user with auxiliary information regarding usage and/or performance of a healthcare system equipment in association with viewing the equipment.

Visualization 1500 further includes overlay data comprising information associated with various supplies, equipment and people (e.g., the physicians and the patient) included in the operating room respectively determined by the equipment/supplies assessment component 1008 and the employee assessment component 1302. The specific information represented in the overlay data includes utilization and performance information associated with the various supplies, equipment and people, that the selection component 1016 determined was relevant to the context of the user 1102. For example, display window 1502 includes supply utilization information regarding gloves and needles in the supply cabinet. Display window 1502 also includes financial performance information regarding costs attributed to the gloves and needles. Display window 1504 includes information regarding costs associated with the trash, including information regarding supply utilization and costs associated therewith. Display window 1506 includes information regarding the surgery being performed on the patient, including descriptive information about the surgery, and financial performance information. Further, the overlay data includes display windows 1508, 1510, and 1512 respectively providing cost information regarding cost attributed to the utilization of the respective physicians for the current surgery. As with the other visualizations described herein, it should be appreciated that the appearance and location of the overlay data (e.g., display windows 1502-1512) in visualization 1500 is merely exemplary and intended to convey the concept of what is actually viewed by the user through the AR device 1104. However, the appearance and location of the overlay data in visualization 1500 is not technically accurate, as the actual location of the overlay data would be on the glass/display of the AR device 1104.

A user, through a user interface should as in-air motion signals, can control the AR to show, edit, and change its display based on their intentions. A camera can detect such signals and the system 100 can adjust the overlay data accordingly.

Figure 16:
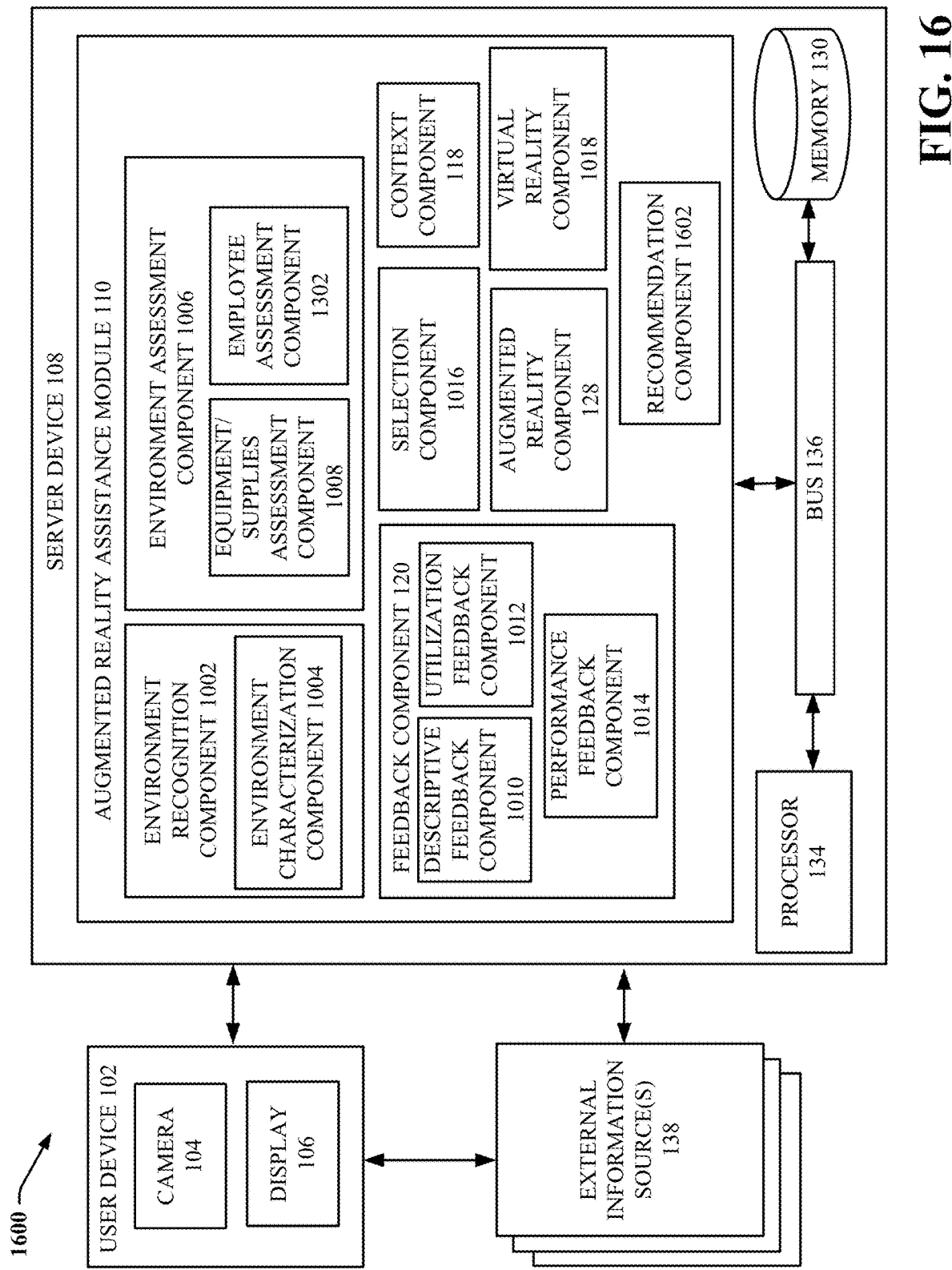
FIG. 16 illustrates a block diagram of an example system that facilitates providing auxiliary information regarding healthcare system performance using AR in accordance with one or more embodiments described herein.

FIG. 16 illustrates a block diagram of another example system 1600 that facilitates providing auxiliary information regarding healthcare system performance in real-time using AR in accordance with one or more embodiments described herein. System 1600 includes same or similar feature and functionalities as system 1300 with the addition of recommendation component 1602. Repetitive description of same or similar functionalities of like components described in prior embodiments is omitted for sake of brevity.

In one or more embodiments, the recommendation component 1602 can be configured to analyze the various information/data included in the one or more external information sources 138 (and/or in memory 130), as well as the information determined by the environment assessment component 1006 over time to determine recommendation information regarding how to improve an aspect of the state of performance of the healthcare organization. For example, the recommendation component 1602 can evaluate past performance information regarding the clinical and/or financial performance of the healthcare organization associated with utilization of various equipment, supplies and employees of the healthcare organization. Using one or more machine learning and/or deep learning techniques, the recommendation component 1602 can identify patterns in the data attributed to financial and/or clinical gains and losses and determine recommendation information regarding how to improve financial and/or clinical gain and minimize financial and/or clinical loss. For example, such recommendation information can include the addition or removal of resources, changes to manners in which the healthcare organization uses respective equipment, supplies and employees, and the like. Relevant recommendation information (e.g., relevant to a current area being viewed by a user and a current context of the user) can further be selected by the selection component 1016 and provided to a user as overlay data in an AR or VR experience.

In one or more additional embodiments, the recommendation component 1602 can determine recommendation information for providing by a user to a person (e.g., an employee, a patient or other type of person) that the user encounters regarding suggested things for the user to say to the person. The recommendation can be based on a current context of the user, relevant current information about the other person, and a relationship between the user and the other person. For example, with respect to an employee, the recommendation component 1602 can determine a suggested thing to say to a particular employee the user encounters that would improving the clinical and financial performance of the healthcare organization. According to this example, using one or more machine learning or deep learning techniques, the recommendation component 1602 can evaluate past performance information associated with an employee and determine an aspect of the employees' past performance that needs improvement. The recommendation component 1602 can also determine based on the current context of the user and the employee, a relevant suggested remark for the user to say to the employee that would encourage the employee to improve his or her performance. The suggested remark can further be provided to the user as overlay data in AR or VR when the user encounters the employee.

For example, in association with a user encountering another employee, the recommendation component 1602 might suggest the user state: "How was your birthday last week?", (e.g., as determined by the recommendation component 1602 based on a birthday in the employee record, comparison to current day, and a determination that the employees birthday was last 6 days ago). In another example, in association with a user encountering physician at a hospital, the recommendation component 1602 might suggest the user state: "You had a lot of surgeries yesterday, how'd it go?", (e.g., as determined by the recommendation component 1602 based on utilization information indicating the physician performed 12 surgeries, comparing this information with the average amount of surgeries performed by the physician to determine a 25% higher than normal). In another example, in association with a user encountering another employee, the recommendation component 1602 might suggest the user state: "Is that CT machine in bay 211 still giving you issues?", (e.g., based on determinations by the recommendation component 1602 that the user and the employee are located in bay 211 and that the CT machine has been under service more than a standard amount). Providing "average" or "mean" information against the rest of the healthcare institution or industry can be incredibly valuable to management and also can provide competitive incentive for staff to improve to continue to be excellent in their field.

Figure 17:
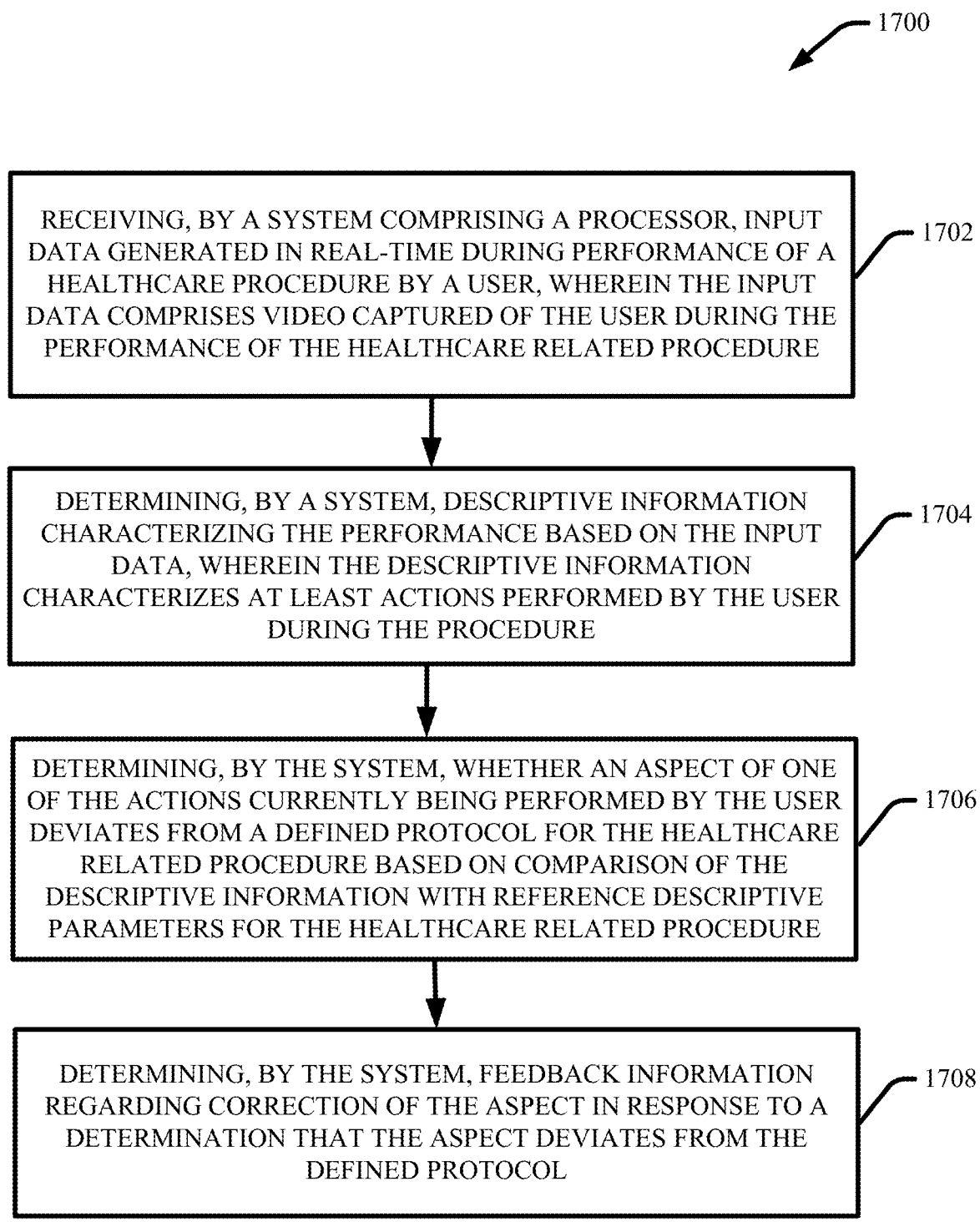
FIG. 17 illustrates a flow diagram of an example method that facilitates providing auxiliary information regarding healthcare procedure performance using AR in accordance with one or more embodiments described herein.

FIG. 17 illustrates a flow diagram of an example method 1700 that facilitates providing auxiliary information regarding healthcare procedure performance using AR in accordance with one or more embodiments described herein. Repetitive description of like elements employed in other embodiments described herein is omitted for sake of brevity.

At 1702, a system comprising a processor (e.g., system 100, 600 or 700), receives input data generated in real-time during performance of a healthcare procedure by a user, wherein the input data comprises video captured of the user during the performance of the healthcare related procedure. At 1704, the system, determines descriptive information characterizing the performance based on the input data, wherein the descriptive information characterizes at least actions performed by the user during the procedure (e.g., via procedure characterization component 114). At 1706, the system determines by whether an aspect of one of the actions currently being performed by the user deviates from a defined protocol for the healthcare related procedure based on comparison of the descriptive information with reference descriptive parameters for the healthcare related procedure (e.g., via procedure assessment component 116). At 1708, the system determines feedback information regarding correction of the aspect in response to a determination that the aspect deviates from the defined protocol (e.g., via feedback component 120).

Figure 18:
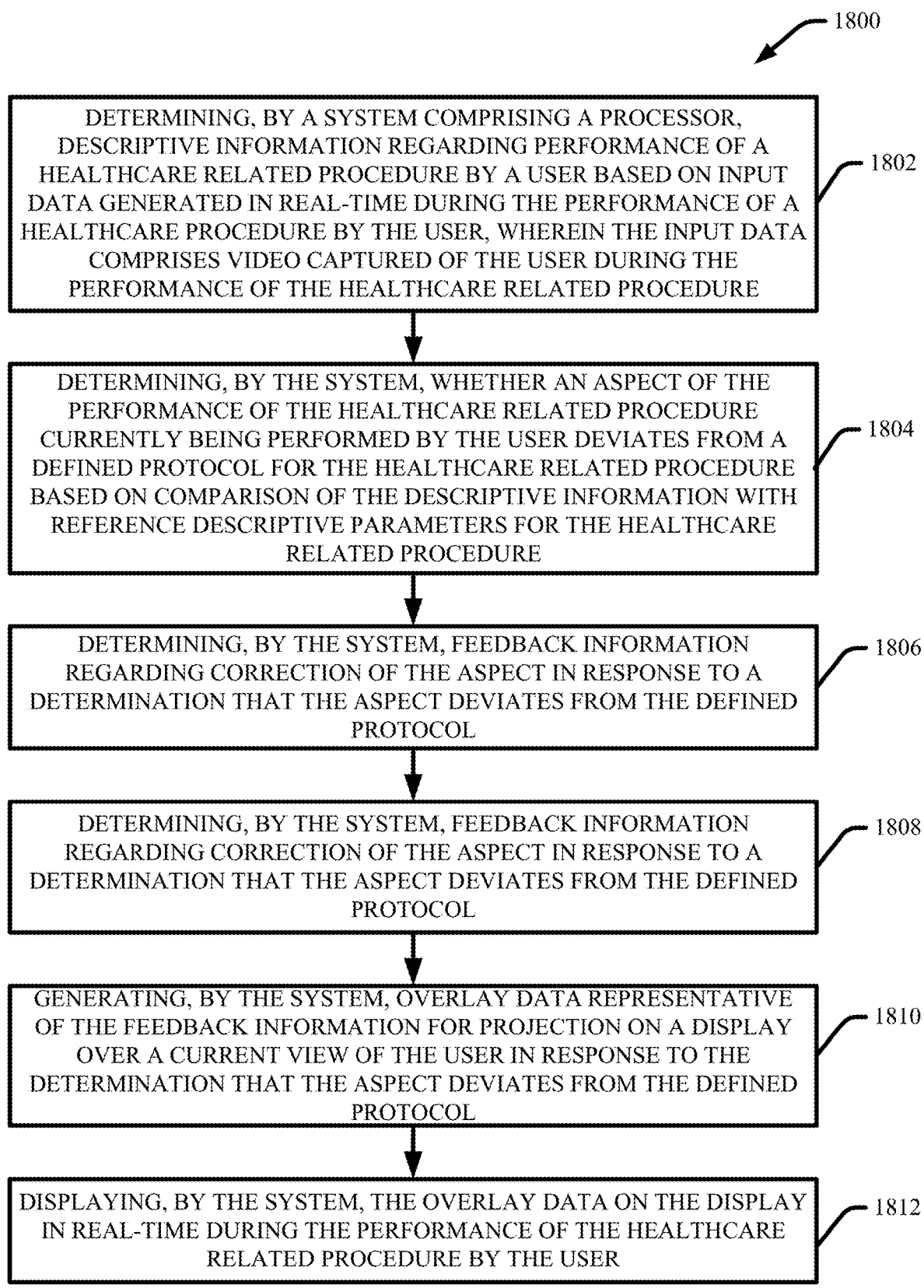
FIG. 18 illustrates a flow diagram of another example method that facilitates providing auxiliary information regarding healthcare procedure performance using AR in accordance with one or more embodiments described herein.

FIG. 18 illustrates a flow diagram of another example method 1800 that facilitates providing auxiliary information regarding healthcare procedure performance using AR in accordance with one or more embodiments described herein. Repetitive description of like elements employed in other embodiments described herein is omitted for sake of brevity.

At 1802, a system comprising a processor (e.g., system 100, 600 or 700), determines descriptive information regarding performance of a healthcare related procedure by a user based on input data generated in real-time during the performance of a healthcare procedure by the user, wherein the input data comprises video captured of the user during the performance of the healthcare related procedure (e.g., via procedure assessment component 116). At 1804, the system determines whether an aspect of the performance of the healthcare related procedure currently being performed by the user deviates from a defined protocol for the healthcare related procedure based on comparison of the descriptive information with reference descriptive parameters for the healthcare related procedure (e.g., via procedure assessment component 116). At 1806, the system determines feedback information regarding correction of the aspect in response to a determination that the aspect deviates from the defined protocol (e.g., via feedback component 120). At 1808, the system generates overlay data representative of the feedback information for projection on a display over a current view of the user in response to the determination that the aspect deviates from the defined protocol (e.g., via AR component 128). At 1810, the system displays the overlay data on the display in real-time during the performance of the healthcare related procedure by the user (e.g., via rendering component 812).

Figure 19:
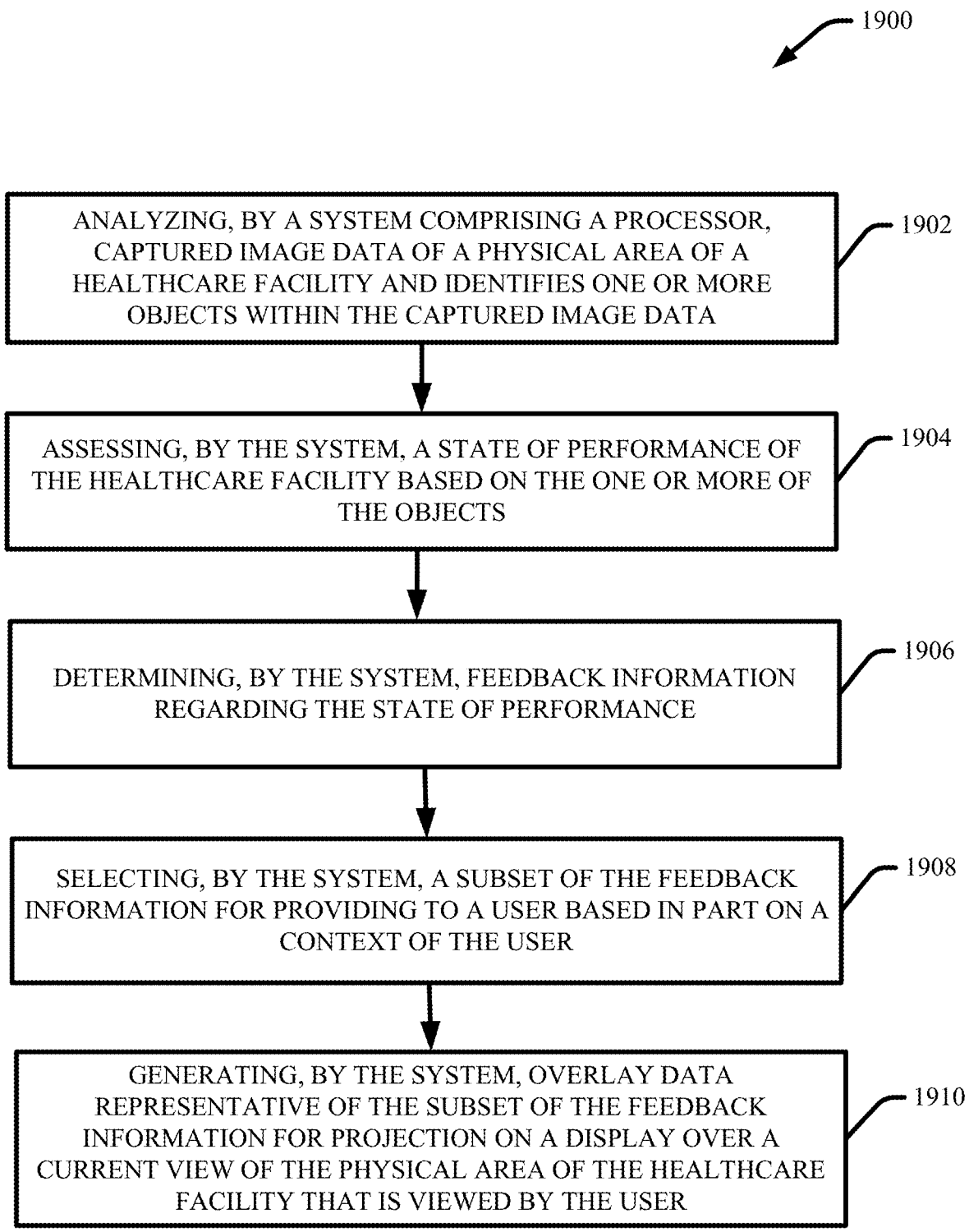
FIG. 19 illustrates a flow diagram of an example method that facilitates providing auxiliary information regarding healthcare system performance using AR in accordance with one or more embodiments described herein.

FIG. 19 illustrates a flow diagram of an example method 1900 that facilitates providing auxiliary information regarding healthcare system performance in real-time using AR in accordance with one or more embodiments described herein. Repetitive description of like elements employed in other embodiments described herein is omitted for sake of brevity.

At 1902, a system comprising a processor (e.g., system 1000, 1300 or 1600), analyzes captured image data of a physical area of a healthcare facility and identifies one or more objects within the captured image data (e.g., via environment characterization component 1004). At 1904, the system assesses a state of performance of the healthcare facility based on the one or more of the objects (e.g., via environment assessment component 1006). At 1906, the system determines feedback information regarding the state of performance (e.g., via feedback component 120). At 1908, the system selects a subset of the feedback information for providing to a user based in part on a context of the user (e.g., via selection component 1016). At 1910, the system generates overlay data representative of the subset of the feedback information for projection on a display over a current view of the physical area of the healthcare facility that is viewed by the user (e.g., via AR component 128).

Figure 20:
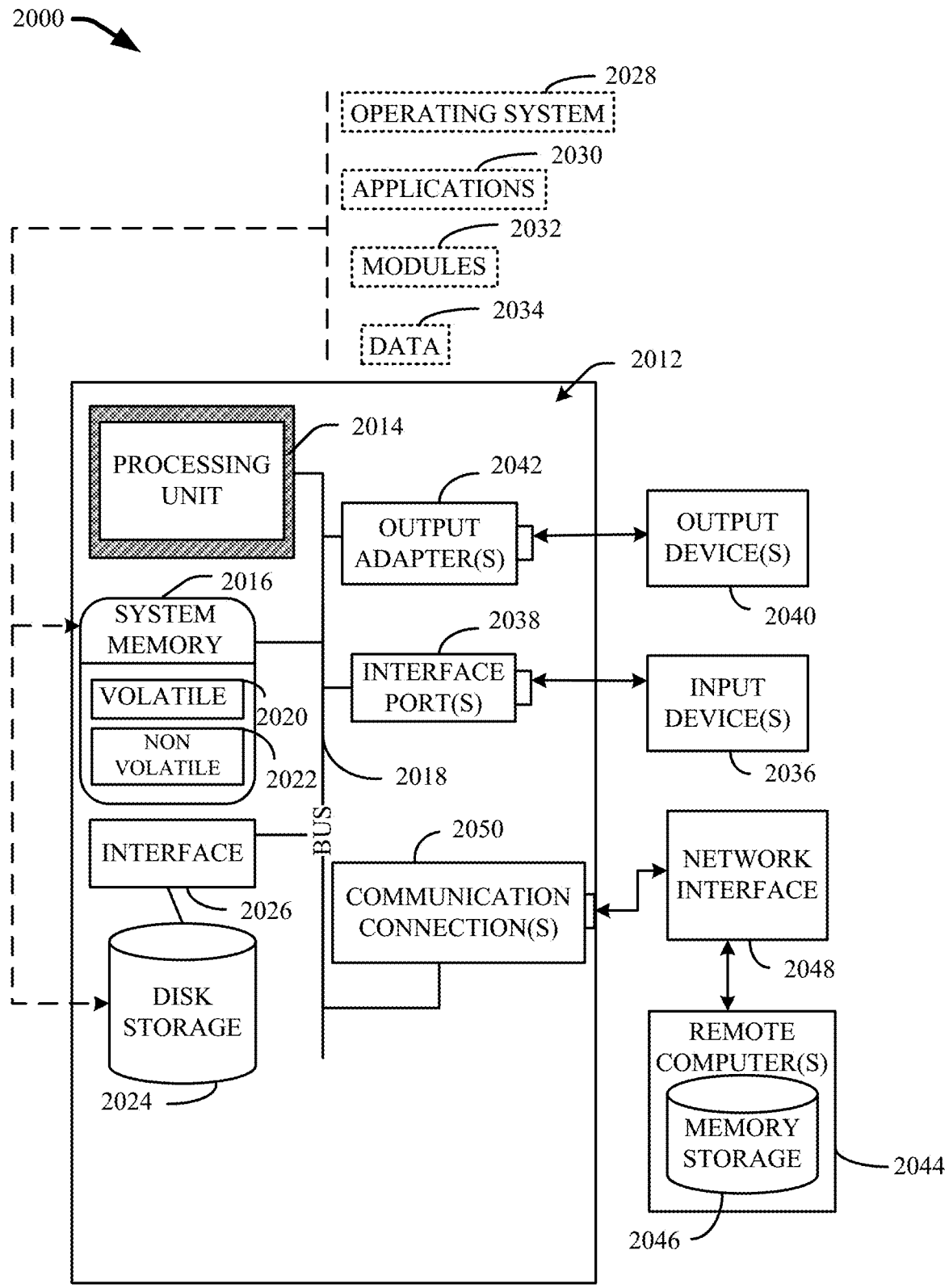
FIG. 20 illustrates a block diagram of an example non-limiting operating environment in which one or more embodiments described herein can be facilitated.

In order to provide a context for the various aspects of the disclosed subject matter, FIG. 20 as well as the following discussion are intended to provide a general description of a suitable environment in which the various aspects of the disclosed subject matter can be implemented. FIG. 20 illustrates a block diagram of an example, non-limiting operating environment in which one or more embodiments described herein can be facilitated. Repetitive description of like elements employed in other embodiments described herein is omitted for sake of brevity.

With reference to FIG. 20, a suitable operating environment 2001 for implementing various aspects of this disclosure can also include a computer 2012. The computer 2012 can also include a processing unit 2014, a system memory 2016, and a system bus 2018. The system bus 2018 couples system components including, but not limited to, the system memory 2016 to the processing unit 2014. The processing unit 2014 can be any of various available processors. Dual microprocessors and other multiprocessor architectures also can be employed as the processing unit 2014. The system bus 2018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 2094), and Small Computer Systems Interface (SCSI). The system memory 2016 can also include volatile memory 2020 and nonvolatile memory 2022. The basic input/output system (BIOS), containing the basic routines to transfer information between elements within the computer 2012, such as during start-up, is stored in nonvolatile memory 2022. By way of illustration, and not limitation, nonvolatile memory 2022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 2020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 2012 can also include removable/non-removable, volatile/non-volatile computer storage media. FIG. 20 illustrates, for example, a disk storage 2024. Disk storage 2024 can also include, but is not limited to, devices like a magnetic disk drive, floppy disk drive, tape drive, Jaz drive, Zip drive, LS-100 drive, flash memory card, or memory stick. The disk storage 2024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 2024 to the system bus 2018, a removable or non-removable interface is typically used, such as interface 2026. FIG. 20 also depicts software that acts as an intermediary between users and the basic computer resources described in the suitable operating environment 2001. Such software can also include, for example, an operating system 2028. Operating system 2028, which can be stored on disk storage 2024, acts to control and allocate resources of the computer 2012. System applications 2030 take advantage of the management of resources by operating system 2028 through program modules 2032 and program data 2034, e.g., stored either in system memory 2016 or on disk storage 2024. It is to be appreciated that this disclosure can be implemented with various operating systems or combinations of operating systems. A user enters commands or information into the computer 2012 through input device(s) 2036. Input devices 2036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 2014 through the system bus 2018 via interface port(s) 2038. Interface port(s) 2038 include, for example, a serial port, a parallel port, a game port, and a universal serial bus (USB). Output device(s) 2040 use some of the same type of ports as input device(s) 2036. Thus, for example, a USB port can be used to provide input to computer 2012, and to output information from computer 2012 to an output device 2040. Output adapter 2042 is provided to illustrate that there are some output devices 2040 like monitors, speakers, and printers, among other output devices 2040, which require special adapters. The output adapters 2042 include, by way of illustration and not limitation, video and sound cards that provide a means of connection between the output device 2040 and the system bus 2018. It should be noted that other devices and/or systems of devices provide both input and output capabilities such as remote computer(s) 2044.

Computer 2012 can operate in a networked environment using logical connections to one or more remote computers, such as remote computer(s) 2044. The remote computer(s) 2044 can be a computer, a server, a router, a network PC, a workstation, a microprocessor based appliance, a peer device or other common network node and the like, and typically can also include many or all of the elements described relative to computer 2012. For purposes of brevity, only a memory storage device 2046 is illustrated with remote computer(s) 2044. Remote computer(s) 2044 is logically connected to computer 2012 through a network interface 2048 and then physically connected via communication connection 2050. Network interface 2048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 2050 refers to the hardware/software employed to connect the network interface 2048 to the system bus 2018. While communication connection 2050 is shown for illustrative clarity inside computer 2012, it can also be external to computer 2012. The hardware/software for connection to the network interface 2048 can also include, for exemplary purposes only, internal and external technologies such as, modems including regular telephone grade modems, cable modems and DSL modems, ISDN adapters, and Ethernet cards.

Embodiments of the present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has,"

"possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components;
a processor that executes computer executable components stored in the memory, wherein the computer executable components comprise:
an environment recognition component configured to identify an area of a healthcare facility included in image data captured of the healthcare facility;
an environment characterization component configured to identify medical resources included in the area based on the image data, wherein the medical resources comprise one or more medical supplies;
an environment assessment component configured to determine resource utilization information associated with usage of the medical resources at the healthcare facility and cost information regarding costs associated with the usage, wherein the resource utilization information comprises supply usage information regarding usage of the one or more medical supplies, and wherein the cost information comprises supply cost information associated with the usage of the one or more medical supplies,
wherein the supply usage information identifies a clinical success rate associated with usage of a first medical supply of the one or more medical supplies and a second clinical success rate associated with usage of an alternative medical supply; and
an augmented reality component configured to generate and display overlay data comprising the resource utilization information and the cost information for projection on a display of a device over a current view of the area as viewed on or through the display.

2. The system of claim 1, wherein the computer executable components further comprise:
a rendering component configured to present the overlay data on the display and spatially align the overlay data with the medical resources.

3. The system of claim 2, wherein the display is integrated into an eyewear device worn by the user.

4. The system of claim 1, wherein the area comprises an operating room where a medical procedure is currently being performed on a patient by at least one clinician, and wherein the cost information comprises clinician costs attributed to usage of the clinician for the procedure.

5. A method comprising:
identifying, by a system comprising a processor, an area of a healthcare facility included in image data captured of the healthcare facility;
identifying, by the system, medical resources included in the area based on analysis of the image data, wherein the medical resources comprise one or more medical supplies;
determining, by the system, resource utilization information associated with usage of the medical resources at the healthcare facility, wherein the resource utilization information comprises supply usage information regarding usage of the one or more medical supplies;
determining, by the system, cost information regarding costs associated with the usage, wherein the cost information comprises supply cost information associated with the usage of the one or more medical supplies,
wherein the supply usage information identifies a clinical success rate associated with usage of a first medical supply of the one or more medical supplies and a second clinical success rate associated with usage of an alternative medical supply; and
generating and displaying, by the system, overlay data comprising the resource utilization information and the cost information for projection on a display of a device over a current view of the area as viewed on or through the display.

6. The method of claim 5, further comprising:
rendering, by the system, the overlay data on the display and spatially aligning the overlay data with the medical resources.

7. A non-transitory machine-readable storage medium, comprising executable instructions that, when executed by a processor, facilitate performance of operations, comprising:
receiving image data captured of an area of a healthcare facility;
identifying resources included in the area based on analysis of the image data, wherein the resources comprise one or more medical supplies;
determining resource utilization information associated with usage of the medical resource at the healthcare facility, wherein the resource utilization information comprises supply usage information regarding usage of the one or more medical supplies;
determining, by the system, cost information regarding costs associated with the usage, wherein the cost information comprises supply cost information associated with the usage of the one or more medical supplies,
wherein the supply usage information identifies a clinical success rate associated with usage of a first medical supply of the one or more medical supplies and a second clinical success rate associated with usage of an alternative medical supply; and
generating and displaying overlay data comprising the resource utilization information and the cost information for projection on a display of a device over a current view of the area as viewed on or through the display.

8. The machine-readable storage medium of claim 7, wherein the operations further comprise:
rendering the overlay data on the display and spatially aligning the overlay data with the medical resource.

9. The system of claim 1, wherein the supply usage information identifies an amount or frequency of past usage of the one or more medical supplies.

10. The system of claim 1, wherein the supply usage information identifies an amount or frequency of expected future usage of the one or more medical supplies.

11. The system of claim 1, wherein the supply usage information indicates whether there is a surplus or a deficiency in amount of the one or more medical supplies.

12. The system of claim 1, wherein the supply cost information comprises financial gain or loss information attributed to the usage of the one or more medical supplies.

13. The system of claim 1, wherein the one or more medical supplies comprise a piece of medical equipment, and wherein the supply cost information comprises a measure of financial return on investment for the piece of medical equipment.

14. The system of claim 1, wherein the medical resources comprise one or more medical workers, wherein the resource utilization information comprises worker usage information regarding usage of the one or more medical workers, and wherein the cost information comprises medical worker cost information associated with the usage of the one or more medical workers.

15. The system of claim 14, wherein the worker usage information comprises performance information regarding performance of job responsibilities of the one or more medical workers at the healthcare facility.

16. The system of claim 15, wherein the worker cost information comprises a measure of financial return on investment for the one or more workers determined based on the performance information.

17. The system of claim 1, wherein the computer executable components further comprise:
   a recommendation component that determines financial and clinical losses attributed to the medical resources based on evaluation of the utilization information and the cost information, and wherein the augmented reality component includes loss information regarding the financial and clinical losses in the overlay data.

18. The system of claim 17, wherein the recommendation component employs one or more machine learning techniques to determine the financial and clinical losses.

* * * * *